(12) United States Patent
Hood et al.

(10) Patent No.: US 9,024,766 B2
(45) Date of Patent: May 5, 2015

(54) BEVERAGE CONTAINERS WITH DETECTION CAPABILITY

(75) Inventors: Leroy E. Hood, Seattle, WA (US); Edward K.Y. Jung, Bellevue, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund, LLC, Bellevue, WA (US)

( * ) Notice: Subject to any disclaimer, the term of this patent is extended or adjusted under 35 U.S.C. 154(b) by 1184 days.

(21) Appl. No.: 12/584,364

(22) Filed: Sep. 2, 2009

(65) Prior Publication Data
US 2011/0050431 A1    Mar. 3, 2011

Related U.S. Application Data

(63) Continuation-in-part of application No. 12/584,055, filed on Aug. 28, 2009, now Pat. No. 8,898,069, and a continuation-in-part of application No. 12/584,054, filed on Aug. 28, 2009, now Pat. No. 8,810,417.

(51) Int. Cl.
*G08B 21/00* (2006.01)
*A47G 19/22* (2006.01)

(52) U.S. Cl.
CPC .................................. *A47G 19/2227* (2013.01)

(58) Field of Classification Search
USPC ......... 340/618, 573.3, 539, 603, 620; 702/22; 422/68.1; 73/61.43, 426; 436/104; 99/279, 285
See application file for complete search history.

(56) References Cited

U.S. PATENT DOCUMENTS

| 4,275,083 A | 6/1981 | Colten et al. |
| 4,843,830 A | 7/1989 | Haul |
| 5,174,962 A | 12/1992 | Brennan |
| 5,183,740 A | 2/1993 | Ligler et al. |
| 5,303,585 A | 4/1994 | Lichte |

(Continued)

FOREIGN PATENT DOCUMENTS

| EP | 1 397 997 A1 | 3/2004 |
| WO | WO 99/31560 | 6/1999 |

(Continued)

OTHER PUBLICATIONS

Abrámoff, Michael D., et al.; "Image Processing with ImageJ"; Biophotonics International; Bearing a date of Jul. 2004; pp. 36-42; The British Library.

(Continued)

*Primary Examiner* — Hoi Lau
(74) *Attorney, Agent, or Firm* — Dorsey & Whitney LLP

(57) ABSTRACT

Methods and systems described herein include individual-use beverage containers including sensors and methods of their use. Beverage containers include: a vessel body configured to hold a beverage; and at least one sensor associated with the vessel body, the at least one sensor including a sensor configured to detect one or more substance in a fluid. Systems include: at least one beverage container including at least one sensor configured to detect one or more substance in fluid; and at least one external device including at least one port configured for communication with the at least one sensor. Methods include: detecting one or more substance within fluid with at least one sensor integral to a beverage container; and interfacing one or more of the at least one sensor with an external device.

53 Claims, 14 Drawing Sheets

(56) References Cited

U.S. PATENT DOCUMENTS

| | | | |
|---|---|---|---|
| 5,354,654 A | 10/1994 | Ligler et al. | |
| 5,360,819 A | 11/1994 | Giese | |
| 5,475,096 A | 12/1995 | Gold et al. | |
| 5,516,931 A | 5/1996 | Giese et al. | |
| 5,571,401 A | 11/1996 | Lewis et al. | |
| 5,602,273 A | 2/1997 | Giese et al. | |
| 5,604,104 A | 2/1997 | Giese et al. | |
| 5,610,020 A | 3/1997 | Giese et al. | |
| 5,631,146 A | 5/1997 | Szostak et al. | |
| 5,661,039 A | 8/1997 | Kung et al. | |
| 5,762,939 A | 6/1998 | Smith et al. | |
| 5,804,563 A | 9/1998 | Still et al. | |
| 5,807,758 A | 9/1998 | Lee et al. | |
| 5,831,012 A | 11/1998 | Nilsson et al. | |
| 6,022,326 A | 2/2000 | Tatum et al. | |
| 6,102,872 A | 8/2000 | Doneen et al. | |
| 6,163,248 A * | 12/2000 | Paek et al. | 340/321 |
| 6,187,599 B1 | 2/2001 | Asher et al. | |
| 6,214,546 B1 | 4/2001 | Asher et al. | |
| 6,255,461 B1 | 7/2001 | Mosbach et al. | |
| 6,258,870 B1 | 7/2001 | Hubbell et al. | |
| 6,310,105 B1 | 10/2001 | Damodaran | |
| 6,372,248 B1 | 4/2002 | Qin et al. | |
| 6,397,190 B1 | 5/2002 | Goetz | |
| 6,409,374 B1 * | 6/2002 | Willat | 366/130 |
| 6,467,333 B2 | 10/2002 | Lewis et al. | |
| 6,468,223 B2 | 10/2002 | Kaga | |
| 6,491,643 B2 | 12/2002 | Katzman et al. | |
| 6,528,954 B1 | 3/2003 | Lys et al. | |
| 6,544,800 B2 | 4/2003 | Asher | |
| 6,558,320 B1 | 5/2003 | Causey, III et al. | |
| 6,609,068 B2 | 8/2003 | Cranley et al. | |
| 6,623,698 B2 | 9/2003 | Kuo | |
| 6,635,452 B1 | 10/2003 | Monforte et al. | |
| 6,670,427 B1 | 12/2003 | Ulbricht et al. | |
| 6,746,529 B1 | 6/2004 | Witteveen et al. | |
| 6,753,191 B2 | 6/2004 | Asher et al. | |
| 6,754,472 B1 | 6/2004 | Williams et al. | |
| 6,797,522 B1 | 9/2004 | Still et al. | |
| 6,821,331 B2 | 11/2004 | Damodaran | |
| 6,949,347 B2 | 9/2005 | Singh et al. | |
| 6,953,589 B1 | 10/2005 | Trautman et al. | |
| 7,022,514 B2 | 4/2006 | Vodyanoy et al. | |
| 7,105,352 B2 | 9/2006 | Asher et al. | |
| 7,247,489 B2 | 7/2007 | Bakker et al. | |
| 7,288,415 B2 | 10/2007 | Huang | |
| 7,292,349 B2 | 11/2007 | Miller et al. | |
| 7,314,453 B2 | 1/2008 | Kuo | |
| 7,402,423 B2 | 7/2008 | Taghizadeh et al. | |
| 7,442,754 B2 | 10/2008 | Tepper et al. | |
| 7,459,713 B2 | 12/2008 | Coates | |
| 7,483,805 B2 | 1/2009 | Sparks et al. | |
| 7,555,437 B2 | 6/2009 | Pierce | |
| 7,563,026 B2 | 7/2009 | Mandelkern et al. | |
| 7,576,319 B2 | 8/2009 | Miller et al. | |
| 7,610,804 B2 * | 11/2009 | Ramus et al. | 73/304 R |
| 7,647,237 B2 | 1/2010 | Malave et al. | |
| 7,722,536 B2 | 5/2010 | Goodnow | |
| 7,736,310 B2 | 6/2010 | Taub | |
| 7,766,658 B2 | 8/2010 | Tricca et al. | |
| 7,813,780 B2 | 10/2010 | Shah et al. | |
| 7,860,727 B2 | 12/2010 | Showalter et al. | |
| 7,950,545 B1 * | 5/2011 | Roberts | 220/703 |
| 8,241,575 B2 * | 8/2012 | Murray et al. | 422/82.07 |
| 2002/0044891 A1 | 4/2002 | Miller et al. | |
| 2002/0127143 A1 | 9/2002 | Kuo | |
| 2003/0022225 A1 * | 1/2003 | Monforte et al. | 435/6 |
| 2003/0023189 A1 | 1/2003 | Kuo | |
| 2003/0034895 A1 * | 2/2003 | Reich | 340/618 |
| 2003/0062909 A1 * | 4/2003 | Liao | 324/693 |
| 2003/0138939 A1 | 7/2003 | Vodyanoy et al. | |
| 2003/0143580 A1 | 7/2003 | Straus | |
| 2004/0006257 A1 | 1/2004 | Burch et al. | |
| 2004/0018508 A1 | 1/2004 | Friedman | |
| 2004/0078219 A1 | 4/2004 | Kaylor et al. | |
| 2004/0100376 A1 | 5/2004 | Lye et al. | |
| 2004/0115132 A1 | 6/2004 | Young et al. | |
| 2004/0162467 A1 | 8/2004 | Cook | |
| 2005/0037112 A1 * | 2/2005 | Daley et al. | 426/104 |
| 2005/0143787 A1 | 6/2005 | Boveja et al. | |
| 2006/0033631 A1 * | 2/2006 | Cupples et al. | 340/612 |
| 2006/0204444 A1 | 9/2006 | Young et al. | |
| 2006/0292174 A1 | 12/2006 | de los Rios et al. | |
| 2007/0021458 A1 | 1/2007 | Ishikawa et al. | |
| 2007/0059245 A1 | 3/2007 | Young et al. | |
| 2007/0146154 A1 * | 6/2007 | Teller | 340/689 |
| 2007/0190084 A1 | 8/2007 | Hilt et al. | |
| 2007/0254260 A1 | 11/2007 | Alden, IV et al. | |
| 2008/0102953 A1 | 5/2008 | Schultz | |
| 2008/0175963 A1 | 7/2008 | Pope | |
| 2008/0258401 A1 * | 10/2008 | Cotton | 277/321 |
| 2008/0265146 A1 | 10/2008 | Coates | |
| 2008/0283538 A1 * | 11/2008 | Rowen | 220/739 |
| 2008/0294061 A1 | 11/2008 | Wang et al. | |
| 2008/0300569 A1 * | 12/2008 | Schateikis et al. | 604/403 |
| 2008/0303678 A1 * | 12/2008 | McCredy | 340/628 |
| 2009/0120038 A1 * | 5/2009 | Abercrombie et al. | 53/440 |
| 2009/0149988 A1 | 6/2009 | Hyde et al. | |
| 2009/0170124 A1 | 7/2009 | Campbell | |
| 2009/0247857 A1 | 10/2009 | Harper et al. | |
| 2010/0089152 A1 * | 4/2010 | Kolada et al. | 73/426 |
| 2010/0193066 A1 * | 8/2010 | Kenny | 141/1 |
| 2011/0008029 A1 * | 1/2011 | Von Seidel | 392/444 |
| 2011/0036452 A1 * | 2/2011 | Schnyder | 141/83 |
| 2011/0050431 A1 * | 3/2011 | Hood et al. | 340/603 |
| 2011/0053283 A1 * | 3/2011 | Hood et al. | 436/104 |
| 2011/0054801 A1 | 3/2011 | Hilborne et al. | |

FOREIGN PATENT DOCUMENTS

| | | |
|---|---|---|
| WO | WO 2007/113727 A2 | 10/2007 |
| WO | WO 2008/006152 A1 | 1/2008 |

OTHER PUBLICATIONS

Alexeev, Vladimir L., et al.; "Photonic Crystal Glucose-Sensing Material for Noninvasive Monitoring of Glucose in Tear Fluid"; Clinical Chemistry; Bearing a date of 2004; pp. 2353-2360; vol. 50, No. 12; American Association for Clinical Chemistry.

Asher Research Group; "Colloid Group"; Printed on Jul. 31, 2009; pp. 1-14; located at http://www.pitt.edu/~asher/homepage/colgrp.html.

Baker, Brian R., et al.; "An Electronic, Aptamer-Based Small-Molecule Sensor for the Rapid, Label-Free Detection of Cocaine in Adulterated Samples and Biological Fluids"; Journal of the American Chemical Society; Bearing a date of Feb. 18, 2006; pp. 3138-3139; vol. 128; American Chemical Society.

Baker, Monya; "From The Lab: Biotechnology; Beaming Biodata: Mutation detection goes wireless"; MIT Technology Review; Bearing a date of May 2005; pp. 1-5.

Balon, Helena R., et al.; "Society of Nuclear Medicine Procedure Guideline for C-14 Urea Breath Test"; Society of Nuclear Medicine Procedure Guidelines Manual; Bearing a date of Jun. 2002; pp. 37-39.

Bauer, Susan; "Saliva spits out information on chemical exposure"; PNNL News Release; Bearing a date of Oct. 24, 2003; Printed on Jul. 31, 2009; pp. 1-2; located at http://www.innovations-report.com/html/reports/life_sciences/report-22741.html.

Ben-Moshe, Matti, et al.; "Fast Responsive Crystalline Colloidal Array Photonic Crystal Glucose Sensors"; Analytical Chemistry; Bearing a date of Jul. 15, 2006; pp. 5149-5157; vol. 78, No. 14; American Chemical Society.

Besanger, Travis R., et al.; "Screening of Inhibitors Using Enzymes Entrapped in Sol—Gel-Derived Materials"; Analytical Chemistry; Bearing a date of May 15, 2003; pp. 2382-2391; vol. 75, No. 10; American Chemical Society.

Biohesion Incorporated; "Advanced Surface Binding Technology"; Bearing a date of 2007; p. 1 of 1; located at http://www.biohesion.com/.

(56) References Cited

OTHER PUBLICATIONS

Boisen, Anja, et al.; "Rapid molecular detection of food- and waterborne diseases"; Microbiology Today; Bearing a date of Aug. 2007; pp. 116-118.
Bromberg, Lev; "Intelligent Polyelectrolytes and Gels in Oral Drug Delivery"; Current Pharmaceutical Biotechnology; Bearing a date of 2003; pp. 339-349; vol. 4, No. 5; Bentham Science Publishers Ltd.
Bruno, John G., et al.; "Use of Magnetic Beads in Selection and Detection of Biotoxin Aptamers by Electrochemiluminescence and Enzymatic Methods"; BioTechniques; Bearing a date of Jan. 2002; pp. 178-183; vol. 32, No. 1.
Byrne, Mark E., et al.; "Molecular imprinting within hydrogels"; Advanced Drug Delivery Reviews; Bearing a date of 2002; pp. 149-161; vol. 54; Elsevier Science B.V.
Chen, Chao-Tsen, et al.; "Fluorescent, Sequence-Selective Peptide Detection by Synthetic Small Molecules"; Science; Bearing a date of Feb. 6, 1998; pp. 851-853; vol. 279.
Daunert, Sylvia, et al.; "Genetically Engineered Whole-Cell Sensing Systems: Coupling Biological Recognition with Reporter Genes"; Chemical Reviews; Bearing a date of 2000; pp. 2705-2738; vol. 100, No. 7; American Chemical Society.
Dill, Kilian, et al.; "Immunoassays and sequence-specific DNA detection on a microchip using enzyme amplified electrochemical detection"; Journal of Biochemical and Biophysical Methods; Bearing a date of 2004; pp. 181-187; vol. 59; Elsevier B.V.
Drafts, Bill; "Acoustic Wave Technology Sensors"; Sensors; Bearing a date of Oct. 1, 2000; Printed on Jul. 31, 2009; pp. 1-9; located at http://www.sensorsmag.com/articles/1000/68/main.shtml.
Drummond, T Gregory, et al.; "Electrochemical DNA sensors"; Nature Biotechnology; Bearing a date of Oct. 2003; pp. 1192-1199; vol. 21, No. 10; Nature Publishing Group.
Dwarakanath, Sulatha, et al.; "Quantum dot-antibody and aptamer conjugates shift fluorescence upon binding bacteria"; Biochemical and Biophysical Research Communications; Bearing a date of 2004; pp. 739-743; vol. 325; Elseveir Inc.
Ehrick, Jason D., et al.; "Genetically engineered protein in hydrogels tailors stimuli-responsive characteristics"; Nature Materials; Bearing a date of Apr. 2005; pp. 298-302; vol. 4; Nature Publishing Group.
Gao, Liang, et al.; "Design and Characterization of a Multisource Hand-Held Tandem Mass Spectrometer"; Analytical Chemistry; Bearing a date of Oct. 1, 2008; pp. 7198-7205; vol. 80, No. 19; American Chemical Society.
Garrison, Kenneth E., et al.; "A review of membrane sampling from biological tissues with applications in pharmacokinetics, metabolism and pharmacodynamics"; European Journal of Pharmaceutical Sciences; Bearing a date of 2002; pp. 1-12; vol. 17; Elsevier Science B.V.
Gelfand, Alexander; "Device Offers a Roadside Dope Test"; MIT Technology Review; Bearing a date of Aug. 4, 2009; pp. 1-4.
Gonzalez, Anjelica L., et al.; "Integrin Interactions with Immobilized Peptides in Polyethylene Glycol Diacrylate Hydrogels"; Tissue Engineering; Bearing a date of 2004; pp. 1775-1786; vol. 10, No. 11/12.
Hagleitner, C., et al.; "Smart single-chip gas sensor microsystem"; Nature; Bearing a date of Nov. 15, 2001; pp. 293-296; vol. 414; Macmillan Magazines Ltd.
Heim, Sarah J.; "Lab on a Swab"; MIT Technology Review; Bearing a date of Aug. 29, 2005; pp. 1-4; located at http://www.technologyreview.com/biomedicine/14709/.
Heine, R. Phillip, et al.; "Accuracy of salivary estriol testing compared to traditional risk factor assessment in predicting preterm birth"; American Journal of Obstetrics and Gynecology; Bearing a date of Jan. 1999; pp. 214S-218S; vol. 180(1S-III).
Herber, Sebastiaan, et al.; "A hydrogel-based CO2 sensor"; MESA+ Institute for Nanotechnology, University of Twente; Bearing a date of Aug. 29, 2005; Printed on Jul. 31, 2009; pp. 1-2; located at http://bios.ewi.utwente.nl/research/electrochemicalsystems/formeranalysissystemsandsensorsprojects/ahydrogelbased.doc/index.html.
Hitachi, Ltd.; "Development of world's first RFID sensor chip for DNA analysis"; Press Release; Bearing a date of Feb. 10, 2005; pp. 1-4.
Hodinka, R. L., et al.; "Detection of Human Immunodeficiency Virus Antibodies in Oral Fluids"; Clinical and Diagnostic Laboratory Immunology; Bearing a date of Jul. 1998; pp. 419-426; vol. 5, No. 4; American Society for Microbiology.
Hofman, Lindsay F.; "Human Saliva as a Diagnostic Specimen"; Journal of Nutrition; Bearing a date of 2001; pp. 1621S-1625S; vol. 131; American Society for Nutritional Sciences.
Holtz, John H., et al.; "Polymerized colloidal crystal hydrogel films as intelligent chemical sensing materials"; Nature; Bearing a date of Oct. 23, 1997; pp. 829-832; vol. 389; Macmillan Publishers Ltd.
Horner, Scott R., et al.; "A proteomic biosensor for enteropathogenic *E. coli*"; Biosensors and Bioelectronics; Bearing a date of 2006; pp. 1659-1663; vol. 21; Elsevier B.V.
Indo-Asian News Service; "Scientists develop biosensor to detect *E. Coli* bacteria"; RxPG News; Bearing dates of Feb. 25, 2006 and Aug. 19, 2006; Printed on Jul. 31, 2009; pp. 1-3; located at http://www.rxpgnews.com/article_3524.shtml.
Karjalainen, S., et al.; "Salivary Cholesterol of Healthy Adults in Relation to Serum Cholesterol Concentration and Oral Health"; Journal of Dental Research; Bearing a date of Oct. 1997; pp. 1637-1643; vol. 76, No. 10; Sage Publications.
Katagiri, Kiyofumi, et al.; "Creation of asymmetric bilayer membrane on monodispersed colloidal silica particles"; Colloids and Surfaces B: Biointerfaces; Bearing a date of 2004; pp. 149-153; vol. 38; Elsevier B.V.
Kaufman, Eliaz, et al.; "The Diagnostic Applications of Saliva—A Review"; Critical Reviews in Oral Biology & Medicine; Bearing a date of 2002; pp. 197-212; vol. 13, No. 2.
Kharitonov, Sergei A., et al.; "Exhaled Markers of Pulmonary Disease"; American Journal of Respiratory and Critical Care Medicine; Bearing a date of 2001; pp. 1693-1722; vol. 163.
Khurana, Surender, et al.; "Antigenic Fingerprinting of H5N1 Avian Influenza Using Convalescent Sera and Monoclonal Antibodies Reveals Potential Vaccine and Diagnostic Targets"; PLoS Medicine; Bearing a date of Apr. 2009; pp. 1-13; vol. 6, No. 4.
Kimo Instruments; "Hand-held carbon dioxide (CO2) analyzer, CO, CO2, °C, %HR"; Printed on Aug. 27, 2009; pp. 1; located at http://www.directindustry.com/prod/kimo/hand-held-carbon-dioxide-co2-analyzer-11846-389510.html.
Korsman, Stephen; "Chapter 6: Vaccines"; Influenza Report 2006 Edited by Kamps et al.; Bearing a date of 2006; pp. 1-4, and 127-149; Flying Publisher.
Kumar, Ashok; "Biosensors Based on Piezoelectric Crystal Detectors: Theory and Application"; JOM-e; Bearing a date of Oct. 2000; Printed on Jul. 31, 2009; pp. 1-9; vol. 52, No. 10; located at http://www.tms.org/pubs/journals/JOM/0010/Kumar/Kumar-0010.html.
Lai, Rebecca Y., et al.; "Aptamer-Based Electrochemical Detection of Picomolar Platelet-Derived Growth Factor Directly in Blood Serum"; Analytical Chemistry; Bearing a date of Jan. 1, 2007; pp. 229-233; vol. 79, No. 1; American Chemical Society.
Lai, Rebecca Y., et al.; "Differential Labeling of Closely Spaced Biosensor Electrodes via Electrochemical Lithography"; Langmuir; Bearing a date of 2006; pp. 1932-1936; vol. 22; American Chemical Society.
Lakshmi, Dhana, et al.; "Electrochemical Sensor for Catechol and Dopamine Based on a Catalytic Molecularly Imprinted Polymer-Conducting Polymer Hybrid Recognition Element"; Analytical Chemistry; Bearing a date of May 1, 2009; pp. 3576-3584; vol. 81, No. 9; American Chemical Society.
Lavigne, John J., et al.; "Solution-Based Analysis of Multiple Analytes by a Sensor Array: Toward the Development of an 'Electronic Tongue'"; Journal of the American Chemical Society; Bearing a date of Jul. 1998; pp. 6429-6430; vol. 120; American Chemical Society.
Lawrence, Herenia P.; "Salivary Markers of Systemic Disease: Noninvasive Diagnosis of Disease and Monitoring of General Health"; Journal of the Canadian Dental Association; Bearing a date of Mar. 2002; pp. 170-174; vol. 68, No. 3.
Lee, Jeong-O, et al.; "Aptamers as molecular recognition elements for electrical nanobiosensors"; Analytical and Bioanalytical Chemistry; Bearing a date of 2008; pp. 1023-1032; vol. 390; Springer-Verlag.

(56) References Cited

OTHER PUBLICATIONS

Lempert, Phil; "Digital house calls? Check your health at home"; MSNBC.com; Bearing a date of Feb. 21, 2006; p. 1 of 1; located at http://www.msnbc.msn.com/id/11476436/.
Li, Y., et al.; "The Oral Fluid MEMS/NEMS Chip (OFMNC): Diagnostic & Translational Applications"; Advances in Dental Research; Bearing a date of 2005; pp. 3-5; vol. 18; Sage.
Liu, Chung-Chiun; "Applications of Microfabrication Techniques in Electrochemical Sensor Development"; Applied Biochemistry and Biotechnology; Bearing a date of 1993; pp. 99-107; vol. 41; The Humana Press Inc.
Liu, Ke, et al.; "Detection of $Pb^{2+}$ Using a Hydrogel Swelling Microcantilever Sensor"; Analytical Sciences; Bearing a date of Jan. 2004; pp. 9-11; vol. 20; The Japan Society for Analytical Chemistry.
MiSCOPE Handheld Digital Microscope; "Description"; Forensics Source; Printed on Aug. 27, 2009; pp. 1; located at http://www.forensicssource.com/p-1810-miscope-handheld-digital-microscope.aspx .
Miyata, Takashi, et al.; "A reversibly antigen-responsive hydrogel"; Nature; Bearing a date of Jun. 24, 1999; pp. 766-769; vol. 399; Macmillan Magazines Ltd.
Miyawaki, Atsushi, et al.; "Fluorescent indicators for $Ca^{2+}$ based on green fluorescent proteins and calmodulin"; Nature; Bearing a date of Aug. 28, 1997; pp. 882-887; vol. 388; Macmillan Publishers Ltd.
Moldoveanu, Z., et al.; "Human immune responses to influenza virus vaccines administered by systemic or mucosal routes"; Vaccine; Bearing a date of 1995; pp. 1006-1012; vol. 13, No. 11; Elsevier Science Ltd.
Murthy, S. Narasimha, et al.; "Physical and Chemical Permeation Enhancers in Transdermal Delivery of Terbutaline Sulphate"; AAPS PharmSciTech; Bearing a date of 2001; pp. 1-5; vol. 2, No. 1.
Musa-Veloso, Kathy, et al.; "Breath acetone is a reliable indicator of ketosis in adults consuming ketogenic meals"; The American Journal of Clinical Nutrition; Bearing a date of 2002; pp. 65-70; vol. 76; American Society for Clinical Nutrition.
Nishanian, Parunag, et al.; "Oral Fluids as an Alternative to Serum for Measurement of Markers of Immune Activation"; Clinical and Diagnostic Laboratory Immunology; Bearing a date of Jul. 1998; pp. 507-512; vol. 5, No. 4; American Society for Microbiology.
Overhoff Technology Corporation; "All Purpose, Affordable, Beta/Gamma Meter With A Sensitivity to 1 μR/h!; Ion Ferret Gamma/Beta Detector Ionization Chamber/Survey Meter"; Printed on Aug. 27, 2009; pp. 1-2.
Pathak, C.M., et al.; "Urea Breath Test for *Helicobacter pylori* Detection: Present Status"; Tropical Gastroenterology; Bearing a date of Oct.-Dec. 2004; pp. 156-161; vol. 25, No. 4.
Peppas, Nicholas A., et al.; "Polymers and Gels as Molecular Recognition Agents"; Pharmaceutical Research; Bearing a date of May 2002; pp. 578-587; vol. 19, No. 5; Plenum Publishing Corporation.
Potter, Steve M., et al.; "A new approach to neural cell culture for long-term studies"; Journal of Neuroscience Methods; Bearing a date of 2001; pp. 17-24; vol. 110; Elsevier Science B.V.
Queyras, Armelle, et al.; "Non-invasive techniques for analysing hormonal indicators of stress"; Annali dell'Istituto Superiore di Sanita; Bearing a date of 2004; pp. 211-221; vol. 40, No. 2.
Quickmedical Medical Equipment and Supplies; "AlcoHawk CA2000—Premium Digital Alcohol Breath Analyzer"; Printed on Jul. 31, 2009; pp. 1-4; located at http://www.quickmedical.com/breathalyzer/alcoscan_tech.html.
Quickmedical Medical Equipment and Supplies; "Digital Alcohol Breathalyzer—AlcoHawk ABI Premium"; Printed on Jul. 31, 2009; pp. 1-3; located at http://www.quickmedical.com/breathalyzer/alcoscan.html.
Rädler, Ulf, et al.; "Design of Supported Membranes Tethered via Metal-Affinity Ligand-Receptor Pairs"; Biophysical Journal; Bearing a date of Dec. 2000; pp. 3144-3152; vol. 79; Biophysical Society.
Rider, Todd H., et al.; "A B Cell-Based Sensor for Rapid Identification of Pathogens"; Science; Bearing a date of Jul. 11, 2003; pp. 213-215; vol. 301.

Savran, Cagri A., et al.; "Micromechanical Detection of Proteins Using Aptamer-Based Receptor Molecules"; Analytical Chemistry; Bearing a date of Jun. 1, 2004; pp. 3194-3198; vol. 76, No. 11; American Chemical Society.
Science Daily; "Salivary Diagnostics, The 'Magic Mirror' To Your Health . . . At Your Personal Computer"; Bearing a date of Apr. 5, 2008; pp. 1-2; located at http://www.sciencedaily.com/releases/2008/04/080405095750.htm.
Şenel, Sevda, et al.; "Drug permeation enhancement via buccal route: possibilities and limitations"; Journal of Controlled Release; Bearing a date of 2001; pp. 133-144; vol. 72; Elsevier Science B.V.
Skelley, Alison M., et al.; "Development and evaluation of a microdevice for amino acid biomarker detection and analysis on Mars"; PNAS; Bearing a date of Jan. 25, 2005; pp. 1041-1046; vol. 102, No. 4; The National Academy of Sciences of the USA.
Snow, E. S., et al.; "Chemical Detection with a Single-Walled Carbon Nanotube Capacitor"; Science; Bearing a date of Mar. 25, 2005; pp. 1942-1945; vol. 307.
Sotiropoulou, Sofia, et al.; "Stabilization of enzymes in nanoporous materials for biosensor applications"; Biosensors and Bioelectronics; Bearing a date of 2005; pp. 1674-1679; vol. 20; Elsevier B.V.
SPI Pharma Group; "New Formulation Makes Gum Delivery System Efficient and Affordable"; Special Delivery: The quarterly newsletter from SPI Pharma Group; Bearing a date of Summer 2001; pp. 1-4.
Stojanovic, Milan N., et al.; "Aptamer-Based Folding Fluorescent Sensor for Cocaine"; Journal of the American Chemical Society; Bearing a date of 2001; pp. 4928-4931; vol. 123, No. 21; American Chemical Society.
Tanaka, Toyoichi, et al.; "Polymer Gels that can Recognize and Recover Molecules"; Faraday Discussions; Bearing a date of 1996; pp. 201-206; vol. 102.
Tolosa, Leah, et al.; "Lifetime-Based Sensing of Glucose Using Energy Transfer with a Long Lifetime Donor"; Analytical Biochemistry; Bearing a date of 1997; pp. 102-108; vol. 250; Academic Press.
Tombelli, Sara, et al.; "Piezoelectric biosensors: Strategies for coupling nucleic acids to piezoelectric devices"; Methods; Bearing a date of 2005; pp. 48-56; vol. 37; Elsevier Inc.
U.S. Department of Energy, Office of Environmental Management, Office of Science and Technology; "Innovative Technology Summary Report, Lumi-Scint Liquid Scintillation Counter"; Bearing a date of Jul. 2001; Four pages plus pp. 1-24.
U.S. Department of Health and Human Services, Centers for Disease Control and Prevention, National Center for Health Statistics; Table 3, Table 4 and Table V from "Summary Health Statistics for U.S. Adults: National Health Interview Survey, 2003"; Bearing a date of Jul. 2005; pp. 1-4, 20-23, and 112-113.
U.S. Department of Health and Human Services, Centers for Disease Control and Prevention, National Center for Health Statistics; Table 1 from "Summary Health Statistics for U.S. Children: National Health Interview Survey, 2003"; Bearing a date of Mar. 2005; pp. 1-4, and 8-9.
Utada, A. S., et al.; "Monodisperse Double Emulsions Generated from a Microcapillary Device"; Science; Bearing a date of Apr. 22, 2005; pp. 537-541; vol. 308.
Vamvakaki, Vicky, et al.; "Fluorescence detection of enzymatic activity within a liposome based nano-biosensor"; Biosensors and Bioelectronics; Bearing a date of 2005; pp. 384-388; vol. 21; Elsevier B.V.
Vass, Géza, et al.; "Comparison of Nasal and Oral Inhalation during Exhaled Breath Condensate Collection"; American Journal of Respiratory and Critical Care Medicine; Bearing a date of 2003; pp. 850-855; vol. 167.
Vital Sensors Technologies LLC; "VS-1000B Series Inline Brix Sensors for the Beverage Industry; Inline Networked Smart Infrared Sensors for Real-Time Process Monitoring: Continuous Accurate Brix measurement of Regular and Diet Beverages"; Bearing a date of 2008; pp. 1-4.
Walker, Richard F., et al.; "Radioimmunoassay of Progesterone in Saliva: Application to the Assessment of Ovarian Function"; Clinical Chemistry; Bearing a date of 1979; pp. 2030-2033; vol. 25, No. 12.

(56) References Cited

OTHER PUBLICATIONS

Wee, Kyung Wook, et al.; "Novel electrical detection of label-free disease marker proteins using piezoresistive self-sensing micro-cantilevers"; Biosensors and Bioelectronics; Bearing a date of 2005; pp. 1932-1938; vol. 20; Elsevier B.V.
Wikipedia; "Taste"; Bearing a date of May 19, 2009; Printed on May 22, 2009; pp. 1-10; located at http://en.wikipedia.org/wiki/Taste.
Win, Maung Nyan, et al.; "Codeine-binding RNA aptamers and rapid determination of their binding constants using a direct coupling surface plasmon resonance assay"; Nucleic Acids Research; Bearing a date of 2006; pp. 5670-5682; vol. 34, No. 19.
Wong, David T.; "Oral Fluid NanoSensor Test (OFNASET)"; Bearing a date of Sep. 1, 2006; located at http://www.researchgrantdatabase.com/g/5U01DE017790-03/Oral-Fluid-NanoSensor-Test-OFNASET/ [Abstract Only].
Wong, David T.; "Salivary diagnostics powered by nanotechnologies, proteomics and genomics"; Journal of the American Dental Association; Bearing a date of 2006; pp. 313-321; vol. 137; American Dental Association.
Yazawa, Yoshiaki, et al.; "A Wireless Biosensing Chip for DNA Detection"; 2005 IEEE International Solid-State Circuits Conference, Session 30, Displays and Biosensors, 30.6; Bearing a date of 2005; pp. 562-563, and 617.
Ye, Lei, et al.; "Molecularly imprinted polymers as antibody and receptor mimics for assays, sensors and drug discovery"; Analytical and Bioanalytical Chemistry; Bearing a date of 2004; pp. 1887-1897; vol. 378.
Yoon, Min-Sung, et al.; "Characterisation of advanced glycation endproducts in saliva from patients with diabetes mellitus"; Biochemical and Biophysical Research Communications; Bearing a date of 2004; pp. 377-381; vol. 323; Elsevier Inc.
Yusa, Go, et al.; "Controlled multiple quantum coherences of nuclear spins in a nanometre-scale device"; Nature; Bearing a date of Apr. 21, 2005; pp. 1001-1005; vol. 434; Nature Publishing Group.
Balmaseda, Angel, et al.; "Diagnosis of Dengue Virus Infection by Detection of Specific Immunoglobulin M (IgM) and IgA Antibodies in Serum and Saliva"; Clinical and Diagnostic Laboratory Immunology; Bearing a date of Mar. 2003; pp. 317-322; vol. 10, No. 2; American Society for Microbiology.
U.S. Appl. No. 12/657,166, Hood et al.
U.S. Appl. No. 12/584,055, Hood et al.
U.S. Appl. No. 12/584,054, Hood et al.
Barnes, Allan J., et al.; "Excretion of Methamphetamine and Amphetamine in Human Sweat Following Controlled Oral Methamphetamine Administration"; Clinical Chemistry; Bearing a date of 2008; pp. 172-180; vol. 54, No. 1; American Society for Clinical Chemistry.
Beck, M., et al.; "Nanoelectrochemical transducers for (bio-) chemical sensor applications fabricated by nanoimprint lithography"; Microelectronic Engineering; Bearing a date of 2004; pp. 837-842; vol. 73-74; Elsevier B.V.
Cramer, Joyce A., et al.; "Compliance With Medication Regimens for Mental and Physical Disorders"; Psychiatric Services; Bearing a date of Feb. 1998; pp. 196-201; vol. 49; American Psychiatric Association.
Davis, Mark D.P., et al.; "Thermoregulatory Sweat Testing in Patients With Erythromelalgia"; Archives of Dermatology; Bearing a date of Dec. 2006; pp. 1583-1588; vol. 142; American Medical Association; located at www.archdermatol.com.
Hemmingsson, Tryggve, et al.; "Novel Hand-Held Device for Exhaled Nitric Oxide-Analysis in Research and Clinical Applications"; Journal of Clinical Monitoring and Computing; Bearing a date of 2004; pp. 379-387; vol. 18; Springer 2005.
Huestis, Marilyn A., et al.; "Excretion of $\Delta^9$-Tetrahydrocannabinol in Sweat"; Forensic Science International; Bearing a date of Jan. 30, 2008; pp. 173-177 (pp. 1-10); vol. 174(2-3); National Institutes of Health.
Illigens, Ben M.W., et al.; "Sweat testing to evaluate autonomic function"; Clinical Autonomic Research; Bearing a date of Nov. 6, 2008; pp. 79-87; vol. 19.
Kintz, Pascal, et al.; "Sweat testing for heroin and metabolites in a heroin maintenance program"; Clinical Chemistry; Bearing a date of 1997; pp. 736-739; vol. 43, No. 5.
Knott, Christine, et al.; "Phenytoin-valproate interaction: importance of saliva monitoring in epilepsy"; British Medical Journal; Bearing a date of Jan. 2, 1982; pp. 13-16; vol. 284.
Kovacs, Eva M.R., et al.; "Effect of caffeinated drinks on substrate metabolism, caffeine excretion, and performance"; Journal of Applied Physiology; Bearing a date of 1998; pp. 709-715; vol. 85; American Physiological Society.
Lavrik, Nickolay V., et al.; "Cantilever transducers as a platform for chemical and biological sensors"; Review of Scientific Instruments; Bearing a date of Jul. 2004; pp. 2229-2253; vol. 75, No. 7; American Institute of Physics.
Mezzasoma, Letizia, et al.; "Antigen Microarrays for Serodiagnosis of Infectious Diseases"; Clinical Chemistry; Bearing a date of 2002; pp. 121-130; vol. 48, No. 1; American Association of Clinical Chemistry.
Mitchell, Alex J., et al.; "Why don't patients take their medicine? Reasons and solutions in psychiatry"; Advances in Psychiatric Treatment; Bearing a date of 2007; pp. 336-346; vol. 13.
Patel, Nilay; "Nintendo Wii Vitality Sensor detects your pulse"; Engadget; Bearing a date of Jun. 2, 2009; Printed on Jan. 8, 2010; pp. 1-24; located at: http://www.engadget.com/2009/06/02/nintendo-wii-vitality-sensor-detects-your-pulse/.
Phillips, Michael; "Sweat-Patch Test for Alcohol Consumption: Rapid Assay with an Electrochemical Detector"; Alcoholism: Clinical and Experimental Research; Bearing a date of Fall 1982; pp. 532-534; vol. 6, No. 4; The American Medical Society on Alcoholism, The Research Society on Alcoholism, and the National Council on Alcoholism.
Potyrailo, Radislav A., et al.; "Chemical Sensors Based on Micromachined Transducers with Integrated Piezoresistive Readout"; Analytical Chemistry; Bearing a date of Aug. 15, 2006; pp. 5633-5638; vol. 78, No. 16; American Chemical Society.
Robroeks, C.M.H.H.T., et al.; "Exhaled nitric oxide and biomarkers in exhaled breath condensate indicate the presence, severity and control of childhood asthma"; Clinical and Experimental Allergy; Bearing a date of 2007; pp. 1303-1311; vol. 37; Blackwell Publishing Ltd.
Schena, Mark, et al.; "Quantitative Monitoring of Gene Expression Patterns with a Complementary DNA Microarray"; Science; Bearing a date of Oct. 20, 1995; pp. 467-470; vol. 270.
Smith, Andrew D., et al.; "Use of Exhaled Nitric Oxide Measurements to Guide Treatment in Chronic Asthma"; The New England Journal of Medicine; Bearing a date of May 26, 2005; pp. 2163-2173; vol. 352, No. 21; Massachusetts Medical Society.
Tang, Dianping, et al.; "Magnetic Control of an Electrochemical Microfluidic Device with an Arrayed Immunosensor for Simultaneous Multiple Immunoassays"; Clinical Chemistry; Bearing a date of 2007; pp. 1323-1329; vol. 53, No. 7; American Association for Clinical Chemistry.
Thieme, Thomas, et al.; "Determination of Measles, Mumps, and Rubella Immunization Status Using Oral Fluid Samples"; JAMA; Bearing a date of Jul. 20, 1994; pp. 219-221; vol. 272, No. 3.
Uchida, Hideaki, et al.; "A New Assay Using Surface Plasmon Resonance (SPR) to Determine Binding of the *Lactobacillus acidophilus* Group to Human Colonic Mucin"; Bioscience, Biotechnology, and Biochemistry; Bearing a date of 2004; pp. 1004-1010; vol. 68, No. 5.

\* cited by examiner

FIG. 2
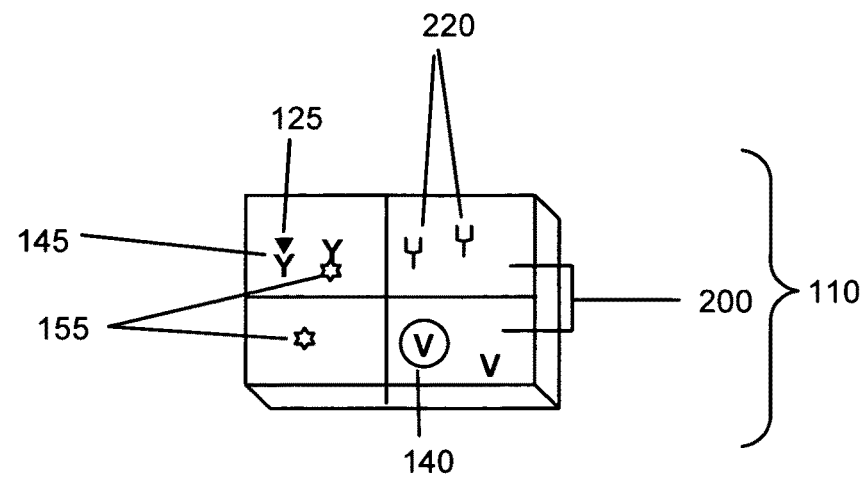
Fig. 2A
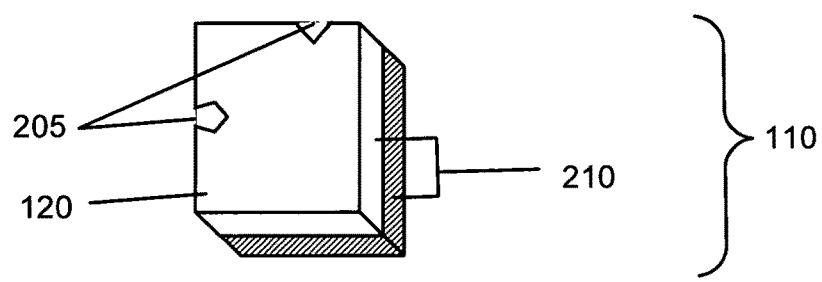
Fig. 2B

FIG. 4
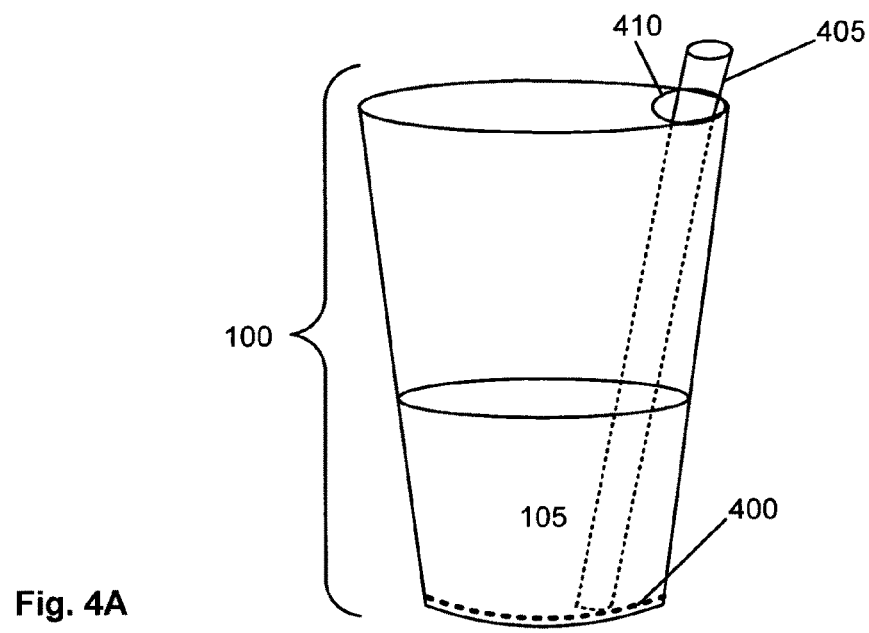
Fig. 4A
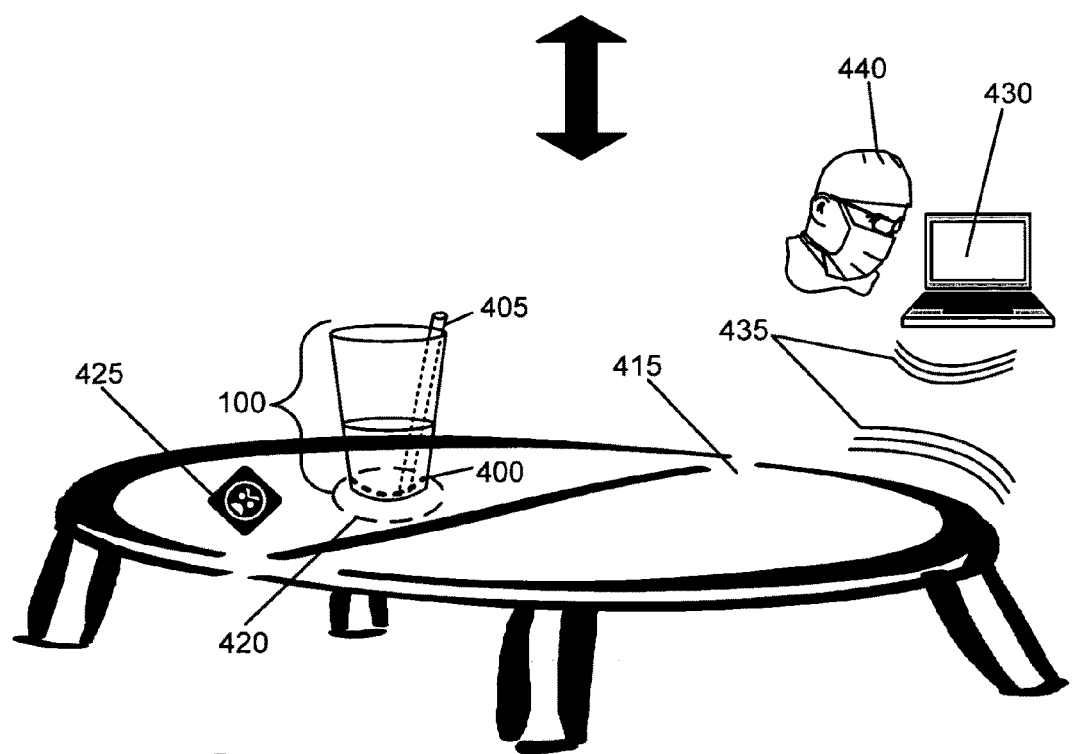
Fig. 4B

FIG. 11
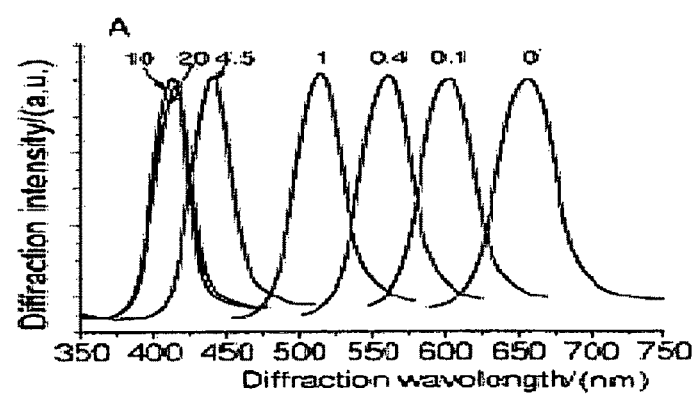
Fig. 11A
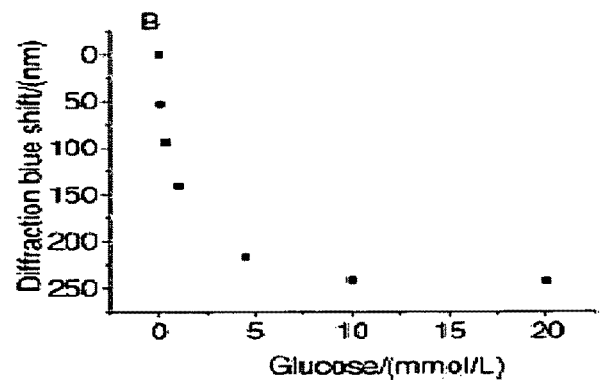
Fig. 11B

FIG. 14
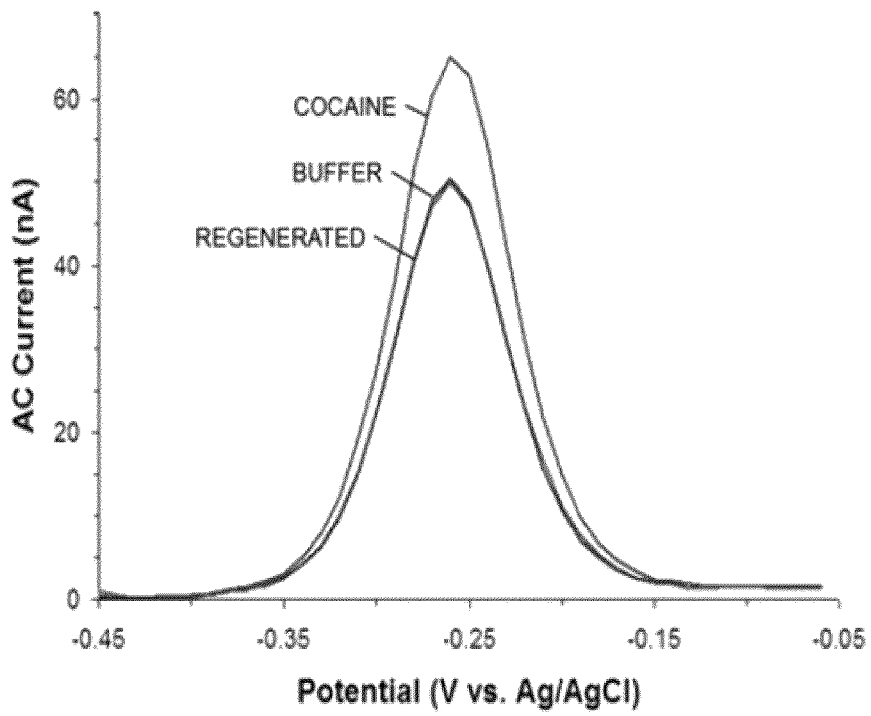
Fig. 14A
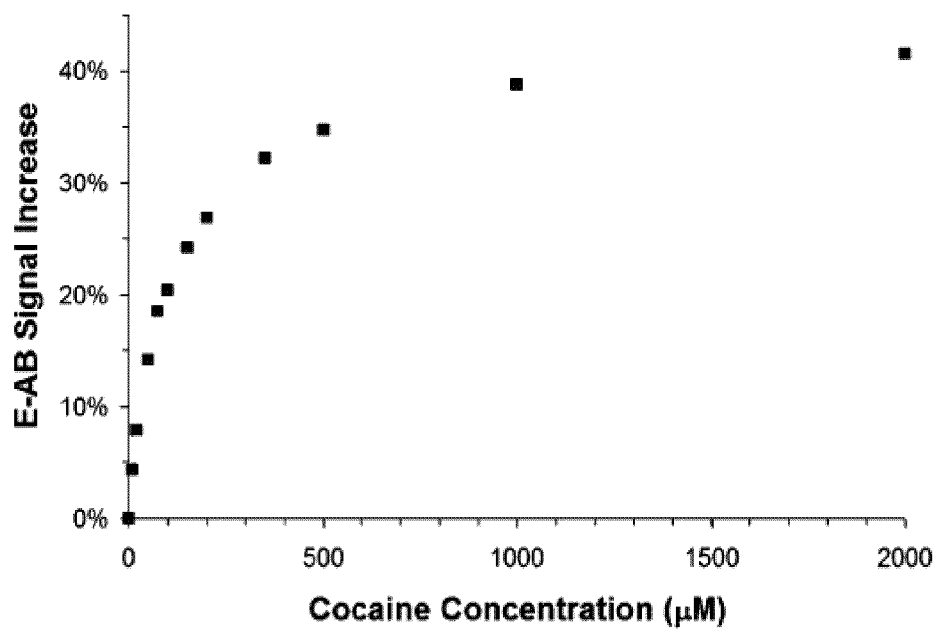
Fig. 14B

BEVERAGE CONTAINERS WITH DETECTION CAPABILITY

RELATED APPLICATIONS

For purposes of the USPTO extra-statutory requirements, the present application constitutes a continuation-in-part of U.S. patent application Ser. No. 12/584,055, entitled DEVICES AND METHODS FOR DETECTING AN ANALYTE IN SALIVARY FLUID, naming Leroy E. Hood, Edward K. Y. Jung, Elizabeth A. Sweeney, Clarence T. Tegreene, and Lowell L. Wood, Jr. as inventors, filed Aug. 28, 2009 now U.S. Pat. No. 8,898,069, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/584,054, entitled BEVERAGE IMMERSATE WITH DETECTION CAPABILITY, naming Leroy E. Hood, Edward K. Y. Jung, Elizabeth A. Sweeney, Clarence T. Tegreene, and Lowell L. Wood, Jr. as inventors, filed Aug. 28, 2009 now U.S. Pat. No. 8,810,417, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In one aspect, a system includes, but is not limited to, a beverage container including a vessel body configured to hold a beverage, and at least one sensor associated with the vessel body, the at least one sensor including a sensor configured to detect one or more substance in a fluid. In one aspect, a system includes, but is not limited to, at least one beverage container including at least one sensor configured to detect one or more substance in fluid, and at least one external device including at least one port configured for communication with the at least one sensor. In addition to the foregoing, other system aspects are described in the claims, drawings, and text forming a part of the present disclosure.

In one aspect, a method includes, but is not limited to, a method of detecting one or more substance in fluid, including detecting one or more substance within fluid with at least one sensor integral to a beverage container, and interfacing one or more of the at least one sensor with an external device. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 2A is a schematic of some embodiments of modules of a beverage container.

FIG. 2B is a schematic of some embodiments of modules of a beverage container.

FIG. 4A is a schematic of a beverage container.

FIG. 4B illustrates a beverage container system.

FIG. 11A shows diffraction intensity versus diffraction wavelength for different concentrations of glucose in a glucose-responsive PCCA sensor.

FIG. 11B illustrates the effect of glucose concentration on diffraction of a glucose-responsive PCCA sensor.

FIG. 14A shows AC voltammograms of a cocaine-responsive electronic aptamer sensor.

FIG. 14B depicts dose-response of an electronic aptamer sensor to cocaine.

DETAILED DESCRIPTION

Figure 1:
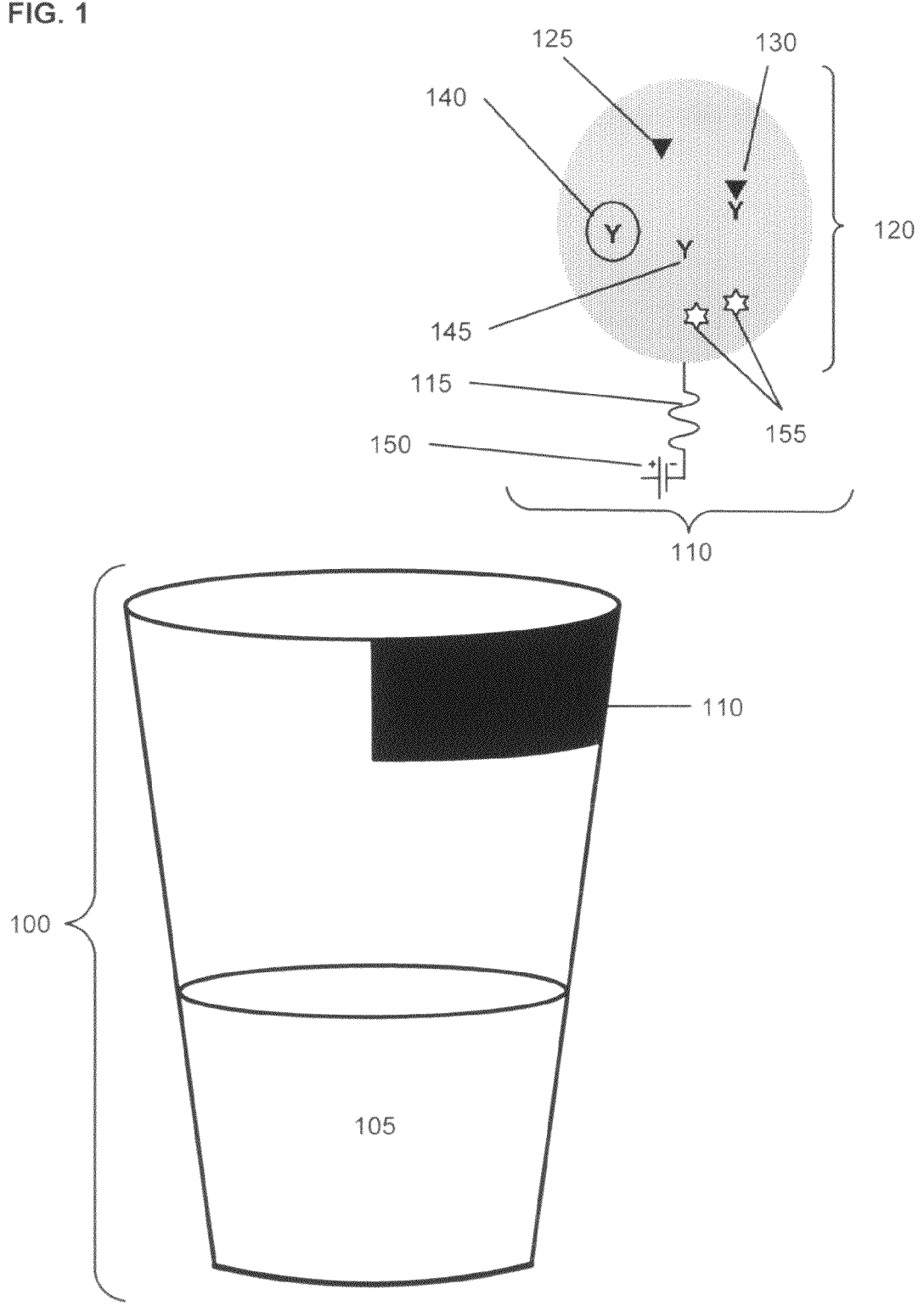
FIG. 1 is a schematic of a beverage container.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

With reference now to FIG. 1, shown is an example of an individual-use beverage container 100 that may serve as a context for introducing one or more processes and/or devices described herein. The use of the same symbols in different drawings typically indicates similar or identical items. A beverage container 100 includes a vessel body configured to hold a beverage 105, and at least one sensor 110 associated with the vessel body, the at least one sensor including a sensor configured to detect one or more substance in a fluid. The one or more substance may include at least one biological analyte. Although a beverage container 100 configured as a glass is depicted in FIG. 1, the beverage container 100 may include any vessel configured to hold a beverage for drinking by an individual. A beverage container 100 broadly includes any individual-use drinking vessel configured for personal use. A "beverage container" or an "individual use drinking vessel" as used herein refers to a beverage container 100 configured for use by a single individual for their personal beverage consumption. A beverage container 100 includes any individual-use drinking vessel configured for an individual to swallow fluid from the drinking vessel. For example, a beverage container 100 includes a container configured for a person to place their mouth on the container and take fluid from the container into the individual's oral cavity. A beverage container 100 includes any individual-use drinking vessel configured for an individual to imbibe a beverage. For example, in some embodiments the beverage container 100 may be a cup, mug, glass, thermos, bottle, carton or can configured for individual use and beverage consumption by an individual person. For example, in some embodiments the beverage container 100 may be a bowl, bottle, trough, carton or can configured for individual use and beverage consumption by an individual animal, such as a domesticated dog, cat, cow or sheep. A beverage container 100 includes a "vessel body," which as used herein refers to the structural elements of the beverage container 100. For example, a beverage container 100 may, depending on the embodiment, include a vessel body including one or more walls, one or more sides, one or more bases, one or more vessel bottoms, one or more vessel tops, one or more stems, or one or more handles.

In some embodiments, the beverage container 100 may include at least one attached straw or other drinking enhancement attachment. The beverage container 100 may include a lid or cover, which may include a specific region configured for drinking. A lid or cover may entirely or partially cover an opening of the drinking vessel. A beverage container 100 may include one or more discrete regions configured for drinking. A beverage container 100 may include one or more discrete regions configured to facilitate consumption of a beverage by an individual user. The beverage container 100 may be disposable. The beverage container 100 may be reusable, such as with modular components that are replaceable, rechargeable, swappable, or exchangeable. A beverage container 100 may include modules, for example modular units within a sensor or within a vessel wall. A beverage container 100 may include one or more handles or handgrip regions. A beverage container 100 may include materials such as absorbent, adsorbent, proteoglycan, charged polymer, polylysine, silica gel, alumina gel, and ion exchange resin. A beverage container 100 may contain regions configured from, for example, metal, glass, plastic, or polymers. A beverage container 100 may contain insulation or regions configured to control the temperature of a beverage. For example, a beverage container 100 may include insulated regions designed to keep interior fluids warm or cold. For example, a beverage container 100 may include air vents to allow steam to escape or a beverage to cool slowly. For example, a beverage container 100 may include one or more regions, which may be modular and replaceable, of refrigerant configured to cool the fluid enclosed in the beverage container 100. A beverage container 100 may include electronic or digital components. For example, a beverage container 100 may include electronic or digital components within the walls of the container or operably attached to the exterior of the container. A beverage container 100 may include for example, a handle, cover, lid or sleeve, and these parts of the beverage container 100 may include one or more electronic or digital components. A beverage container 100 may contain a heating or cooling element.

Although a human user is envisioned, it is also envisioned that the systems and methods described herein may be utilized with other animals, for example domesticated animals such as canines, felines, bovines, or equines. For example, the beverage container 100 depicted herein may be configured for drinking by a domestic house cat or a domestic dog, for example in a water dish. For example, the beverage container 100 depicted herein may be configured for drinking by a goat, sheep or cow, for example a bottle with an attached straw or hose configured for drinking. Systems and methods such as those described herein may be used to monitor the health and well-being of domestic animals, such as through the analysis of stress hormones present in salivary fluids. See, for example, Queyras and Carosi, "Non-invasive techniques for analyzing hormonal indicators of stress," *Ann 1st Super Sanita*, 40(2): 211-221 (2004), which is incorporated herein by reference.

A "beverage," as used herein, may include any fluid generally prepared, purified or processed with a goal of consumption by an individual user through drinking. An "individual user," as used herein, includes an individual human user as well as an individual domesticated animal, for example an individual dog, cat, cow or sheep. For example, a beverage may include water, juices, dairy products, alcoholic beverages, chemical compositions, and other fluids as well as mixtures of these drinks. A beverage may include a substantial nutritional component, such as a soup, broth, consommé, yogurt, buttermilk or milkshake. A beverage may include sugar-based sweeteners, such as glucose, as well as non sugar-based sweeteners such as aspartame, saccharin, sucralose, or stevioside. A beverage may contain non-fluid particulates such as undissolved material, contaminants, or food additives such as those based on agar, tapioca or gelatin. A beverage fluid may be at any temperature appropriate for drinking. For example, a cold drink may be in the temperature range of 1-10° C. For example, a warm drink may be in the temperature range 25-35° C. For example, a hot drink may be in the temperature range 65-75° C.

A beverage container 100 includes at least one sensor 110 associated with the vessel body, the at least one sensor 110 configured to detect one or more substance in fluid. The at least one sensor 110, including a sensor 110 configured to detect one or more substance in a fluid and associated with the beverage container 100, such as within the vessel body, is depicted in FIG. 1 as a section of the rim or lip of a beverage container 100 at the top edge of the vessel walls. As depicted in FIG. 1, in some embodiments the sensor 110 may be coextensive with the vessel body, such as when the sensor 110 is embedded or attached in parallel with the walls or base of the vessel. Although the sensor 110 is depicted in FIG. 1 as a rim or edge of a glass designed for single-person use, in some embodiments the sensor 110 may be present in or on other parts of the vessel body, including a side, lid, attached straw, top, bottom, or side region. In some embodiments, a sensor 110 may be located around the entire top edge of a drinking vessel wall. In some embodiments, a sensor 110 may be located in the base or bottom of the drinking vessel. A beverage container 100 may include one or more discrete regions configured for drinking, and these regions may include sensors. In some embodiments a sensor 110 may be located in a specific region of a beverage container 100, such as a portion of an edge or side of a vessel wall. Such a region may be further delineated, marked or defined on the beverage container 100, such as through color, shape, or texture. For example, there may be a sensor 110 located in one region of a drinking vessel wall, and that region may be colored green to indicate that an individual user of the container should drink in that region to ensure maximum response of the sensor 110. For example, there may be a sensor 110 located in one region of a drinking vessel wall, and that region may be shaped to encourage an individual user to drink from that region, such as a region configured with a curved or smoothened edge to encourage sipping a beverage from that area. For example, there may be a lid or cover on the beverage container 100 and the sensor 110 region located near a drinking aperture in the lid or cover. Similarly, other regions of the vessel walls that do not include a sensor 110 may be indicated through color, shape, or texture. For example, regions of a drinking vessel wall may be configured to be rough or curved in a manner that would discourage an individual user from drinking in that region. For example, regions of a drinking vessel wall may be colored or marked as not containing a sensor 110. In some embodiments, the sensor 110 may be included in a cover or lid containing a specific drinking region, or a cover or lid may be configured to direct an individual user to drink in a region containing a sensor 110. In some embodiments a sensor 110 may be included with a drinking enhancement device, such as a drinking straw or vessel cover that encourages an individual user to place his or her mouth in a specific region and is configured to focus beverage fluid through an area, such as an area adjacent to a region including a sensor 110. Although direct or proximal contact of an individual user's mouth with a sensor 110 while drinking is not envisioned as strictly necessary, in some embodiments direct contact may enhance sensitivity or specificity of the system.

The beverage container 100 may be customized for an individual user, such as through modular units, and a substance may be specifically of interest to that individual user or a group of similar individual users. For example, a diabetic individual may be specifically concerned about glucose, sugars generally, carbohydrates, or related substances. For example, a person with allergies may be concerned about the presence of specific allergenic substances. For example, an individual following an organic diet may be concerned about pesticide or herbicide residues. For example, a person scheduled to ingest a particular medicinal agent may wish to confirm that the medicinal agent is present in the beverage fluid. For example, a person on a particular medical regimen may wish to confirm that no contraindicated substances are present in the beverage fluid before drinking. For example, grapefruit juice is contraindicated for people prescribed a number of medications, including amiodarone, buspirone, carbamezapine, cyclosporine, felodipine, saquinavir, simvastin and lovastatin. A beverage container 100 may be customized or personalized for an individual user or a group of users through the inclusion of specific modular units, such as sensor units configured to detect specific substances, which may originate with beverage fluid or salivary fluid. A beverage container 100 may be marked as customized, such as through coloring, logos, writing or pictures associated with particular sensors.

In some embodiments, the beverage container 100 might include one or more minimally or non-invasive means of enhancing transfer across the mucosa of transudate, exudate or components thereof, such as proteins, peptides, glucose, or other biological analytes. For example, the beverage container 100 may include a transmucosal sampling mechanism. A transmucosal sampling mechanism may be configured in a portion of the beverage container 100 configured for drinking, such as a specific region of the edge of a beverage container 100 vessel wall, lid or drinking straw. A transmucosal sampling mechanism may be configured in a portion of the beverage container 100 configured to come in contact with a user's lip. In one example, one or more chemical permeation enhancer such as isopropyl myristate, bile salts, surfactants, fatty acids and derivatives, chelators, cyclodextrins or chitosan might be included in a coating of a drinking region, including on one or more of the vessel walls, in a lid or on a straw. For example, see Murthy et al., "Physical and Chemical Permeation Enhancers in Transdermal Delivery of Terbutaline Sulphate," *AAPS PharmSciTech.* 2(1), Technical Note1, (2001) and Senel and Hincal, "Drug permeation enhancement via buccal route: possibilities and limitations," *J Control Release* 72(1-3): 133-144 (2001), which are herein incorporated by reference. For example, a beverage container 100 might include an ultrasonic component in an outer shell or in an outer layer of the sensor 110, or in a region distinct from the sensor 110. See, for example, US Patent Application No. 2004/0162467 to Cook, titled "Non-invasive transudate extraction," which is herein incorporated by reference. As an example, a beverage container 100 may be configured to include microprotrusions such as microneedles or microfine lances. See, for example, U.S. Pat. No. 6,953,589 to Trautman et al., titled "Device for enhancing transdermal agent flux," which is herein incorporated by reference. Other technologies that might be useful in such embodiments include, but are not limited to, iontophoresis, microdialysis, ultrafiltration, electromagnetic, osmotic, electroosmosis, sonophoresis, microdialysis, suction, electroporation, thermal poration, microporation, microfine cannulas, skin permeabilization, or a laser.

A sensor 110 associated with the vessel body of a beverage container 100 includes a sensor 110 configured to detect one or more substance 125 in a fluid. The sensor 110 may be configured to detect at least one substance in beverage fluid, salivary fluid, or a mixture of these fluids. The sensor 110 may be configured to detect one or more biological analyte. A substance may include one or more biological analyte. For example, the substance 125 may include at least one biological marker, antibody, polypeptide, protein, complex, nucleic acid, cell, pathogen, lipid, alcohol, sterol, carbohydrate, metal, electrolyte, metabolite, organic compound, organophosphate, drug, therapeutic, gas, pollutant or taggant. A substance 125 may include a biological analyte, or a metabolite of an biological analyte. For example, a substance may include a biological analyte originating from the oral cavity of an individual user. For example, a substance may include one or more bacteria or bacterial components, mucin, nucleic acid, or antibodies originating from the oral cavity of an individual user.

In some embodiments, a sensor 110 is configured to detect at least one substance, which may be a biological analyte, in salivary fluid. As used herein, "salivary fluid" includes fluids routinely found in the oral cavity of an individual user, for example blood, breath condensate, oral gas, crevicular fluid, transudate, exudate, gingival crevicular fluid, mucosal transudate or exudate, ingested remnants and mucus. For example, a sensor 110 may be located on a region of an individual-use drinking vessel configured or marked for drinking, and therefore come into direct contact with a individual user's mouth and associated salivary fluids while an individual user is drinking from the vessel. For example, a sensor 110 may be configured to specifically identify a biological analyte found in salivary fluid, such as compounds associated with the mouth and mucous membranes, such as immunoglobulin A (IgA). A biological analyte may include an indicator of a physiological state, such as a disease state. In addition other biological analytes can be present in salivary fluid at detectable levels, including markers of disease, drugs and alcohol. For example, salivary fluid has been used as a medium for the detection of HIV antibodies. See Hodinka et al., "Minireview: Detection of Human Immunodeficiency Virus antibodies in oral fluids," *Clin. & Diagn. Lab Immun.*, 5(4): 419-426 (1998), and Nishanian et al., "Oral fluids as an alternative to serum for measurement of markers of immune activation," *Clin. & Diagn. Lab Immun.*, 5(4): 507-512 (1998), which are herein incorporated by reference. For example, it is possible to correlate the concentration of alcohol in exhaled breath with blood alcohol concentration. See, for example, the sheet titled "Scientific Method and Technology" under the header "Premium Digital Alcohol Breath Analyzer—Technology" regarding the AlcoHawk CA2000 and the AlcoHawk ABI Premium from Quick Medical, which is incorporated herein by reference. Markers related to systemic health have also been measured in salivary fluids as an alternative source to serum. Hormones, antibodies, electrolytes, and cholesterol are just a few of the biological analytes that can be monitored in salivary fluids. See, for example: Hofman, "Human saliva as a diagnostic specimen," *J. Nutr.*, 131: 1621S-1625S (2001); the "Oral Fluid NanoSensor Test" sheet; Karjalainen et al., "Salivary cholesterol of healthy adults in relation to serum cholesterol concentration and oral health," *J. Dent. Res.* 76: 1637-1643 (1997); and Queuras and Carosi, "Non-invasive techniques for analyzing hormonal indicators of stress," *Ann 1st Super Sanita,* 40(2): 211-221 (2004), which are incorporated herein by reference. Studies have also shown that markers of environmental chemical exposure are detectable in salivary fluids. See for example, Bauer "Saliva spits out information on chemical exposure," PNNL news release, 2003, which is herein incorporated by reference. Some biological analytes in salivary fluids arise from gingival crevicular fluids, transudates or exudates.

In the context of a beverage container 100 configured for use in drinking by an individual, salivary fluid may include beverage fluid, and beverage fluid may include salivary fluid. A fluid includes a beverage fluid, which includes the constituent fluid of a beverage. A fluid includes salivary fluid. During the act of drinking, a beverage fluid and salivary fluid often become mixed in an individual's oral cavity and adjacent areas so that the fluid in a personal use beverage container 100 may contain a mixture of fluids originally arising from the individual user's oral cavity and the beverage fluid itself. Drinking, as used herein, may include sipping, gulping, swishing fluid in an oral cavity, or other ways to ingest fluid through an oral cavity. For example, during an act of drinking, salivary fluid and beverage fluid may mix in or in the vicinity of an individual's mouth and be transmitted into or onto a drinking vessel. For example, during an act of drinking, salivary fluid and beverage fluid may mix along the edge or in the bottom of a beverage container 100. For example, during an act of drinking, salivary fluid and beverage fluid may mix along the edge or in the bottom of a region configured for contact with an individual user's mouth, for example a straw or lid. Depending on the embodiment, it may therefore be desirable to locate a sensor 110 in a region of a beverage container 100 where salivary fluid would be likely to be present. For example, it may be desirable to configure the beverage container 100 so that the sensor 110 is in a region distinct from where an individual user would place his or her mouth. Depending on the embodiment, it may therefore be desirable to locate a sensor 110 in a region of a beverage container 100 where salivary fluid would be unlikely to be present. For example, it may be desirable to configure the beverage container 100 so that the sensor 110 is in a region that will come into contact with an individual user's mouth.

Saliva and related fluids can provide a noninvasive source for biomarkers of systemic and local diseases and disorders. In addition to providing a copious supply of saliva, the mouth can act as an access point to the gut, respiratory, and circulatory systems. In some individuals, such as children and the infirm, salivary fluids may be preferable to samples taken invasively. See, for example, European Patent Application No. EP 1 397 997 to Gröschl and Rauh titled "Detection device," and U.S. Pat. No. 6,022,326 to Tatum et al., titled "Device and method for automatic collection of whole saliva," which are herein incorporated by reference. Studies illustrate the numbers and varieties of substances that are available for testing in salivary fluids. See, for example: Kaufman and Lamster, "The Diagnostic Applications of Saliva—A Review", *Crit Rev Oral Biol Med,* 13(2):197-212 (2002); Lawrence, "Salivary markers of systemic disease: noninvasive diagnosis of disease and monitoring of general health," *J. Can. Dent. Assoc.* 68(3): 170-174 (2002); Li et al., "The oral fluid MEMS/NEMS chip (OFMNC): diagnostic and translational applications," *Adv. Dent. Res.,* 18: 3-5 (2005); "Salivary diagnostics, the 'magic mirror' to your health . . . at your personal computer," *ScienceDaily*, Apr. 5, 2008; and Wong, "Salivary Diagnostics Powered by Nanotechnologies, Proteomics and Genomics,"*J Am Dent Assoc.,* 137:313-321 (2006) which are herein incorporated by reference. Some biological analytes in the salivary fluids arise from gingival crevicular fluids, transudates or exudates. In addition, the oral mucosa is highly vascularised, which has led to the use of transmucosal access to the circulatory system.

The oral cavity is also directly connected to the digestive tract. This has allowed testing for stomach disorders, including the presence of *Helicobacter pylori* (*H. pylori*), a causal agent in stomach ulcers, in salivary fluids. The DNA of *H. pylori* can be isolated from salivary fluids taken from infected individuals. Additionally, under the right conditions, urea released by the pathogen can be measured in oral gases (see, for example, "Urea breath test for *Helicobacter pylori* detection: present status," Pathak, Bhasin and Khanduja, *Trop Gastroenterol.* October-December; 25(4):156-61 (2004), which is herein incorporated by reference). Oral gases and condensates in salivary fluid also provide a means of sampling lung exhalations to investigate pulmonary or systemic diseases. Nitric oxide, carbon monoxide, other volatile gases, as well as lipids, leukotrienes and eicosanoids are a few detectable markers of pulmonary diseases in oral samples (see, for example, "Exhaled Markers of Pulmonary Disease," Kharitonov and Barnes, *Am J Respir Crit Care Med,* 163: 1693-1722, (2001), which is herein incorporated by reference). Respiratory diseases continue to be a major cause of morbidity and mortality throughout the world. In 2003, asthma alone affected 20.7 million American adults, or 9.7% of the total adult population (see, for example, Tables 3 and 4 as well as Appendix III, table V in the Summary Health Statistics for U.S. adults: National Health Interview Survey, 2003, published by the CDC) and 9.1 million children (12%; see, for example, Table 1 in the Summary Health Statistics for U.S. Children: National Health Interview Survey, 2003.)

In some embodiments, a sensor 110 is configured to detect at least one substance 125 in beverage fluid 105. For example, a sensor 110 may be configured to detect at least one component of the beverage, such as an alcohol, protein, medicinal agent, nutraceutical, molecule, nucleic acid, pathogen, macromolecule, allergen, or contaminant. For example, a sensor 110 may be configured to detect at least one substance originating from beverage fluid that is present in the beverage before drinking by an individual user, such as alcohol, glucose, or saccharin. The sensor 110 may be configured to detect at least one contaminant in the beverage fluid, for example at least one pesticide, pathogen, macromolecule, herbicide, xenobiotic, hormone, or antibiotic. For example, a sensor 110 may be configured to detect an allergen. For example, a sensor 110 may be configured to detect at least one substance originating from salivary fluid that is present in the beverage after admixture during drinking by an individual user. For example, a sensor 110 may be configured to detect at least one substance originating from a residue or remnant on the inner surface of the beverage vessel, such as a biofilm formed from bacterial contamination or chemical residue originating from material such as cleaning solution. For example, a sensor 110 may be configured to detect at least one substance originating from salivary fluid that has mixed with beverage fluid during drinking by an individual. For example, a sensor 110 may be configured to detect at least one substance in salivary fluid, such as a sensor 110 configured to come in contact with salivary fluid directly during drinking of a beverage by an individual user.

In reference to FIG. 1, a beverage container 100 including a vessel body includes at least one sensor 110. The one or more sensor 110 may be configured to detect one or more substance. The one or more sensor 110 may be configured to detect one or more substance in either salivary fluid or beverage fluid, or in a mixture of these, as such fluids are generally expected to mix and intermingle while an individual user is drinking from a beverage container 100. For example, a sensor 110 may be configured to detect a substance such as a biological analyte, or a metabolite of a biological analyte, or at least one substance indicative of a biological analyte. A substance, such as a biological analyte, may include at least one biological marker, antibody, polypeptide, protein, complex, nucleic acid, cell, pathogen, lipid, alcohol, sterol, carbohydrate, metal, electrolyte, organic compound, nonorganic compound, organophosphate, drug, therapeutic, gas, taggant or pollutant. A substance may be the byproduct of a process used to manufacture the beverage fluid or a substance may originate as an additive to the beverage fluid. A substance may include an analyte, for example an analyte may originate in salivary fluid of a person using a personal use drinking vessel and be incorporated into the fluid in the vessel through the process of drinking. The presence of a substance in a beverage fluid may indicate contamination, such as wherein the substance is an *E. Coli* surface protein, and the presence of the protein may serve to indicate that the beverage container 100 is contaminated with bacteria. Similarly, the substance may include one or more contaminant or admixture that may be undesirable to some beverage drinkers, such as allergens, sweeteners, chemical compounds, glucose, or alcohols. The presence of one or more substance in a salivary fluid may, alone or in combination, be an indicator of a physiologic state, a disease state like an active infection, or a metabolic state. For example, the presence of unusual levels of pepsin activity may indicate the presence of gastroesophageal reflux disease (GERD). See, for example, U.S. Pat. No. 7,402,423 to Taghizadeh, titled "Apparatus for detection of pepsin," which is hereby incorporated by reference. A substance may include one or more substance that is a marker or hallmark of a fluid of interest. For example, pH may be a marker for citrus juice inclusion. For example, glucose or fructose may be a hallmark of total sugar content. For example, a specific microbial protein may be a marker for the microbe as a whole.

The presence of one or more substance, such as an analyte, may alone or in combination be an indicator of a physiologic state, a disease state like an active infection, or a metabolic state in a person drinking from the beverage container 100. A substance, such as a biological analyte, may include at least one metabolite. For example, a metabolite may include a metabolic product generated by the physiology of the individual user. For example the presence of the biological analyte acetone may operate as an indicator of ketosis. See, for example, Musa-Veloso et al., "Breath acetone is a reliable indicator of ketosis in adults consuming ketogenic meals," *Am J Clin Nutr.* 76(1):65-70 (2002), which is herein incorporated by reference. A metabolite may be indicative of a metabolic state of the individual user, for example a metabolite may be indicative of a healthy state, a metabolic disorder, a syndrome, a disease state, or a physiological state. See, for example, Khartinov and Barnes, "Exhaled Markers of Pulmonary Disease," *Am J Respir Crit Care Med,* 163:1693-1722 (2001), and U.S. Pat. No. 6,609,068 to Cranley et al., titled "Personal computer breath analyzer for health-related behavior modification and method," which are herein incorporated by reference. A metabolic disorder includes a hereditary metabolic disorder. A syndrome includes a metabolic syndrome. In some embodiments, the system may include at least one provided agent, such as a drug or compound that may be metabolized by the individual user. A system wherein the substance includes at least one metabolite may also include at least one provided agent, wherein the at least one metabolite includes at least one metabolite of the provided agent. For example, a system user may ingest a provided agent and the sensor 110 may be configured to detect a metabolite of the provided agent.

As illustrated in FIG. 1, a beverage container 100 includes at least one sensor 110 configured to detect at least one substance in a fluid within the personal use beverage container 100. A "sensor" as used herein, includes a unit that specifically identifies a substance, such as a biological analyte, and generates a signal that the identification has been made. A sensor 110 may include a gas or chemical sensor, or an optical, acoustic, or electric sensor. A sensor 110 may include an electrochemical sensor. A sensor 110 may include a biological sensor. The signal generated by a sensor 110 may be, for example, an electrical, visual, magnetic, acoustic, vibrational, heat, light (including infrared (IR) or ultraviolet (UV)), radio frequency (RF) or electromagnetic radiation signal. At least one sensor 110 integral to the beverage container 100 is configured to detect at least one substance in a fluid within the individual-use beverage container 100. A sensor 110 may recognize one or more substance. A sensor 110 may be configured to detect at least one substance in a beverage fluid. A sensor 110 may be configured to detect at least one substance in salivary fluid, such as salivary fluid that has mixed into a beverage fluid while an individual user is drinking. A sensor 110 may be configured to detect at least one substance in an additive or contaminant of the fluid, such as a contaminant diffusing into the fluid from the residue on the surface of the container itself, or an additive originating from a component of the fluid. A sensor 110 incorporated within a beverage container 100 should be operable at appropriate temperatures and conditions, such as pH and the presence of carbonation, present in the relevant fluid. Some types and configurations of sensors, therefore, are not suitable for inclusion within beverage containers configured for use with certain fluids. An external device may be configured to detect at least one signal from the sensor 110. For example, an external device may include at least one port for communication with the sensor 110 that includes one or more instruments for detection of a signal from the sensor 110. For example, an external device that includes at least one port for communication with the sensor 110 integral to the beverage container 100 may include one or more instruments for detection of a signal, such as a signal emitted by a signal emitter integral to the sensor 110.

FIG. 1 illustrates some embodiments of a sensor 110. As shown in FIG. 1, a beverage container 100 including a vessel body configured to hold a beverage 105 includes a sensor 110. The sensor 110 may include a matrix 120 configured for specific binding or retention of a substance 125. The matrix 120 may be configured to bind or retain the substance 125 directly, or it may include one or more recognition elements 145. A recognition element 145 is configured to specifically recognize and retain the substance 125, as illustrated 130. A recognition element 145 may chemically recognize one or more substance 125. A recognition element 145 may bind one or more substance 125, such as through physical association. In some embodiments, the recognition element may be encapsulated 140 prior to contact with the fluid, such as to maintain a stable conformation of the recognition element 145 prior to use. For example, the recognition element 145 may be encapsulated 140 in carbohydrates, lipids, microspheres, oils, emulsions, nanospheres or gum materials. A recognition element 145 may be contained in an emulsion prior to use of the sensor 110. The encapsulation 140 or emulsion of a recognition element 145 may be configured to dissipate, dissolve or be dispossessed through contact with a fluid or a substance. See, for example, U.S. Pat. No. 6,746,529 to Witteveen et al., titled "Stable, spray-dried composition in a carbohydrate substrate and process for obtaining said composition," which is herein incorporated by reference. In some embodiments, a system may include one or more taggant 155, which may be retained in a matrix 120. In some embodiments, a sensor 110 may also include micro-circuitry 115. In some embodiments, a sensor 110 may include a power source 150. A sensor 110 may also include retaining materials, such as a proteoglycan or a charged polymer such as polylysine. Other retaining materials could be included in the sensor 110, such as semi-specific or non-specific adsorbents, such a silica ($SiO_2$) or alumina ($Al_2O_3$)-containing gel or an ion exchange resin, including as part of the matrix 120. A sensor 110 may also include structural material, such as non-reactive gels, plastics or composites configured to shape, enclose or structurally support other components of the sensor 110, including a matrix 120.

A matrix 120 may include one or more gel, like a hydrogel, a hydrosol, a sol-gel, a xerogel, an aerogel, a hydrocarbon gel, a natural polymer gel, a synthetic polymer gel, a ferrogel, a colloid, a responsive gel, a superporous hydrogel or microparticle gel. One or more portion of a sensor 110 may be in a dehydrated form prior to use. For example, a matrix 120 may be may be in a dehydrated form prior to contact with fluid, such as salivary fluid or beverage fluid. A matrix 120 may include a hydrogel including hybrid materials, for example a hydrogel containing a hybrid protein-polysaccharide material. See U.S. Pat. No. 6,821,331 to Damodaran, titled "Protein-polysaccharide hybrid hydrogels," which is herein incorporated by reference. A matrix 120 may be a natural gel like agarose, a natural and/or synthetic polymer gel, hydrogel, or colloid, and may include a gum base such as an acacia gum. See, for example, U.S. Pat. No. 7,022,514 to Vodyanoy et al., titled "Use of acacia gum to isolate and preserve biological material," and US Patent Application No. 2003/0138939 A1 to Vodyanoy et al., titled "Use of acacia gum to isolate and preserve biological material," which are incorporated herein by reference. A matrix 120 may, instead or in addition, be configured as a lipid monolayer or bilayer, as in a micelle or liposome, and may be anchored to a vessel wall through a nonorganic tether. See, for example, "Design of Supported Membranes Tethered via Metal-Affinity Ligand-Receptor Pairs," Radler et al., *Biophysical Journal* 79:3144-3152 (2000), which is herein incorporated by reference. A matrix 120 may be configured as one or more film or layer. A matrix 120 may include at least one of a hydrogel, hydrosol, sol-gel, hydrocarbon gel, natural polymer gel, synthetic polymer gel, lipid, colloid, encapsulation or emulsion. A matrix 120 may be configured as a plurality of spheres, such as micro- or nano-spheres. Such spheres might include protein cages, liposomes, synthetic hybrid cerasomes, microspheres or nanospheres of one or more natural and/or synthetic polymer, including dendrimers. See, for example, Katagiri et al. "Creation of asymmetric bilayer membrane on monodispersed colloidal silica particles," *Colloids Surf B Biointerface*, 38(3-4):149-53 (2004), which is incorporated herein by reference. For example, a matrix 120 may include at least one ligand affinity resin with or without a conjugated peptide or antibody such as those that are commonly used in chromatography and purification. For example a matrix 120 may include at least one ionophore as a recognition element 145 presented on microspheres within the matrix 120. See, for example, U.S. Pat. No. 7,247,489 to Bakker, titled "Ion detecting microspheres and methods of use thereof," which is incorporated herein by reference. For example, distinctly from a recognition element 145 configured as a separate agent, a recognition element 145 may be a recognition site molecularly imprinted within a matrix 120 itself or a part thereof, such as a molecular mimetic. See, for example: U.S. Pat. No. 6,670,427 to Ulbricht et al., titled "Template-textured materials, methods for the production and use thereof;" Ye et al., "Molecularly imprinted polymers as antibody and receptor mimics for assays, sensors and drug discovery;" *Anal Bioanal Chem.* 378(8):1887-1897 (2004); and Peppas et al., "Polymers and gels as molecular recognition agents," *Pharm Res.* 19(5):578-587 (2002), which are incorporated herein by reference.

Depending on the embodiment, a sensor 110 may include types such as gas sensors, "electronic nose" sensors, "electronic tongue" sensors, conductive-polymer gas-sensors (chemoresistors), nuclear magnetic resonance imagers, cantilevers, aptimer-based sensors, surface wave sensors, quartz microbalance sensors, MEMS devices, "Lab-on-a chip" devices, volumetric sensors, or capillary electrophoretic devices. See, for example: U.S. Pat. No. 5,303,585 to Lichte, titled "Fluid Volume Sensor;" Hagleitner et al., "Smart single-chip gas sensor microsystem," *Nature* 414:293-296

(2001); Yusa et al., "Controlled multiple quantum coherences of nuclear spins in a nanometer-scale device," *Nature* 434: 1001-1005 (2005); U.S. Pat. No. 5,174,962 to Brennan titled "Apparatus for determining DNA sequences by mass spectrometry;" and Skelley et al., "Development and evaluation of a microdevice for amino acid biomarker detection and analysis on Mars," *Proc. Natl. Acad. Sci. USA*, 102(4):1041-1046 (2005), which are herein incorporated by reference. See, for example, US Patent Application No. 2007/0021458 to Ishikawa et al., titled "Selective resonance of bodily agents," and Li et al., "The oral fluid MEMS/NEMS chip (OFMNC): diagnostic and translational applications," *Adv. Dent. Res.*, 18: 3-5 (2005), which are herein incorporated by reference.

In some embodiments, the sensor 110 may include a matrix 120 that includes a gel configured to be responsive to a substance 125, wherein the gel is configured to emit a signal when the substance 125 is detected. A gel configured to emit a signal when the substance is detected may be a signal emitter configured to transmit a signal responsive to the at least one sensor 110. For example, a signal emitter may be configured to emit an audible signal responsive to the sensor 110. A signal may include a chromatic, fluorescent, luminescent, or aromatic signal, including as a releasable taggant. In some embodiments a responsive gel may be configured as at least one integral to the beverage container 100. For example, a responsive gel may be operably connected to a transducer configured to convert the response of the gel into a signal. The presence of a substance, such as a biological analyte, may elicit a response from the gel, such as swelling, light emission or release of a taggant, which may be detected by a detector configured to detect the response of the gel and located integral to the external device. The sensor 110 may be configured to allow access to the gel through a permeable area of a covering, and/or a selective medium. A responsive gel may include a swellable hydrogel operably connected to a transducer, such as a pressure sensor configured to convert the swelling response of the gel into a signal. See, for example, Bromberg, "Intelligent polyelectrolytes and gels in oral drug delivery," *Current Pharmaceutical Biotechnology* 4: 339-349 (2003), which is herein incorporated by reference. A swellable hydrogel may include proteins such as the reversibly swellable, biodegradable, cation-binding hydrogel described in U.S. Pat. No. 6,310,105 to Damodaran, titled "Carboxyl-modified superabsorbent protein hydrogel," which is herein incorporated by reference. In some embodiments, the swelling response of a gel may have stages responding to various ligands, which may be configured to be detectable by one or more transducers configured to respond to various stages of swelling. See, for example, Ehrick et al., "Genetically engineered protein in hydrogels tailors stimuli-responsive characteristics," *Nature Materials* 4: 298-302 (2005), which is herein incorporated by reference. Examples of a transducer that may be configured for use with a responsive gel include a pressure sensor, with may be fabricated from a piezoelectric material, such as an acoustical wave sensor or a cantilever sensor configured to convert the pressure of the gel into a sound, radiowave or wireless signal. See, for example: Drafts, "Acoustic Wave Technology Sensors," Sensors Magazine Online, Oct. 1, 2000; Tanaka et al., "Polymer gels that can recognize and recover molecules," *Faraday Discuss.*, 102: 201-206 (1996); and Liu and Ji, "Detection of $Pb^{2+}$ using a hydrogel swlling microcantilever sensor," *Analytical Sciences*, 20:9-11 (2004), which are herein incorporated by reference. In some embodiments, a detector in an external device may receive a wireless signal through a port, and process the signal into results for display to at least one system user. The beverage container 100 may include a mechanism for removal of a module containing the hydrogel, for example by opening the wall of the beverage container 100 for removal or replacement of a module, or by detaching the hydrogel from the beverage container 100.

The at least one sensor 110 may be indirectly responsive to a substance 125. For example, a sensor 110 may be responsive to a metabolite of the substance 125. A metabolite of a substance may include, for example, an enzymatic product such as one produced by an enzyme that is incorporated with the sensor 110. A sensor 110 may be responsive to a metabolite of a biological analyte. For example, a sensor 110 may be responsive to a taggant 155, which may be configured to be released or otherwise detectable in the presence of one or more substance 125. For example, a sensor 110 may be configured to be responsive to a taggant 155 bound to a substance 125.

A sensor 110 may include a recognition element, such as illustrated as 145 in FIG. 1, configured to recognize a substance 125. A recognition element 145 may specifically identify and bind a substance such as illustrated 130. A recognition element 145 may chemically recognize one or more substance. A recognition element 145 may recognize one or more substance, for example through physical or chemical interactions. A recognition element 145 may bind one or more substance, such as through physical association or chemical association. For example, a recognition element 145 may include a peptide chain such as described in U.S. Pat. No. 7,402,423 to Taghizadeh, titled "Apparatus for the detection of pepsin," which is herein incorporated by reference. A sensor 110 may be configured to include one or more recognition element 145, such as immobilized or otherwise embedded in a matrix structure. In some embodiments, a recognition element 145 may specifically bind a substance. In some embodiments, a recognition element 145 may chemically recognize one or more substance. A recognition element 145 may include at least one cell, protein, nucleic acid, carbohydrate, lipid, conjugate, synthetic molecule, or mimetic. A recognition element 145 may be located within a matrix, for instance conjugated to a matrix of agarose beads, or embedded or encapsulated within a matrix structure. A recognition element 145 might itself be a biologic agent, for example: a *staphylococcus* protein A complex, which generally binds immunoglobulins; a binding peptide or protein like an immunoglobulin; a DNA binding protein; a genetically engineered protein; a nucleic acid; an aptamer; a carbohydrate; a lipid; a conjugate; or a synthetic molecule like an artificial antibody or other mimetic. See, for example, U.S. Pat. No. 6,255,461 to Mosbach et al., titled "Artificial antibodies to corticosteroids prepared by molecular imprinting," U.S. Pat. No. 5,804,563 to Still et al., titled "Synthetic receptors, libraries and uses thereof," U.S. Pat. No. 6,797,522 to Still et al. titled "Synthetic receptors," U.S. Pat. No. 5,831,012 to Nilsson et al., titled "Bacterial receptor structures" and US Patent Application No. 2004/0018508 to Friedman, titled "Surrogate antibodies and methods of preparation and use thereof," which are incorporated herein by reference. A recognition element 145 may include an antibody, such as an antibody saturated with a labeled form of the substance, as described in U.S. Pat. No. 5,183,740 to Ligler et al., titled "Flow immunosensor method and apparatus," which is herein incorporated by reference. For example, in embodiments where glucose is an biological analyte to be optically detected by the external device, the recognition element 145 may be a malachite green acceptor covalently linked to insulin. See, for example, Tolosa et al., "Lifetime-based sensing of glucose using energy transfer with a long lifetime donor," *Analytical Biochemistry* 250: 102-108 (1997), which is herein incorporated by reference.

In certain embodiments, a recognition element 145 might be encapsulated in one or more emulsion or encapsulating material 140 instead of or in addition to distribution throughout the sensor 110 and/or in the matrix 120. Proteins, for instance, have been shown to maintain their function when encapsulated. For more information regarding encapsulation of proteins, see, for example: "Fluorescence detection of enzymatic activity within a liposome based nano-biosensor," Vamvakaki et al., *Biosens Bioelectron.* 21:384-8 (2005); Sotiropoulou, et al., "Stabilization of enzymes in nanoporous materials for biosensor applications," *Biosens Bioelectron* 20:1674-1679 (2005); and Besanger, et al., "Screening of inhibitors using enzymes entrapped in sol-gel-derived materials," *Anal. Chem.* 75, 2382-2391, (2003), which are herein incorporated by reference. In some embodiments, a recognition element 145 may be encapsulated 140 prior to contact with fluid, such as to maintain a stable conformation of the recognition element prior to use. For example, a recognition element may be encapsulated in one or more carbohydrates, oils, lipids, microspheres, nanospheres or gum materials. A recognition element may be covered by an emulsion. The encapsulation or emulsion of a recognition element may be configured to dissipate, dissolve or be dispersed through contact with a fluid or a substance. See, for example, U.S. Pat. No. 6,746,529 to Wittevenn et al., titled "Stable, spray-dried composition in a carbohydrate substrate and process for obtaining said composition," which is herein incorporated by reference. Emulsions and encapsulating materials can, for example, include one or more carbohydrate, alginate, protein, protein cage, lipid, phospholipid, liposome, cerasome, oil, emulsion, or a polymer. Encapsulating materials may include photopolymerized water-soluble molecules, such as those described in U.S. Pat. No. 6,258,870 to Hubbell et al., titled "Gels for encapsulation of biological materials," which is herein incorporated by reference.

In some embodiments, the sensor 110 may include one or more biological agent. In some embodiments, the sensor 110 may include one or more biological agent configured to specifically recognize a substance 125. In some embodiments, the sensor 110 may include one or more biological agent configured to provide support or structure to a sensor 110. For example, the sensor 110 may include at least one biosensor. For example, a matrix 120 may include a biosensor. As used herein, "biosensor" refers to a sensor 110 including at least one biological agent or component. A biosensor may include biological agents such as cells, proteins, peptides, nucleic acids, aptamers, lipids, or carbohydrates. A biosensor may include in part a recognition element 145 that incorporates a biological agent, such as a cell, a protein, a nucleic acid, an aptamer, a lipid, and/or a carbohydrate. A biosensor containing a recognition element 145 may include a recognition element configured to transmit a signal when a substance is detected. For example, a recognition element 145 may include one or more genetically engineered cells, which may be configured within solution or immobilized in alginate within a matrix 120. Such genetically engineered cells may be configured to detect a substance 125 through a receptor and then to produce a bioluminescent signal. See, for example, Daunert et al., "Genetically Engineered Whole-Cell Sensing Systems: Coupling Biological Recognition with Reporter Genes," *Chem. Rev.* 100(7): 2705-2738 (2000), which is herein incorporated by reference. As another example, a biosensor containing a recognition element 145 may include an encapsulated enzyme configured to recognize a substance as a substrate wherein the encapsulated enzyme is conjugated or otherwise associated with a responsive compound configured to be fluorescent after the substance is recognized. See, for example, Vamvakaki et al., "Florescence detection of enzymatic activity within a liposome based nano-biosensor," *Biosensors and Bioelectronics* 21: 384-388 (2005), and Sotiropoulou, et al., "Stabilization of enzymes in nanoporous materials for biosensor applications," *Biosensors and Bioelectronics* 20:1674-1679 (2005), and Besanger, et al., "Screening of inhibitors using enzymes entrapped in sol-gel-derived materials," *Anal. Chem.* 75:2382-2391 (2003), which are herein incorporated by reference. As another example, one or more component of a biosensor may be a biologically active molecule bound to a surface, for example using gold-binding fusion proteins. See, for example, the product description from BioHesion™ titled "Advanced Surface Binding Technology," which is herein incorporated by reference. For example, a biosensor may include a bacterial protein. See "Scientists develop biosensor to detect *E. Coli* bacteria," *RxPG News*, Aug. 19, 2006, which is herein incorporated by reference.

In some embodiments, the sensor 110 may include at least one chemical sensor. A chemical sensor may be configured to detect chemical substances present in beverage fluid, for example contaminants or additives that are not generally considered to be healthful. For example, the sensor 110 may detect a chemical agent, such as a pollutant, allergen or additive. Such a chemical agent may be undesirable or dangerous for consumption by some users. A chemical sensor may also be configured to detect chemical substances present in salivary fluid, for example chemicals or metabolites ingested by a person drinking from the beverage container 100, either before or during drinking from the beverage container 100. Multiple types of chemical sensors may be implemented. See, for example, Snow et al., "Chemical Detection with a Single-Walled Carbon Nanotube Capacitor," *Science* 307:1942-1945 (2005), which is incorporated herein by reference.

A beverage container 100 including a vessel body may include one or more taggant 155. A taggant, as used herein, refers to a chemical or physical component which is configured to be detectable, such as through direct visual or olfactory detection by a user, or detection through a device or assay. A taggant is configured to enhance detection of one or more substance, either directly or indirectly. For example, a taggant bound to a substance may be directly detected. For example, a taggant released when a substance binds to a recognition element may be an indirect indicator of the presence of the substance. Numerous types of taggants exist and various configurations may be utilized. For example, FIG. 1 depicts taggant 155 included in a matrix structure 120. In some embodiments, a taggant 155 may be included in a matrix 120 or retaining materials of a sensor 110. In some embodiments, a taggant 155 may be included in a matrix 120 configured for slow release of the taggant. In some embodiments, a beverage container 100 may be configured to store taggant 155 at a distance from the sensor 110. A beverage container system may include a taggant storage region. A taggant storage region may be configured to release taggant 155 at a specific time or in response to a condition, such as physical pressure, temperature, pH or hydration. For example, taggant 155 may be included in a reservoir configured to expel taggant 155 in response to physical pressure of a person placing their lips on a portion of the beverage container 100, for example while drinking from the beverage container 100. For example, a taggant 155 may be released through flexing of a support surface configured to be responsive to binding of a substance 125 to a recognition element 145. See, for example, Boisen et al., "Rapid molecular detection of food- and water-bourne diseases," *Microbiology Today*, August 2007, 116-118, which is herein incorporated by reference. Numerous types of taggants exist and various configurations may be utilized. A taggant 155 might include a dye, chromogen, a fluorescent substance, a luminescent substance, an odorant, a protein, a nucleic acid like an aptamer, a carbohydrate, a lipid, a synthetic molecule, a quantum dot, an optically active compound, a magnetic compound, a genetically engineered protein, a molecule configured for release, a resonance energy transfer molecule, a metal, a mass-label molecule, a radioisotope, or a volatile compound. For example, see US Patent Application No. 2003/0022225 to Monforte et al., titled "Releasable nonvolatile mass label molecules," U.S. Pat. No. 6,635,452 to Monforte et al. titled "Releasable nonvolatile mass label molecules," U.S. Pat. Nos. 5,516,931, 5,604,104 and 5,602,273 to Giese et al., titled "Release tag compounds producing ketone signal groups," U.S. Pat. No. 5,360,819 to Giese titled "Molecular analytical release tags and their use in chemical analysis," and U.S. Pat. No. 6,491,643 to Katzman and Carlebach, titled "Breath test analyzer," which are herein incorporated by reference. A taggant 155 may be included in the matrix 120 and released when a substance 125 binds, such as in a displacement assay. A taggant 155 may be dehydrated prior to use, including dehydrated in complex with a recognition element 145. See, for example, U.S. Pat. No. 5,354,654 to Ligler et al., titled "Lyophilized ligand-receptor complexes for assays and sensors," which is herein incorporated by reference. The taggant 155 may be configured as a passive label for the substance 125, such as a nonspecific dye like a cyanine dye, configured to bind to nucleic acids. Instead of or in addition, the taggant 155 may be configured to be responsive to binding of the substance 125, for example a labeled recognition element such as a fluorescein-conjugated antibody able to complex with the substance, or a recognition element like a transferase including a recognition site for the substance and configured to transfer the taggant as a labeled modifier such as a phosphate or carbohydrate group. See, for example, US Patent Application No. 2003/0022225 to Monforte et al., titled "Releasable nonvolatile mass label molecules," and U.S. Pat. No. 6,635,452 to Monforte et al. titled "Releasable nonvolatile mass label molecules," which are herein incorporated by reference. If the substance 125 or the recognition element 145 includes a catalyst or enzyme, the taggant 155 may include a substrate with a tag configured to be cleavable or activatable. As another example, a recognition element 145 may be configured to exhibit altered conformation upon binding a substance 125, such as a calcium-dependent binding molecule like calmodulin, possibly as part of a fusion protein, and/or configured to allow resonance transfer. See, for example, Miyawaki et al., "Fluorescent indicators for $Ca^{2+}$ based on green fluorescent proteins and calmodulin," *Nature* 388: 882-887 (1997), which is incorporated herein by reference. The taggant 155 may be incorporated in or intrinsically part of one or more material forming the matrix 125 or the beverage container 100, including the vessel body, and responsive to binding of the substance, such as a stimuli-responsive gel.

In some embodiments, a recognition element 145 may include a conjugated taggant, such as a labeled antibody. A conjugated taggant is a taggant that is not configured for release from the recognition element 145. In some embodiments, a recognition element 145 may include a releasable taggant compound. Many types of releasable compounds are available, such as nonvolatile mass tags. See, for example, US Patent Application No. 2003/0022225 to Monforte et al., titled "Releasable nonvolatile mass label molecules," and U.S. Pat. No. 6,635,452 to Monforte et al. titled "Releasable nonvolatile mass label molecules," which are herein incorporated by reference. Volatile release taggants may also be utilized in some embodiments. See, for example, U.S. Pat. No. 5,610,020 to Giese et al., titled "Release tag compounds producing ketone signal groups," which is incorporated herein by reference. In some embodiments, a release taggant may be presented in the matrix 120 as a lipid layer. See, for example, U.S. Pat. No. 6,949,347 to Singh and Chan-Hui, titled "Multiplex analysis using membrane-bound sensitizers," which is herein incorporated by reference. In some embodiments, the sensor 110 might include a matrix 120 that includes a gel configured to be responsive to a substance 125, wherein the gel is configured to emit a signal when the substance 125 is detected. A signal may include a chromatic, fluorescent, luminescent, or aromatic signal, possibly as a releasable taggant. Examples include a polymerized crystalline colloidal array responsive to glucose. See, for example, U.S. Pat. Nos. 6,187,599 and 6,544,800 to Asher et al., titled "Polymerized crystalline collidal arrays," which are herein incorporated by reference. The Asher group at the University of Pittsburgh has also described the fabrication of polymerized crystalline colloidal arrays. See the attached printout of the Asher Laboratory materials titled "Colloid Group", which are incorporated herein by reference. A releasable taggant may include a labeled form of the target bound to an antibody, wherein the labeled form of the target is released during attachment of the substance 125 from the sampled fluid to the antibody, as described in U.S. Pat. No. 5,183,740 to Ligler et al., titled "Flow immunosensor method and apparatus," which is herein incorporated by reference.

As illustrated in FIG. 1, the beverage container 100 might further include electronic circuitry, such as microcircuitry 115, and in some embodiments may include a power source 150 such as a microbattery, which may be housed, for instance, within a vessel body 100 such as within the wall of the vessel, within the base of the vessel, or attached to the outside of the vessel. A power source 150 may include, for example, one or more batteries, electrical connections with an external power source or one or more power-generating elements such as solar cells. A power source 150 may include one or more power sources such as a battery, microbattery, solar energy converter, fuel cell, biofuel cell, or power cord. In some embodiments, wireless transmission may serve as a means to power the system, including microcircuitry 115 within the beverage container 100. See US Patent Application No. 2005/0143787 to Boveja titled "Method and system for providing electrical pulses for neuromodulation of vagus nerve(s), using rechargeable implanted pulse generator," which is herein incorporated by reference. One or more power sources 150 may be rechargeable or replaceable. One or more power sources 150 may be operably connected to any module of the beverage container 100, for example signal emitters. The microcircuitry 115 and power source 150 may be readily visible to a user, such as including wires embedded within the vessel walls. The beverage container 100 may include internal space configured to protect microcircuitry 115 from contact with a fluid, such as an internal space within the walls of the vessel body or in a base, handle, or attachment to the beverage container 100. In some embodiments, the microcircuitry 115 and power source 150 may be configured to have a pleasing appearance or presentation. A power source 150 may include modular elements configured for replacement or realignment, for example batteries that may be swapped out or replaced. Microcircuitry and one or more power source may also be included, for example, in a handle, cover, lid or sleeve of a beverage container 100.

The beverage container 100 might further include electronic circuitry, such as microcircuitry 115, that specifically recognizes a particular individual user or a class of users. For example, a beverage container 100 may include electronic circuitry configured to allow a user to implement the sensor 110. For example, a beverage container 100 may include electronic circuitry configured to respond to one or more signals from an external device by implementing one or more units of the beverage container 100, such as one or more sensors, sensing elements, or reservoirs. Such a signal may specifically identify an individual user relative to that user's preferences or profile, resulting in the implementation of a group of preselected functions in the electronic circuitry. For example, an external device may signal that person X is using the beverage container 100, resulting in the implementation of a previously saved group of parameters in the electronic circuitry. For example, an individual user may preselect that their data should be saved to a medical network, and/or communicated to a medical professional. For example, an individual user may preset the system to signal with flashing lights when a particular substance is detected. A beverage container 100 may include electronic circuitry configured to send a signal to one or more external devices regarding data specific to an individual user, such as data from one or more sensors or sensing elements obtained during use of the beverage container 100 by the individual user. Similarly, a beverage container 100 may include circuitry configured to responsive to signals from an external device identifying an individual user as part of a larger group or class and set the parameters of operation accordingly based on prerecorded data. For example, an individual may be identified as a diabetic and the electronic circuitry may be configured to implement a diabetic diagnostic program. For example an individual may be identified as hard of hearing and the electronic circuitry may be configured to implement visual display and not be configured to implement auditory signals. For example an individual may be identified as a barroom user of the beverage container 100 and the electronic circuitry may be configured to implement a prerecorded amusing or entertaining light display.

In some embodiments, a beverage container 100 may include at least one salivary fluid collection unit. For example, a beverage container 100 may include an aperature connected to a reservoir region for retention of fluid, which may also include absorbent material. A salivary fluid collection unit may be operably connected to, for example, a region of the top edge of the vessel walls configured for drinking, a lid region configured for drinking, or a drinking straw. A salivary fluid collection unit may be operably connected to a sensor 110, such as configured to provide a conduit for salivary fluid to contact the sensor 110. A salivary fluid collection unit may be a reservoir distinct from the sensor 110, for example a salivary fluid collection unit configured to store salivary fluid for later analysis. A salivary fluid collection unit may be modular, and be configured for removal and replacement, including for cleaning, refreshment, refurbishment and reuse.

FIG. 2 illustrates aspects of a sensor 110 configured to detect one or more substance in fluid. A plurality of agents may be present throughout or in distinct regions of the sensor 110, as illustrated in FIG. 2A. Portions of the sensor 110 may be modular, and be configured to be swappable, replaceable, removable, and/or rechargeable. For example, a used module may be configured to be replaced by a fresh module. For example, a module of some functionality may be configured to be swapped out and replaced with a module of different functionality. At least a portion of the sensor 110 may be in dehydrated form prior to contact with fluid, for example when at least one module is in dehydrated form and configured for hydration through contact with the fluid. See, for example, U.S. Pat. No. 5,354,654 to Ligler et al., titled "Lyophilized ligand-receptor complexes for assays and sensors," which is herein incorporated by reference. Modules or regions may be configured, for example, as adjacent units 200 as depicted in FIG. 2A, which depicts modules arranged as adjacent blocks. In some embodiments, various regions may be configured from different materials, such as a different type of gel, like sol gels with varying pore size, or pH-responsive or ion-responsive gels. Embodiments with various regions configured from different materials would allow for the sensing of a variety of substances in different units of the beverage container 100. For example, as depicted in FIG. 2A, one module of a sensor 110 may include recognition elements of one type 145, while other modules may include recognition elements of a different type 220 and/or encapsulated elements 140. For example, recognition elements of one type 145 may recognize and bind a substance 125 while other modules with distinct recognition elements 220 may not bind the substance. Embodiments with various regions configured from different materials would allow for the sensing of a variety of substances in different units of the sensor 110. Embodiments with various regions configured from different materials would allow for ready identification of sensed substances by a system or network, such as by logic-based processes. For example, a specific substance may be identified by a logic-based process component of a system. For example, a system may include logic such as: module X detects biological analyte Y, and therefore if module X has detected a substance, it is inferred to be biological analyte Y. One or more regions or modules may include taggant 155.

One or more module of a sensor 110 may include a gel. For example, a gel may include a hydrogel, hydrosol, sol-gel, xerogel, aerogel, smart gel, hydrocarbon gel, natural polymer gel, synthetic polymer gel, superporous gel, ferrogel or a colloid. For example, a matrix 120 may include a gel. In some embodiments, various regions or modules of a sensor 110 may be configured from different materials, such as a different type of gel, like sol gels with varying pore size, or pH-responsive or ion-responsive gels. In some embodiments, a gel may be configured to be directly responsive to a substance 125, such as when the gel is configured to include a recognition site. See, for example, Byrne et al., "Molecular imprinting within hydrogels," *Advanced Drug Delivery Reviews* 54: 149-161 (2002), Peppas and Huang, "Polymers and gels and molecular recognition agents," *Pharm Res.* 19(5):578-87 (2002), and US Patent Application No. 2007/0190084 to Hilt et al., titled "Polymer network compositions and associated methods," which are herein incorporated by reference. In some embodiments, there may be a plurality of molecularly imprinted recognition sites specific to particular regions or modules. Some embodiments may include one or more gel configured to recognize and respond to a substance 125, for example a hydrogel that selectively recognizes and sequesters a metal. See, for example, Peppas and Huang, Ibid and Tanaka et al., "Polymer gels that can recognize and recover molecules," *Faraday Discuss.*, 102: 201-206 (1996), which are herein incorporated by reference.

As shown in FIG. 2B, a sensor 110 may be configured in layers 210. For example, a sensor 110 may include layers 210 of different materials such as different gels or one or more gel and one or more supporting material, protective material, or selective material. A sensor 110 may also include at least one recognition element configured as a recognition site 205, such as a molecular mimetic, which may be molecularly imprinted within a matrix 120 itself or a part thereof, such as a gel. In some embodiments, the sensor 110 may include at least one selective medium layer. One or more layer may include one or more taggant 155. One or more layer may be a biologically active molecule bound to a surface, for example using gold-binding fusion proteins. See, for example, the product description from BioHesion™ titled "Advanced Surface Binding Technology," which is herein incorporated by reference. Multiple modular regions or layers may also form an indicator system for presence of a substance 125, such as described in the PCT Patent Application Publication No. WO 2008/006152 A1 to Brockwell and Holland, titled "Indicator system for determining biological analyte concentration," which is herein incorporated by reference.

A sensor 110 may include a selective medium configured to allow at least one substance from fluid to enter or permeate into at least one region of the sensor 110. The selective medium may include material configured as a screen with openings for the passage of some fluid components, such as a substance, and the exclusion of others, such as larger particulates or macromolecules. A selective medium may be configured as a layer of a sensor 110 such as illustrated 210 in FIG. 2B. A selective medium may be configured to filter out, for example, debris, cells, molecules of a range of sizes (including those above or below a specific range), charged molecules, or any other undesirable material, even excess moisture, while being configured to allow some other substances to pass through. Such a selective medium could be made from any of a number of materials including charcoal or cellulose; a synthetic polymer such as but not limited to polyethylene, polycarbonate, nylon, polyester, polysiloxane, or polypropylene; or a hydrogel, or a monolayer or bilayer of lipids, and a selective medium could include a protein. For example, a selective medium may include a layer made of cellulose configured with pores sized to allow diffusion of certain sized molecules, a hydrogel film of a type that swells at a certain pH, a gas-permeable membrane or a hydrophobic lipid bilayer. See, for example, "A hydrogel-based $CO_2$ sensor," Herber and Olthuis, MESA+ Institute for Nanotechnology, University of Twente, which is incorporated herein by reference. For example, a selective medium may include biocompatible membranes such as those described in U.S. Pat. No. 6,258,870 to Hubbell et al., titled "Gels for encapsulation of biological materials," which is herein incorporated by reference. The selective medium could also or instead include one or more active transporter, such as a porin or ion transporter. A selective medium may be configured as a module or layer.

Figure 3:
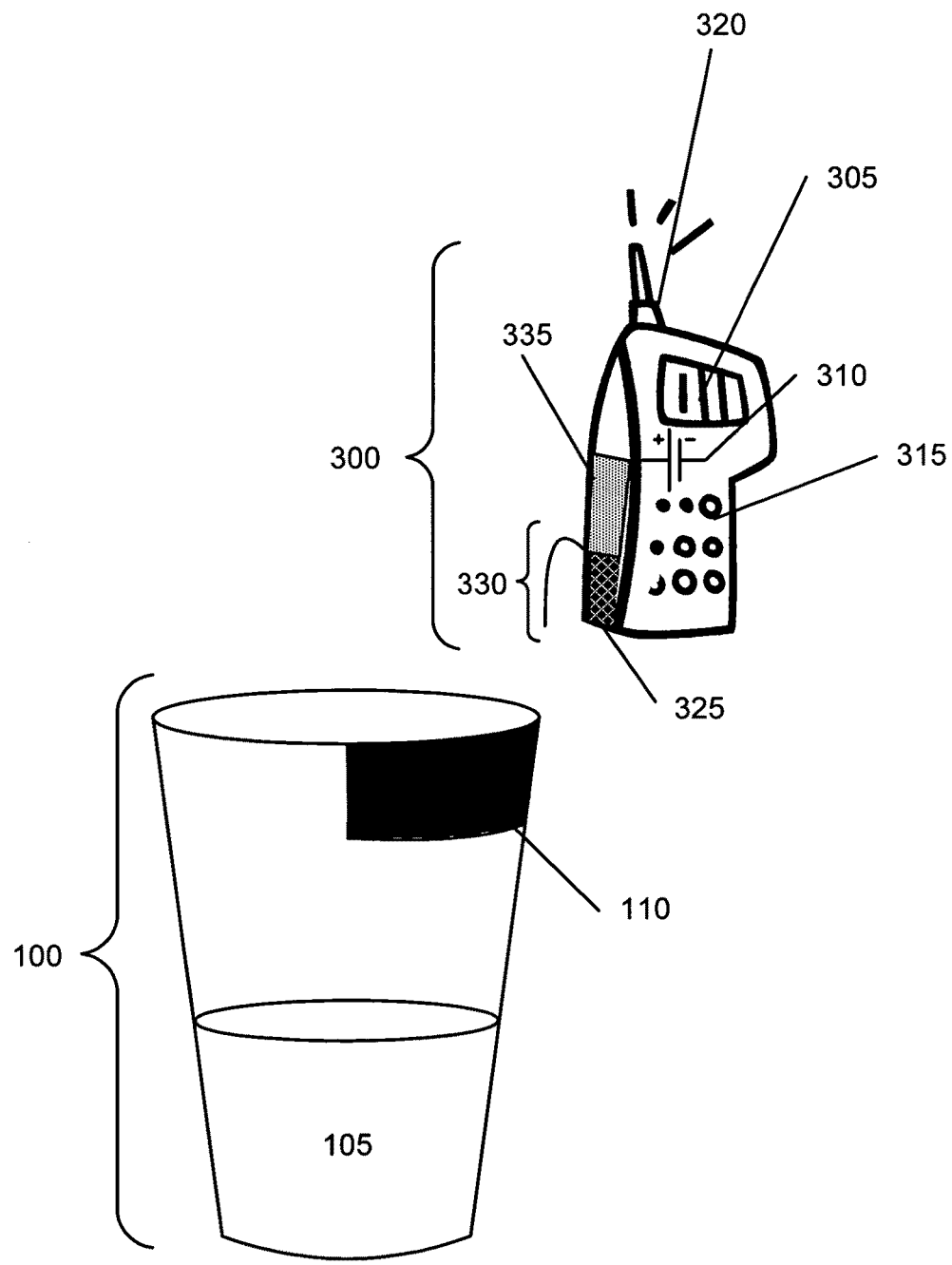
FIG. 3 is a schematic of a beverage container and an external device.

FIG. 3 depicts a beverage container 100 with a vessel body configured for holding a beverage 105 and including a sensor 110. As illustrated in FIG. 3, in some embodiments the system includes at least one beverage container 100 with a vessel body including at least one sensor 110 configured to detect one or more substance in fluid, and at least one external device 300 including at least one port 325 configured for communication with the at least one sensor 110. As shown in FIG. 3, the external device 300 may be a handheld device. In some embodiments, the external device 300 may include at least one sensor 110. In some embodiments, the external device 300 may be incorporated into another object, such as a table, coaster, tray, detachable drinking vessel foot, sleeve, or base, bartop, or stand. In some embodiments, the external device 300 may be incorporated into a fixture, furnishing or fitment of a room, such as a table, bartop, shelf, stand, decorative object, wall ornament or display. The external device 300 may include a positioning element 330. Although the positioning element 330 in FIG. 3 is depicted as a crook with a hooked shape, in some embodiments it may be configured as a wall, face, indentation or bar of a size and shape to position the external device 300 in alignment with the sensor 110 as appropriate to the port and/or detector. In some embodiments, the sensor 110 may be located in the base of a beverage container 100 and the external device 300 may be configured as a coaster or tray, and may include at least one indentation of a size and shape to position the sensor 110 in alignment with the external device 300. In some embodiments the external device 300 may not include a positioning element 330.

The external device 300 is configured to detect at least one signal from the at least one sensor 110. A signal may include, for example, light, sound, vibration, IR, radio, wireless or other detectable signals. For example, one or more external devices 300 configured for detection of a signal from the sensor 110 may include a port configured for communication with the sensor 110. For example, where the sensor 110 is configured to emit light after binding one or more substance, the external device 300 includes an external device configured to identify light, such as an external device configured to detect non-visible light or light of a specific wavelength. See, for example, US Patent Application No. 2003/0143580 to Straus titled "Rapid and sensitive detection of molecules," which is herein incorporated by reference. In embodiments in which the sensor 110 and/or an associated taggant 155 is configured to emit optically-detectable signals, the port includes in part or whole an optically-permeable section (e.g. a window), and the external device 300 includes at least in part a spectrophotometer and/or light source configured to elicit signals from the sensor 110 or taggant 155. For example, the sensor 110 or taggant 155 may include at least one of a chromogen, fluorescent agent, luminescent agent, a quantum dot, or a compound configured to exhibit alterable optical density. A light source associated with a external device 300 may include, for example, a light emitting diode or other light source, such as a source configured to provide light in a variable and/or specific wavelength, including in the infrared or ultraviolet spectra. See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," US Patent Application No. 2008/0265146 to Coates, titled "Integrated sensing module for handheld spectral measurements," and WIPO Patent Application Publication No. WO 2007/113727 to Kolesny-Chenko et al., titled "A portable food and/or beverage analyzer and a method of analyzing a food and/or beverage in the field," which are herein incorporated by reference. For example, a light source may be configured to detect the opacity or colorimetric response of a component of the sensor 110. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" US Patent Application No. 2003/0023189 to Kuo, titled "Handheld diagnostic device with renewable biosensor;" and US Patent Application No. 2002/0127143 to Kuo, titled "Saliva-monitoring biosensor electrical toothbrush," which are herein incorporated by reference. In some embodiments, the external device 300 may use electric pulses to measure the conductivity of a sensor component. See, for example, U.S. Pat. Nos. 6,623,698 and 7,314,453 to Kuo, as above, which are herein incorporated by reference. In embodiments in which a taggant 155 is a volatile compound, the external device 300 may include a gas sensor such as an acoustic wave, chemiresistant, or piezoelectric sensor, such as those described as an "electronic nose" or "electronic tongue." See, for example, U.S. Pat. No. 5,571,401 to Lewis et al., titled "Sensor arrays for detecting biological analytes in fluids," and US Patent Application No. 2004/0006257 to Burch, titled "Detection, diagnosis, and monitoring of a medical condition or disease with artificial olfactometry," which are herein incorporated by reference. See, for example, Lavigne et al., "Solution-based analysis of multiple analytes by a sensor array: toward the development of an "electronic tongue," Journal of the American Chemical Society, 120: 6429-6430 (1998), which is herein incorporated by reference.

As shown in FIG. 3, an external device 300 may include a reporting device 305, for example visual display elements configured to indicate when a substance has been detected. For example, the external device may include lights, a display, an auditory signal generator, or a vibration emitter. The external device 300 may include at least one communication device including a telecommunication device, a display screen, a speaker, a printer, or a data processor. The external device 300 may include digital memory. For example, the external device 300 may include digital memory that is configured to record received or sent signals, information regarding detected substances, time, temperature or pH associated with the detection, or other data. In some embodiments, the digital memory may include information regarding one or more users, such as their allergies, dietary preferences, or taste preferences. The digital memory may include one or more databases, tables, or lists. The external device 300 may also include a user interface such as a display screen, touchpad, E-ink device, auditory signal generator, or other interface, for example a keyboard interface 315. The external device 300 may include one or more power source 310, for example one or more batteries, electrical connections with an external power source or one or more power-generating elements such as solar cells. The external device 300 may include one or more power sources such as a battery, microbattery, solar energy converter, fuel cell, biofuel cell, or power cord. One or more power sources may be operably connected to any module of the external device 300, for example display elements, reporting elements, or communication elements. The external device 300 may include a telecommunication device, which may include an antenna 320 or a cable to transmit and receive information from a network or additional computer device, such as a healthcare system computing device or an individual user's personal data organizer (PDA), laptop or cell phone. For example, the external device 300 may be configured to communicate with a network, such as a network that contains at least one medical history, for example a medical history of the individual drinking from the beverage container 100, or of a reference individual or group. See, for example: US Patent Application No. 2004/0078219 to Kaylor et al., titled "Healthcare networks with biosensors;" US Patent Application No. 2004/0100376 to Lye et al., titled "Healthcare monitoring system;" and Lempert, "Digital house calls? Check your health at home," MSNBC Feb. 21, 2006; which are herein incorporated by reference. For example, an external device 300 may be configured to communicate with a network including one or more computer, as described in U.S. Pat. No. 7,483,805 to Sparks et al., titled "Sensing and analysis system, network, and method," which is herein incorporated by reference. The medical history may include, for example, genetic or genomic information, drug use history, allergies, medical diagnoses, or surgical history. The external device 300 may also include additional elements or instrumentation 335 as desired in a specific embodiment. The external device 300 may be incorporated into another device, such as a PDA, laptop, or cell phone.

An external device 300 could further include, configured to act in communication with one or more sensor 110, additional instrumentation of one or more type configured to process fluid, a constituent thereof, or a sample contained therein; examples include a fluidic or microfluidic system and/or means of providing additional taggants. For example, where the substance includes advanced glycation endproducts, the external device 300 may be configured to treat salivary fluids with hypochloric acid and for examination of the treated material with NMR spectroscopy. See Yoon et al., "Characterization of advanced glycation endproducts in saliva from patients with diabetes mellitus," *Biochem. Biophys Res Comm.*, 323: 377-381 (2004), which is herein incorporated by reference.

A external device 300 may include at least one communication device, such as a reporting device like a display screen, a speaker, or a printer, and may be configured for interaction with a system user, for example through a keyboard interface 315. For example, a communication device may be configured to accept queries or directions from at least one system user. An external device may include at least user interface device such as a touchscreen, keyboard, or voice activation/recognition system. An external device 300 may include multiple modules, for instance a handheld module configured to communicate with a separate component. A external device 300 may include a telecommunication device, such as a telecommunication device configured to communicate with a network, such as an area, localized, and/or centralized network. A network may include one or more database, such as but not limited to one or more medical history, including a genomic history such as genetic or genomic test results, or family information. The external device 300 may be configured as a portion of a network, which might include as a conductive medium part or all of the body. See, for example, U.S. Pat. No. 6,754,472 to Williams et al., titled "Method and apparatus for transmitting power and data using the human body," which is incorporated here by reference. For example, the external device 300 may be attached to or configured to be worn on the human body. The external device 300 may be configured as a portion of a network that is integrated with part or all of a building, such as in a domotic, for instance the MavHome under study at the University of Texas at Arlington. The external device 300 may be configured as a portion of a network for LED light display as described in International Patent Application No. WO 99/31560 to Mueller et al., titled "Digitally controlled illumination methods and systems" which is herein incorporated by reference. A network may be a public health response network. For example, an external device 300 may send and receive information from a local health department, such as to report a contaminant or to obtain up to date information regarding possible contaminants or pathogens reported in beverages, or recalls issued regarding beverages. Information stored on a network or within an individual external device 300 may be accessed at a later time, for example if there is a delayed response by the individual user who has consumed a beverage or if there is a later report of a problem by another individual. An external device 300 may be incorporated into another device, such as an individual user's cell phone, PDA, or laptop. An external device may be configured to communicate with a specific beverage container 100 or a class of beverage containers, for example beverage containers with a certain module set or configured with a particular capability.

Other components of the system may include a digital processing unit, which may be programmable and may include memory. Other components of the system may include at least one data processor configured to implement logic such as comparison, sorting, reduction, and/or endpoint determination. The system may be configured with a data processor configured to collect and analyze multiple data points in a relative fashion, including either serially or in parallel. The system may also include additional sensors such as a thermometer or pH meter and/or instruments such as a timekeeping device or clock.

FIG. 4 depicts aspects of the systems and methods described herein. As shown in FIG. 4, an external device may be integrated into a room component such as a table or bar top. As illustrated in FIG. 4A, a beverage container 100 includes a vessel body configured to hold a beverage 105, and at least one sensor 400 associated with the vessel body, the at least one sensor 400 including a biological analyte sensor configured to detect a biological analyte in a fluid. FIG. 4A depicts the sensor 400 as located at the bottom of a beverage container 100 for the purposes of illustration. FIG. 4A also shows a drinking straw 405 configured to enhance mixing or intermingling of salivary fluid and beverage fluid in the region of the sensor 400. The drinking straw 405 is illustrated as being retained in a limited range of locations relative to the vessel body of the beverage container 100 and sensor 400 by a retaining guide 410. Although the retaining guide 410 is depicted as a loop or circle, in some embodiments a retaining guide 410 may be incorporated into other structures. For example, a retaining guide 410 may be incorporated into a lid or the lip of the vessel wall. FIG. 4B illustrates that a beverage container 100 such as the one illustrated in FIG. 4A may be incorporated into a system including one or more external devices, which may include, for example, detectors, indicators, sensors, user interfaces, and computing devices.

FIG. 4B depicts the beverage container 100 illustrated in FIG. 4A, including a beverage container 100 with a vessel body, sensor 400 and drinking straw 405, resting on a table 415. The table 415 includes an external device, which may include a detector configured to detect a signal from a sensor 400. As depicted in FIG. 4B, an external device incorporated into an object such as a table or bar may include a port 420 configured for communication with the sensor 400 that is a defined region on the table or bar top configured to match the sensor 400 in location and size. In some embodiments, the port 420 configured for communication with the sensor 400 may encompass a large region of a table or bar top, and may not be immediately noticeable to a casual observer. The port 420 may be configured for communication with signals based on vibration, light, sound, induction, radio frequency (RF), or other wireless signals as suitable for a particular embodiment. The port 420 may include a wire connection between the external device and the beverage container 100, including wire connector. As shown in FIG. 4B, an object, such as a table 415, incorporating an external device with a port 420 configured for communication with the sensor 400 may include an indicator device 425. As depicted in FIG. 4B, an indicator device 425 may include an indicator that displays when a specific substance or class of substances is detected, such as toxins, allergens or substances that may be desirable or undesirable to some users. For example, an indicator device 425 may show a warning sign or symbol. An indicator device 425 may also, depending on the embodiment, be configured to indicate when the lack of a specific substance or group of substances has been detected, such as a lack of toxins, allergens, alcohol, medications or substances that may be desirable or undesirable to some users. An indicator device 425 may include one or more light displays, for example light displays embedded in the tale or bar top, which are configured to switch on in response to a signal from the external device.

In some embodiments, the external device may send and receive communication signals 435 from a remote computing device 430, which may be a portion of a network. For example, the external device and the remote computing device 430 may communicate via wireless, cable, electronic, IR, RF, auditory or optical signals. A system user 440, such as a caregiver, medical personnel, public health professional, food service professional, or individual user may interact with the computing device or network. Although system user 440 is shown/described herein as a single illustrated figure, those skilled in the art will appreciate that system user 440 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

Figure 5:
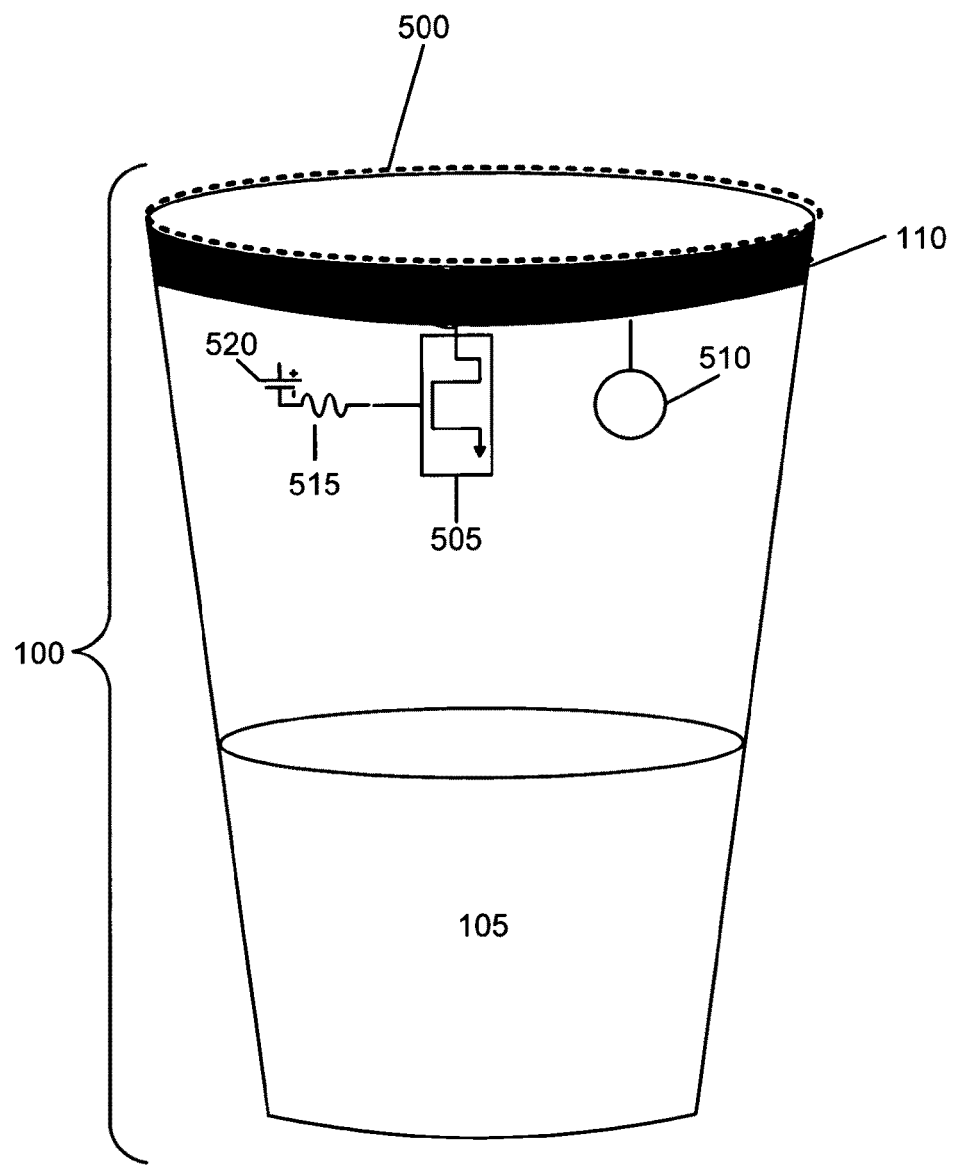
FIG. 5 is a schematic of a beverage container.

FIG. 5 depicts embodiments of a beverage container system. A beverage container 100 including a vessel body configured for holding a beverage 105 includes a sensor 110. For purposes of illustration, the sensor 110 is shown in FIG. 5 as a ring or rim region around the top edge of the walls of a vessel. In some embodiments, the beverage container 100 including a vessel body may also include at least one signal emitter. The signal emitter may be operably attached to the sensor. For example, the vessel body may include at least one light emitter 500. For example, FIG. 5 depicts a light emitter 500, operably connected with the sensor 110. In some embodiments, the signal emitter and the sensor 110 will be integrated, such as in embodiments wherein the sensor 110 is directly connected to the signal emitter in a configuration wherein the signal emitter is initiated to start a signal when the sensor 110 binds a substance. Although the light-emitting mechanism is depicted in FIG. 5 as a row of lights encircling the edge of the vessel body, a light emitter 500 may be located in any portion of the drinking vessel, such as in the side, bottom, or throughout the vessel. In some embodiments, the light-emitting mechanism may be configured to display a pattern, which may have meaning such as a barcode, words, numbers, or figures. In some embodiments, a light emitter 500 may emit light of a specific wavelength, which may or may not be a visible wavelength. For example, a light-emitting mechanism may emit light of a visible wavelength of a specific color. For example, a light emitter 500 may emit light of a specific wavelength outside of the normal visual spectrum, such as infra-red or ultraviolet. In such embodiments, the light emissions may be detected, for example, by a light detector within the vessel or within an external device. Non-visible light emissions may be detected by an external device configured to detect non-visible light of the appropriate wavelength, such as a UV or fluorescence detector.

A signal emitter may include a signal emitter such as a vibration-generating mechanism. For example, the beverage container 100 including a vessel body may include at least one vibration-emitting mechanism 510. The vibration-emitting mechanism may be operably attached to the sensor 110. For example, a substance binding a component of the sensor 110 may operate to initiate the activity of a vibration-emitting mechanism. A vibration-emitting mechanism 510 may propagate vibrations that can be manually felt by an individual holding the beverage container 100; for example, the vessel walls may vibrate with sufficient force that an individual may detect the vibration visually or through touch. In some embodiments, the vibrations acting on the vessel body of the beverage container 100 may create sound waves that may be audible. A vibration-emitting mechanism 510 may propagate vibrations that are not detectable by an average individual, but may be detectable by a detector in a external device, for example an external device placed in contact with the beverage container 100 such as a external device on which the container may be placed, or an external device clipped or attached to the container. For example, a vibration-detecting external device may be configured as a coaster, within a drink tray, or integrated in a table top. For example, a vibration-detecting external device may be configured as a beverage container 100 sleeve, base, detachable handle, clip-on unit, or stick-on attachment. A vibration-emitting mechanism 510 may propagate vibrations that are not detectable by an average individual, but may be detectable by an animal, such as a dog. In some embodiments, the vibration-emitting mechanism 510 may be configured to emit vibrations of a frequency, amplitude or periodicity that conveys additional information. For example, in embodiments wherein the sensor 110 is configured to detect multiple substances, such as depicted in FIG. 2, a vibration-emitting mechanism 510 may emit distinct vibrations depending on which module of the sensor has bound a substance, and so convey to an individual or system user information regarding the type of substance detected.

A signal emitter may also include an auditory signal-emitting mechanism, or an electric pulse emitting mechanism. For example, the system may be configured to beep when a fluid has been detected for a minimum amount of time required to sense a potential substance. For example, the system may be configured to emit an electric pulse to a beverage drinker after a specific substance has been detected, such as an allergen or a contaminant. Such a pulse may serve to alert the individual beverage container user to stop drinking the beverage immediately.

In some embodiments, a beverage container 100 may include at least one sensing device 505, such as a temperature sensor, pH detector, pressure sensor, or time-keeping device. For example, FIG. 5 depicts a sensing device 505 such as a clock operably attached to the vessel wall of the beverage container 100. In some embodiments, one or more taggant, medicinal agent, or signal may be operably connected to one or more sensor 110, such as a taggant reservoir which is triggered to release material at a preset time point or in response to a change in pH inside the container. In some embodiments, a signal may be generated by the system in response to one or more sensor 110, such as a light or vibratory signal that is generated in response to the detection of a temperature, pH or pressure range. In some embodiments, data from one or more sensor 110 may be transmitted or recorded along with the sensed data, such as when temperature or pH relevant to the sensor is included in information communicated to the external device.

As shown in FIG. 5, in some embodiments a beverage container system may include micro-circuitry 515. A beverage container system may also include at least one power source 520. A power source 520 may include one or more power sources such as a battery, microbattery, solar energy converter, fuel cell, biofuel cell, or power cord. One or more power sources may be operably connected to any module of the beverage container 100, for example signal emitters. The microcircuitry 515 and power source 520 may be readily visible to a user, such as including wires embedded within the vessel walls. The visible microcircuitry 515 and power source 520 may be configured in an amusing or informative aspect. The microcircuitry 515 and power source 520 may be configured in a detachable module, for example in a sleeve, handle, or retainer for the beverage container 100.

A beverage container 100 may include at least one signaling element. A signaling element may function to emit a signal after contact between the beverage container 100 and fluid has occurred, for example to signal a system user that the system is operating. Depending on the embodiment, a signaling element may be configured to signal contact with salivary fluid or beverage fluid at a specific time point or after a preset period of time. Depending on the embodiment, a signaling element may be configured to signal lack of contact with salivary fluid or beverage fluid, or insufficient contact, at a specific time point or after a preset period of time. For example, at least one signaling element may be configured to signal contact with fluid relative to at least one of time, presence of a target material, or presence of amount of a target material. For example, a signaling element may include a timekeeping device operably attached to a fluid sensor and a signal emitter, so that a user would be alerted that fluid had or had not been detected during a preset period of time. For example, a signaling element may be operably attached to a sensor so that the sensor will cause a signal to be generated when a substance is present or absent after a preset period of time. For example, a signaling element may be operably attached to a sensor and configured to generate a signal when the sensor has detected a quantity of the substance after a particular period of time. In some embodiments, the substance may be the biological analyte while in some embodiments the substance may be discrete from the biological analyte. For example, the substance may be water, and the signaling element may be configured to emit a signal when more than a threshold level of water has been detected in fluid. Such a situation may occur, for example, when the sensor is able to detect only beverage fluid and not salivary fluid. For example, the substance may be an allergen, and the signaling element may be configured to emit a signal when more than a threshold level of allergen has been detected in beverage fluid. Such a situation may alert a system user to suspend drinking of the beverage. A signaling element may include a user-detectable chemical, such as a dye, odorant, ink, chromogen, fluorogen, or flavorant. A signaling element may include an emulsion covering a user-detectable chemical, such as a carbohydrate emulsion that is configured to dissolve after sufficient contact with fluid and release a user-detectable chemical. A signaling element may include an electronic moisture sensor coupled with a signal emitter.

Figure 6:
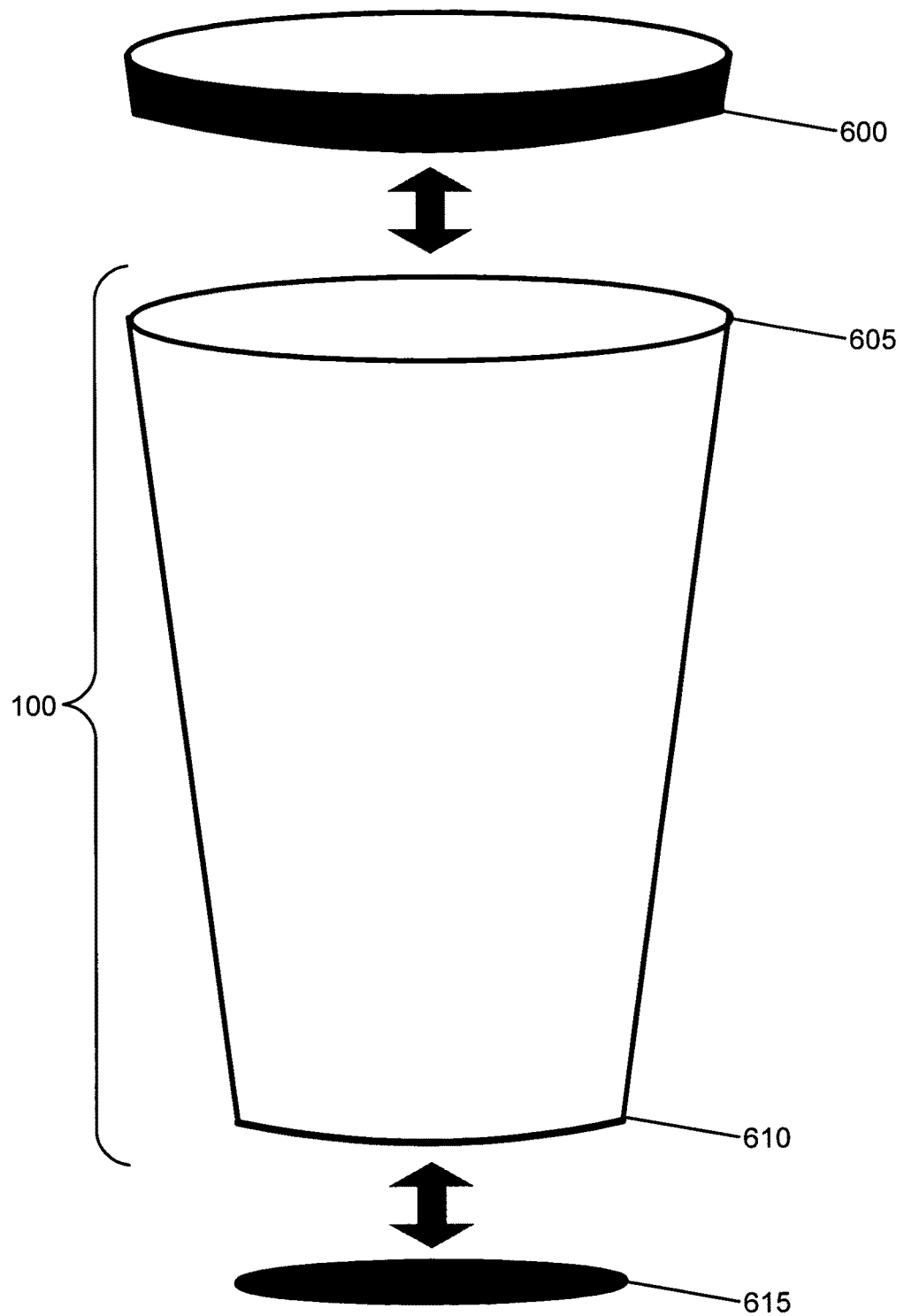
FIG. 6 illustrates a beverage container including modules.

FIG. 6 depicts embodiments of modules of a beverage container 100. A beverage container 100 may include modules configured to be replaceable or removable. For example, a beverage container 100 may include a module of one function that may be swapped with a module of a different function. For example, a module may be configured for removal and replacement with a new module or refurbishment and replacement of the original module. As illustrated in FIG. 6, in some embodiments a beverage container 100 with vessel walls, a top rim on the vessel walls 605 may be configured to attach to a rim extension module 600. A rim extension module 600 may include, for example, one or more sensors. As shown in FIG. 6, a rim extension module 600 may be configured to be removable from the top rim of the vessel walls 605, for example for replacement or renewal. FIG. 6 also illustrates that some embodiments may include a vessel base extension module 615 configured to detachably couple with the base end of the vessel walls 610. A vessel base extension module 615 may include, for example, one or more sensors. As shown in FIG. 6, a vessel base extension module 615 may be configured to be removable from the base end of the vessel walls 610, for example for replacement or renewal. Either a rim extension module 600 or a vessel base extension module 615 may include, for example, adhesive, suction devices, or screw-type threading to allow for their operable attachment and detachment from a beverage container 100. For example, a rim extension module 600 may include gaskets configured to hold the rim extension module in place at the top edge of the vessel walls. For example, a vessel base extension module 615 may include screw-type threading which corresponds with mating threading in the vessel walls, and such be configured to be detached and replaced on the vessel by twisting. Other modules of a beverage container 100 may include regions of a vessel wall, a partial or complete lid, a cover, or a drinking straw. For example, multiple drinking straws configured for use with an individual-use beverage container 100 may be used by different persons drinking from the beverage container 100 at distinct times, such as in series. Modules may also include sterile packaging configured for at least a portion of the system. For example, sterile packaging may be configured for envelopment of the beverage container 100 or a part thereof. For example, sterile packaging may be configured to cover the entire beverage container 100, or a part such as a lid or straw. Modules may also include an encapsulating material, such as a material encapsulating the sensor, sensing device, or region configured for drinking. An encapsulating material may be configured to dissolve or disperse after contact with a fluid, for example.

A beverage container 100 may include one or more display, such as a display configured to respond to detection of a substance by a sensor. For example, a sensor unit may include a display layer including colored material such as ink or dye that is released when a substance is detected by the sensor. For example, a beverage container 100 may include a light display, such as a light emitter configured to display a group of lights. A display may include, for example, a color indicator, words or symbols, or other meaningful patterns such as a barcode.

A beverage container 100 may include a provided agent, such as a taggant or agent that is configured to be metabolized by physiologic activity of a person drinking from the beverage container 100. The sensor included with the beverage container 100 may be configured to detect a biological analyte that is a metabolite of the provided agent. The metabolite of the provided agent may be of a type that is indicative of a metabolic state.

In some embodiments, materials may be retained in a beverage container 100 in a module configured for release of the material. The release may be passive or active, and it may be a responsive release. The beverage container 100 may include at least one gel configured to responsively release at least one medicinal agent. In some embodiments, materials may be retained in a reservoir associated with the beverage container 100, such as a reservoir configured to responsively release one or more medicinal agent. The beverage container 100 may include at least one reservoir configured to release at least one medicinal agent. Compounds configured to be released from a beverage container 100, may include, for example, one or more medicine like an expectorant, a bronchodilator, a cough suppressant, a vasodilator, an analgesic, an anti-septic, an anti-infective, an antibiotic, a nutritional supplement, or a therapeutic; a substrate for a metabolic enzyme; and/or a substance able to be physiologically incorporated as through ingestion or inhalation. A substance able to be physiologically incorporated may include a diagnostic challenge like metacholine or an allergen, or may be an agent like dextrose or urea that is useful in testing the metabolic activity of the body or an infecting pathogen. See, for example, Pathak et al., Ibid, which is incorporated herein by reference.

An example of a sensor 120 includes a polymerized crystalline colloidal array responsive to a substance. For example, a sensor may be fabricated to include a crystalline colloid array comprised of charged polystyrene spheres that are polymerized within a hydrogel that swells or shrinks in response to a substance (e.g. see Holtz and Asher, "Polymerized colloidal crystal hydrogel films as intelligent chemical sensing materials," Nature 389: 829-832 (1997) which is herein incorporated by reference). See, for example, U.S. Pat. Nos. 6,187, 599 and 6,544,800 to Asher et al., titled "Polymerized crystalline collidal arrays," and U.S. Pat. No. 7,105,352 to Asher titled "Intelligent polymerized crystalline colloidal array carbohydrate sensors," which are herein incorporated by reference. The Asher group at the University of Pittsburgh has also described the fabrication of polymerized crystalline colloidal arrays. See the attached printout of the Asher Laboratory materials titled "Colloid Group," accessed online at the Asher Laboratory website on Mar. 9, 2009, which are incorporated herein by reference. Crystalline colloidal arrays diffract light at (visible) wavelengths determined by their lattice spacing, which gives rise to intense colors. Swelling of the hydrogel including the polymerized crystalline colloid array changes the lattice spacing and causes a shift in the Bragg peak of diffracted light to longer wavelengths. The crystalline colloidal array further includes a recognition element, such as an antibody, which specifically recognizes and binds a substance (see, e.g., Holtz and Asher, "Polymerized colloidal crystal hydrogel films as intelligent chemical sensing materials," Nature 389: 829-832 (1997) and U.S. Pat. No. 6,753,191 to Asher and Reese, titled "Polymerized crystalline colloidal array chemical sensing materials for use in high ionic strength solutions" and U.S. Pat. No. 6,214,546 to Asher et al., titled "Detection of biomolecules," which are herein incorporated by reference). The beverage container 100 may be configured so that a color change in the crystalline colloid array of the sensor is visible to an individual user. To measure the peak diffraction wavelength, the beverage container 100 including the sensor is screened with a spectrometer associated with a external device. For example, the external device includes an integrated spectral sensing system having an energy (light) source and a detector (see e.g. U.S. Patent Application 2008/0265146 to Coates, titled "Integrated sensing module for handheld spectral measurements," and U.S. Pat. No. 7,459, 713, to Coates, titled "Sensing system approach for handheld spectral measurements having a disposable sample handling apparatus," which are herein incorporated by reference). The shift in peak diffraction wavelength may be correlated with substance concentration (see Holtz et al, Ibid.), and the results processed by circuitry in the external device. Results may recorded as digital memory in the external device, an associated network, and/or an additional device (such as a laptop or PDA). Results may be communicated to a system user, such as through an indicator on a user interface integral to the external device.

Figure 7:
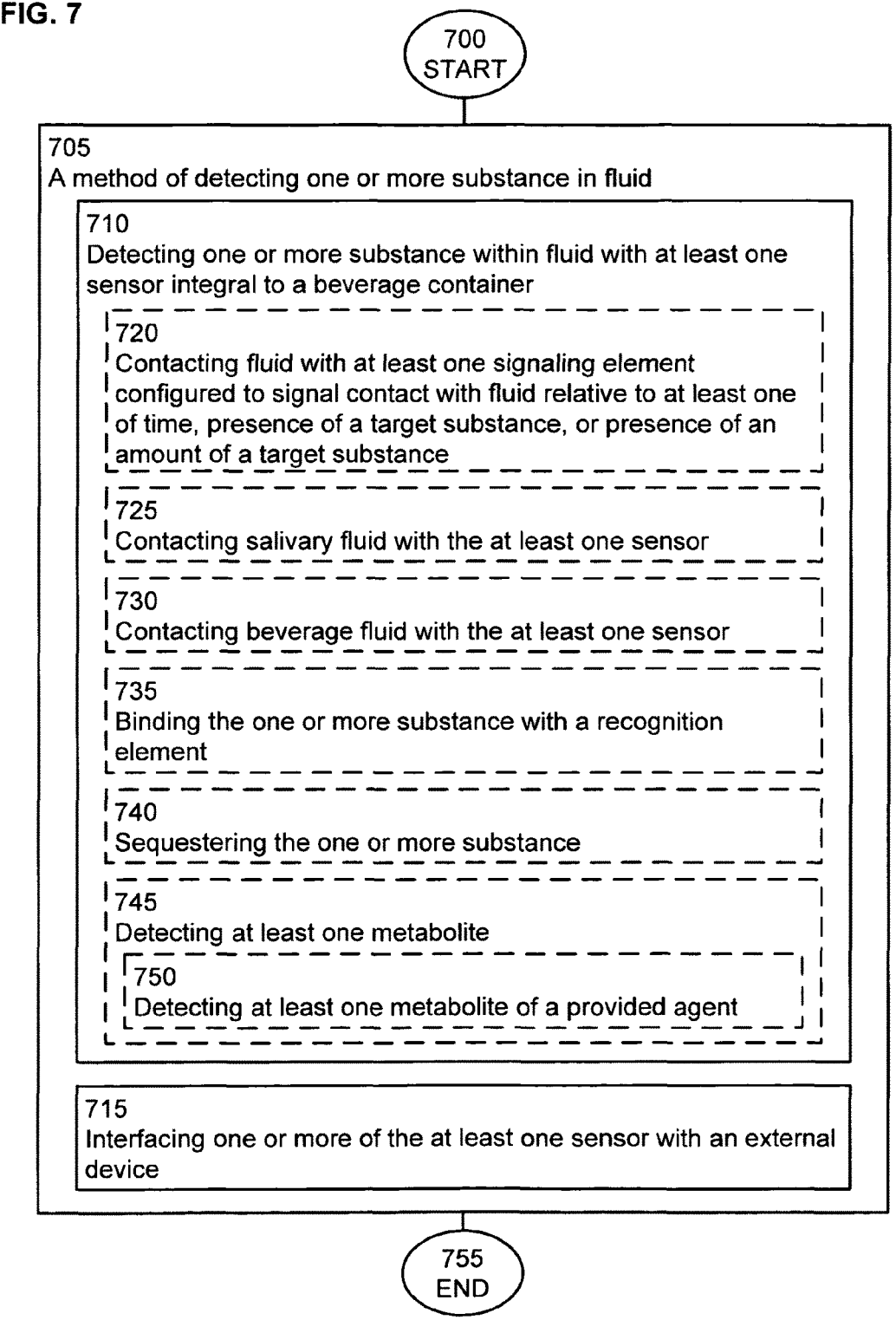
FIG. 7 illustrates a flowchart of a method.

FIG. 7 illustrates a flowchart of a method. The start of the method is depicted as block 700. Block 705 shows that the method is a method of detecting one or more substance in fluid. Block 710 depicts detecting one or more substance within fluid with at least one sensor integral to a beverage container. For example, one or more substance within salivary fluid or beverage fluid may be detected with a sensor included in a drinking vessel. Block 715 illustrates interfacing one or more of at least one sensor with an external device. For example, the sensor region of a beverage container may be placed adjacent to or in physical contact with an external device. For example, an external device may be attached to a beverage container with a positioning element. For example, a beverage container may be placed on a table or bar top including an integrated external device. The end of the method is depicted as block 755. The method flowchart may also include one or more optional blocks 720, 725, 730, 735, 740, 745, or 750. Block 720 shows contacting fluid with at least one signaling element configured to signal contact with fluid relative to at least one of time, presence of a target substance, or presence of an amount of a target substance. Block 725 illustrates contacting salivary fluid with the at least one sensor. For example, the sensor may be positioned to come into contact with salivary fluid when a person drinks from the beverage container. Block 730 depicts contacting beverage fluid with the at least one sensor. For example, the sensor may be positioned to come into contact with beverage fluid within the beverage container. Block 735 shows binding the one or more substance with a recognition element. For example, the one or more substance may be bound to a recognition element within a matrix structure integral to the sensor. Block 740 illustrates sequestering the one or more substance. For example, the one or more substance may be sequestered within a matrix structure within the sensor. Block 745 depicts detecting at least one metabolite. For example, a method may include detecting at least one metabolite of a biological analyte. For example, a method may include detecting at least one metabolite of a provided agent. For example, a method may include detecting at least one metabolite of a substance provided with a beverage. Block 745 may include block 750. Block 750 depicts detecting at least one metabolite of a provided agent. For example, a system may release a provided agent into beverage fluid from a reservoir integral to the beverage container and a sensor may be configured to detect a metabolite of the provided agent.

Figure 8:
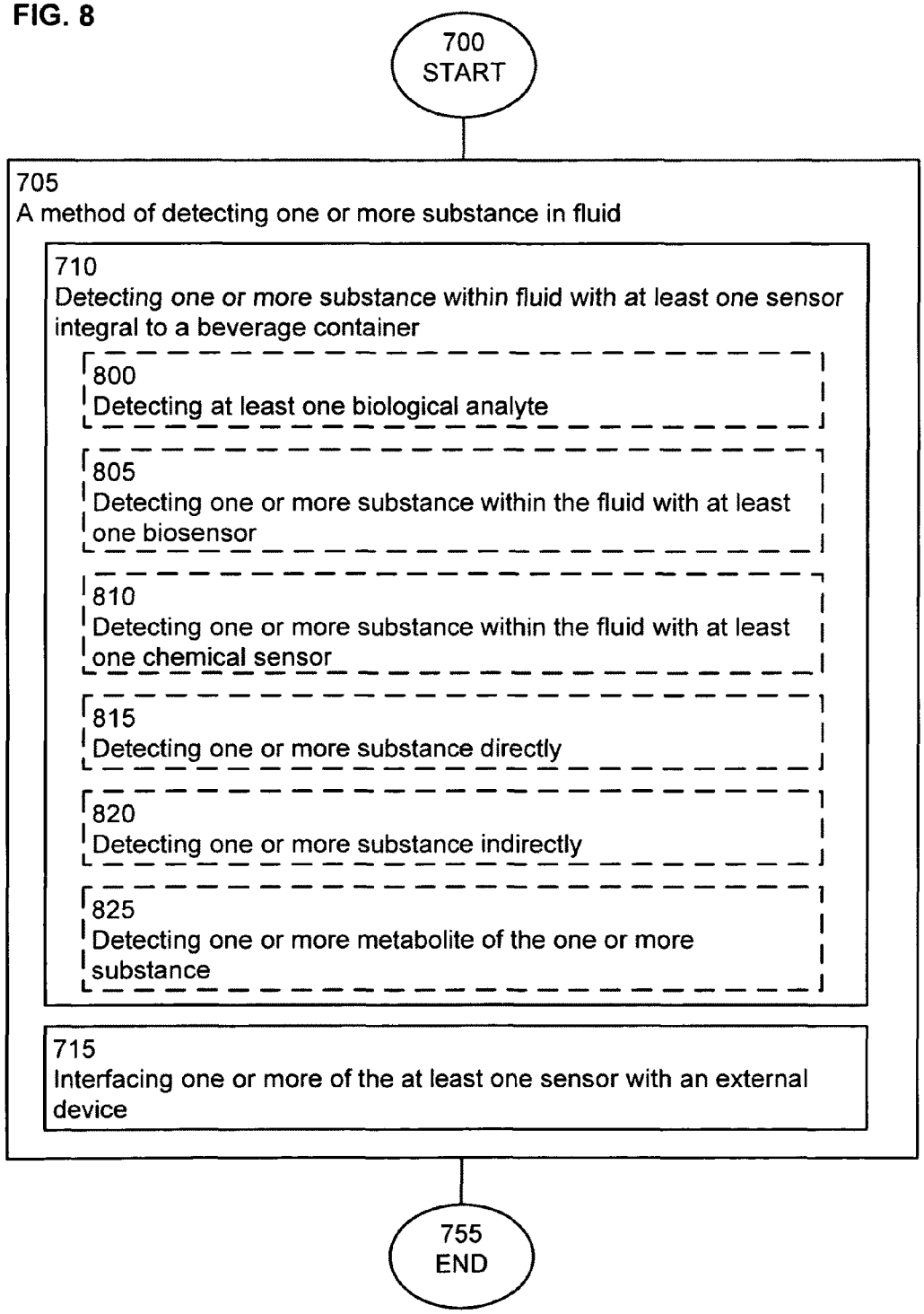
FIG. 8 depicts a flowchart of a method.

FIG. 8 illustrates other aspects of the method flowchart shown in FIG. 7. The flowchart may include one or more optional blocks 800, 805, 810, 815, 820, and 825. Block 800 shows detecting at least one biological analyte. For example, a method may include detecting at least one biological analyte originating in the oral cavity of an individual user. Block 805 depicts detecting one or more substance within the fluid with at least one biosensor. For example, an substance may bind to a biosensor component of a sensor, such as a biosensor containing genetically engineered cells configured to detect a substance through a receptor and then to produce a bioluminescent signal. The bioluminescent signal may be detected by an external device, such as a remote device, for example through a communication port configured to allow transmission of the bioluminescent signal. Block 810 illustrates detecting one or more substance within the fluid with at least one chemical sensor. For example, the sensor may detect a chemical agent, such as a pollutant, allergen or additive. Such a chemical agent may be undesirable or dangerous for consumption by some or all individuals. A method may also include detecting one or more substance within the fluid with at least one biological sensor. Block 815 shows detecting one or more substance directly. For example, a component of a sensor, such as a recognition element or part of a matrix, may bind a biological analyte directly. Block 820 depicts detecting one or more substance indirectly. For example, a sensor may be responsive to a taggant, which may be configured to be detectable in the presence of one or more substance. For example, a sensor may be configured to be responsive to a taggant bound to a substance. Block 825 illustrates detecting one or more metabolite of the one or more substance. For example, a sensor may be responsive to a metabolite of the substance, which may be a biological analyte.

Figure 9:
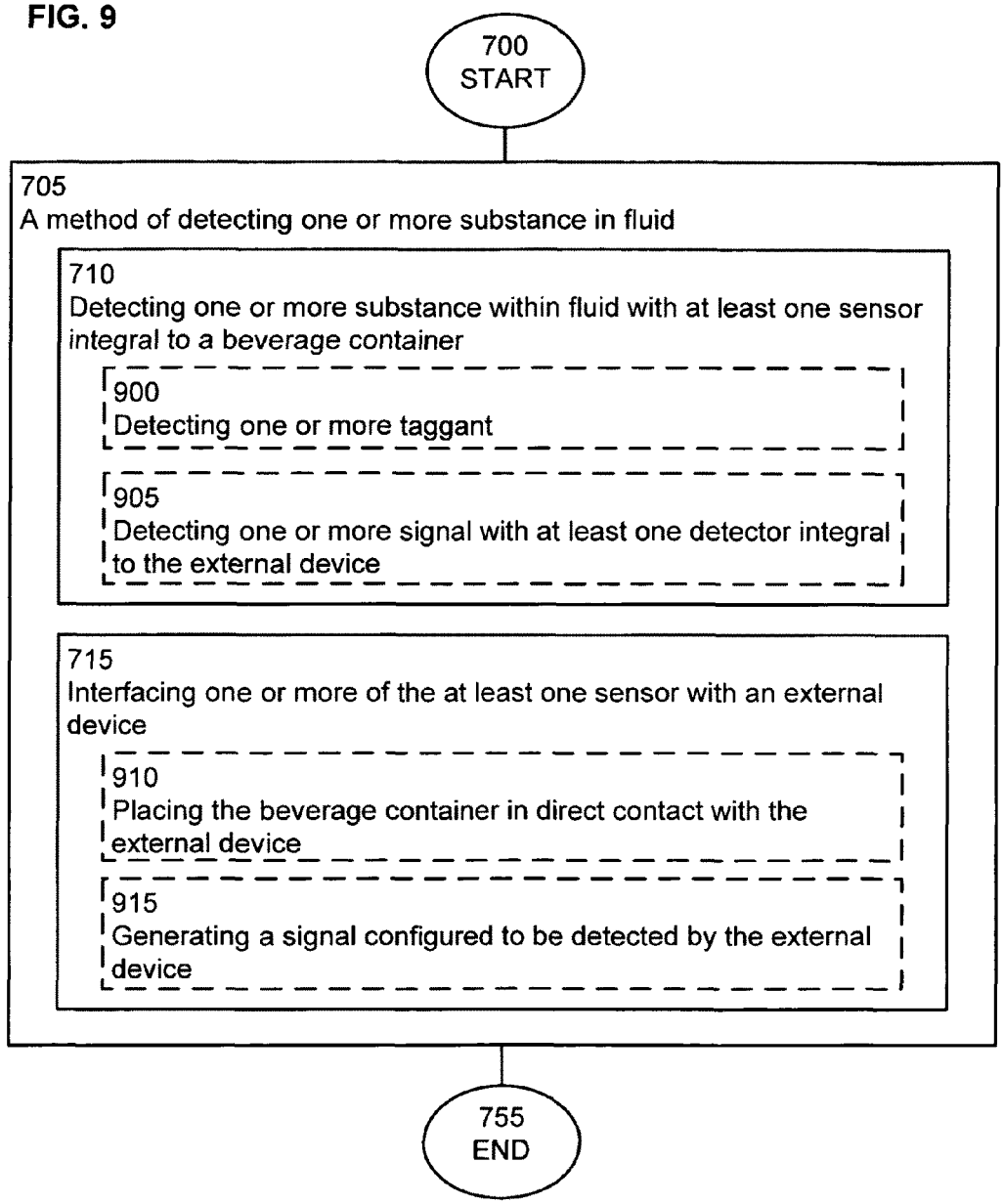
FIG. 9 shows a flowchart of a method.

FIG. 9 shows other aspects of the method flowchart shown in FIG. 7. Block 710, illustrating detecting one or more substance within fluid with at least one sensor integral to a beverage container, may include one or more optional blocks 900 and 905. Block 900 shows detecting one or more taggant. For example, a taggant may be of a type that is released and emits fluorescence when a substance binds to a recognition element. Block 905 depicts detecting one or more signal with at least one detector integral to the external device. For example, a detector may emit a certain wavelength of light and detect corresponding fluorescent signals from within a sensor. For example, a detector may detect an IR, auditory or vibratory signal emitted from electronic component of a sensor after a substance binds to the sensor. Block 715, depicting interfacing one or more of the at least one sensor with an external device, may include one or more of optional blocks 910 and 915. Block 910 shows placing the beverage container in direct contact with the external device. For example, the beverage container may be placed on or next to the external device, or the beverage container may have the external device hung or clipped on to a vessel wall with a positioning element. Block 915 illustrates generating a signal configured to be detected by the external device. For example a signal may be communicated through a cord, wire, or a cordless signal emitter such as IR, wireless, light or sound waves.

Figure 10:
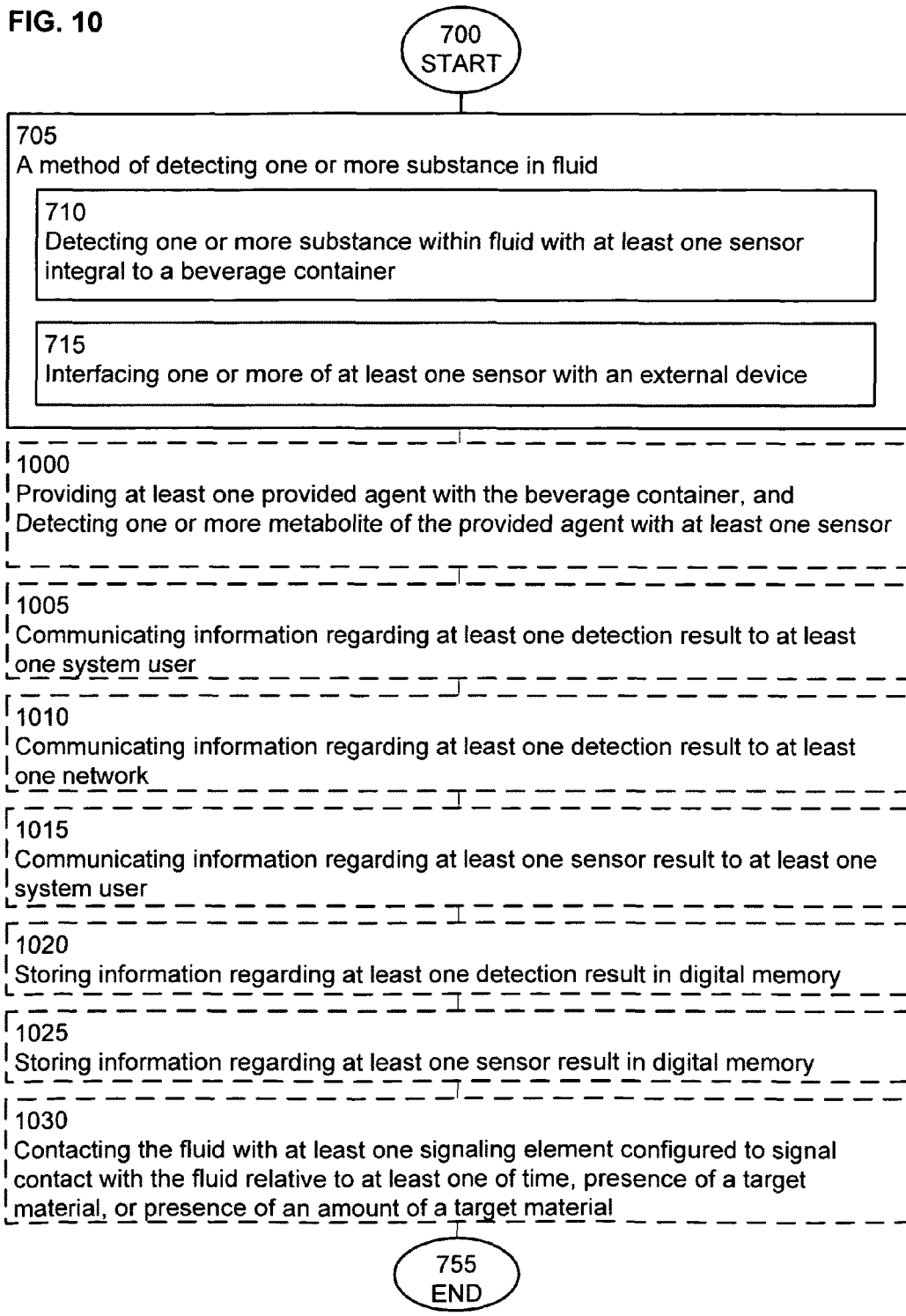
FIG. 10 depicts a flowchart of a method.
Figure 12:
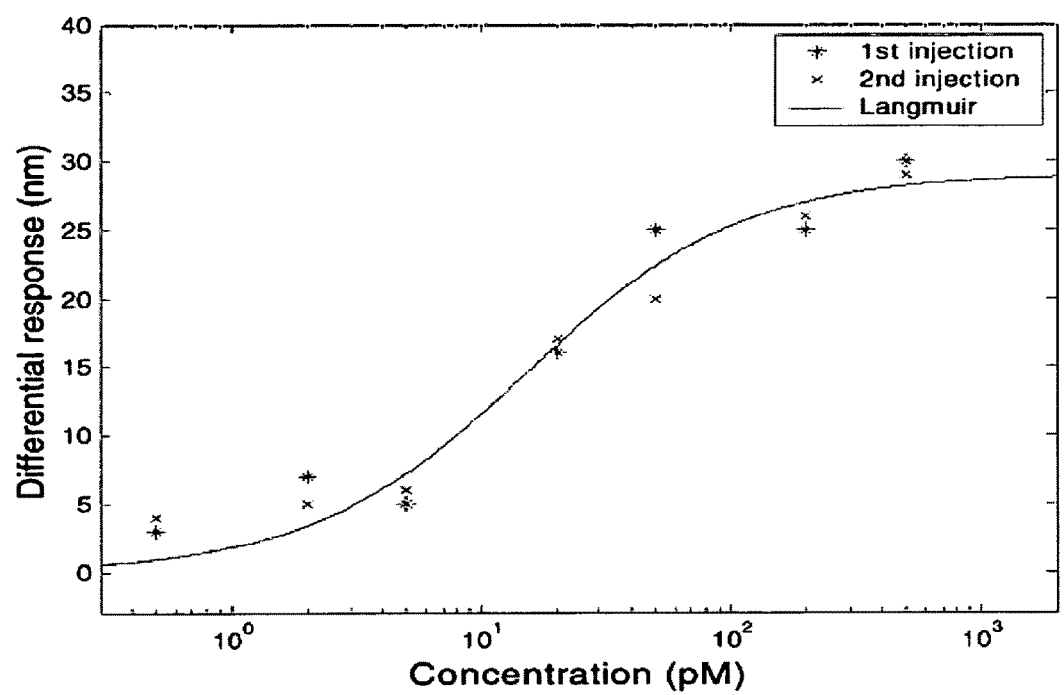
FIG. 12 depicts variation of aptamer/micro-cantilever deflection with Taq DNA polymerase concentration.

FIG. 10 depicts some aspects of the method flowchart shown in FIG. 7. In some embodiments, a flowchart may include one or more optional blocks 1000, 1005, 1010, 1015, 1020, 1025, or 1030. Block 1000 illustrates providing at least one provided agent with the beverage container, and detecting one or more metabolite of the provided agent with at least one sensor. For example, urea may be provided with the beverage container and at least one sensor may detect metabolites of urea, such as those produced by *H. pylori* pathogens resident in an individual's gastrointestinal system. In some methods, a provided agent may be provided with the system distinctly from the beverage container. Block 1005 shows communicating information regarding at least one detection result to at least one system user. For example, information may be communicated via an indicator, a display, an auditory signal or a lighted symbol. Block 1010 depicts communicating information regarding at least one detection result to at least one network. Block 1015 illustrates communicating information regarding at least one sensor result to at least one system user. Block 1020 shows storing information regarding at least one detection result in digital memory. Block 1025 depicts storing information regarding at least one sensor result in digital memory. For example, information regarding at least one detection result or at least one sensor result may be stored in digital memory within an external device, a computing device, or an associated computing network. Block 1030 illustrates contacting the fluid with at least one signaling element configured to signal contact with the fluid relative to at least one of time, presence of a target material, or presence of an amount of a target material.

Various components of the systems described herein may be implemented in a variety of materials depending on the specific embodiment. For example, a beverage container 100 may be fabricated from glass, plastic, metal or composite. For example, an external device may be integrated into another device, such as a laptop, phone, or PDA for easy portability. Criteria that may be relevant to the selection of component materials may include, for example, expense, durability, mass, chemical resistance, stability, and thermal resistance at a relevant temperature range.

Systems and methods as described herein may be used in a variety of ways and for a variety of purposes. The information gained from systems and methods as described herein may be used to determine a physiologic status of the individual user, for example a state related to cancer; lung function; infection; a metabolic state; the immune system, including a dysfunctional immune system experiencing autoimmunity, hyperimmunity, allergic reactions, or a depressed/suppressed immune system; the cardiac system, like levels of cardiac electrolytes or blood chemistries including cholesterol; a state related to environmental exposure; a risk state; pregnancy; fertility; or therapeutic response like to medicine or diet. In addition to the health of an individual, the habits and exposure of an individual may be monitored by detecting biological analytes such as a controlled substance, a pollutant, an ingested substance, an inhaled substance, an adsorbed substance, and an environmental effect. Monitoring may be implemented routinely, as on a daily or weekly schedule, for instance using the same components everyday to test for, fertility-associated metabolic factors such as hormones. Or, the system may be utilized including the components in an alternate but routine fashion, replacing part of the system at each use. For instance, each day of the week a different test could be performed for a different biological analyte. Or, an occasional test could be performed as desired, for example to consider possible infection or pregnancy.

Systems and methods as described herein may be used in a variety of ways and for a variety of purposes. The information gained from systems and methods as described herein may be used to determine a state related to environmental exposure, a risk state, or therapeutic response such as to medicine or diet. In addition to the health of a user, the habits and exposure of an individual may be monitored by detecting substances such as controlled substances, pollutants, allergens, ingested substances, inhaled substances, or adsorbed substances. Furthermore, substances indicative of an environmental effect may be detected. Monitoring may be implemented routinely, such as on a daily or weekly schedule, for instance using the same components every day to test, for example, for allergens or contraindicated substances. A specific user may utilize components of the system in an individualized fashion, for example a person wishing to minimize their exposure to a specific substance otherwise not found objectionable by the general public may test their own beverages prior to drinking. For example, a diabetic may monitor glucose in their beverages. For example, ethanol may be monitored in beverages intended for people such as children or individuals contraindicated for ethanol consumption. Or, the system may be utilized including the components in an alternate but routine fashion, replacing part of the system at each use. For instance, each day of the week a different test could be performed for a different substance. Or, an occasional test could be performed as desired, for example to consider possible exposure to infection.

Systems and methods as described herein may be implemented by individual users and the resulting data incorporated into a larger network, for example a public health or medical network. For example, information from multiple sensors configured to detect the same substance as used by multiple independent individual users may be integrated into a network to detect, track or monitor exposure of a number of individuals to a substance. Such monitoring may be routine or implemented on an as-needed basis, for example in situations where there is concern of contamination of a beverage fluid or as needed to monitor biological analytes originating from a number of individuals.

Other aspects of the systems and methods described herein are described in the examples below.

EXAMPLES

Example 1

A system incorporating a beverage container that detects, quantifies and indicates the amount of glucose (and other carbohydrates) in a beverage is useful to diabetes patients and to the general population to control dietary intake of glucose in beverages. A beverage container is constructed with a glucose sensor in a vessel wall that indicates the concentration of glucose in a beverage (e.g. in mg/ml). When glucose is detected, the beverage container signals the individual directly (such as through color change detectable through visual inspection, light flashing, or vibration) or indirectly through an external device. A computer system or network accepts a signal including information regarding the detected concentration of glucose, and calculates the amount of glucose in the beverage based on the detected concentration and records the value as well as indicating whether the amount falls within or outside an individual's preset criteria. A range of sensor modules are arranged along the vessel wall vertically, and the computer system or network uses internal logic processing to calculate the volume of beverage based on which sensor module(s) in the vertical array detect a glucose-containing beverage. Therefore in combination with information regarding glucose concentration the system calculates an estimated total glucose present, and indicates to an individual user if this amount of glucose falls outside or inside a preset range of values.

At certain times, individual users, including diabetic patients, require a beverage with a moderate amount of glucose (e.g. typically 15-20 grams of carbohydrate) to prevent or to treat mild hypoglycemia (low blood glucose). Hypoglycemia is often associated with insulin therapy used to treat Type I diabetes. Individual users may also wish to control their intake of glucose as part of a diet plan to treat or prevent obesity and/or hyperglycemia. A beverage container system detects and quantitates glucose in all beverages prior to consumption, and based on preset criteria, medical data, systemic glucose levels advises the individual user regarding the cumulative total glucose consumed (e.g. over the last week, 2 days, 24 hours, 16 hours, 4 hours, 1 hour, 30 minutes, etc.) to allow the individual to quantify and limit the amount of glucose ingested. A beverage container system with a horizontal array of glucose sensors and an external device is configured to transmit information regarding the detected glucose concentration and beverage volume, from the detector to a computer system and/or a network. A computer system and/or a network receives this data, calculates glucose amounts and compares them to stored criteria based on, for example, an individual user's medical record, (e.g. diet, weight, diabetes markers, age) and/or population averages of standard of care values (e.g. body mass index (BMI), fasting glucose levels, lipid levels, insulin response, target caloric intake). The device may then signal the individual user as indicated, such as "don't drink" or "do drink" the beverage.

A beverage container with a glucose sensor and a volume sensor is constructed from rigid plastic with a vertical row of glucose sensor modules along the vessel wall. A glucose sensor is constructed from a glucose-responsive hydrogel containing fluoroaminophenylboronic acid as the molecular recognition agent configured with a photonic crystal PCCA to diffract visible wavelength light. The hydrogel is configured to change diffraction wavelength in response to changes in the concentration of glucose at levels as low as 1 micromole/L. A photonic crystal polymerized crystalline colloidal array (PCCA) is synthesized by free radical solution polymerization using 2,2-diethoxyacetophenone (DEAP, 98%, Acros Organics, Geel, Belgium)(see Ben-Moshe et al, "Fast responsive crystalline colloidal array photonic crystal glucose sensors," *Anal. Chem.* 78: 5149-5157 (2006) which is herein incorporated by reference). A hydrogel comprised of acrylamide, n-hexyl acrylate and crosslinker bisacrylamide is polymerized with 145 nm polystyrene colloidal particles by irradiation with UV light at 365 nm and a glucose recognition agent such as a boronic acid derivative (e.g. 5-amino-2-fluorophenylboronic acid, available from Asymchem, Morrisville, N.C.) is attached to the polymer backbone. Detailed methods and materials are available in Ben-Moshe et al, Ibid., and U.S. Pat. No. 7,105,352 to Asher et al., titled "Intelligent polymerized crystalline colloidal array carbohydrate sensors," which are herein incorporated by reference.

A beverage container with a glucose-responsive PCCA detects and indicates the level of glucose present in a beverage by binding α-D-glucose, causing the hydrogel to shrink and reducing the diffraction wavelength, i.e. a blue shift in visible light wavelength. At glucose concentrations (ranging from 1 micromole/L to 20 millimole/L) a PCCA signals by a color change, visible to the naked eye, or by a shift in the peak diffraction wavelength measured with an external device that includes as a detector a spectrometer. For example, a portable visible/near infrared spectrometer with a wavelength range of 350-1000 nm, such as is available from Ocean Optics Inc., (Dunedin, Fla.), associated with a table and adjacent to the wall of the beverage device. For example, in the absence of glucose, a glucose-responsive PCCA diffracts a 658 nm red light (see Alexeev et al, "Photonic crystal glucose-sensing material for noninvasive monitoring of glucose in tear fluid," Clinical Chemistry, 50: 2353-2360 (2004) which is herein incorporated by reference). In 100 micromole/L glucose, the PCCA diffracts 615 nm orange-reddish light; in 400 micromole/L glucose, it diffracts 569 nm yellow-green light; in 1 mmole/L glucose, it diffracts 523 nm green light; in 4.5 mmole/L, it diffracts 449 nm blue light; and in 10 mmole/L glucose, it diffracts violet 424 nm light. Using a glucose-responsive PCCA, a shift in the peak diffraction wavelength for beverages versus water or a buffer can be correlated with glucose concentration (see FIGS. 11A and 11B and Alexeev et al, Ibid.). Color changes visible to the eye can serve as an indication to the user that the beverage is safe to ingest or as a warning that glucose levels are outside preset criteria. Also, the system can signal the user if the beverage is within a preset range of acceptable or unacceptable amounts of glucose.

FIG. 11 depicts the effect of glucose concentration on diffraction of a glucose-responsive PCCA sensor in 2 mmole/L glycylglycine (pH 7.4)-150 mmole/L NaCl. Taken from Alexeev et al, Ibid. FIG. 11A illustrates diffraction intensity (vertical axis) versus diffraction wavelength (horizontal axis) for different concentrations of glucose. Glucose concentration (millimole/L) is shown at the top of the diffraction peaks (a.u., absorbance units). FIG. 11B shows diffraction peak shift/nm (nanometer) on the vertical axis relative to glucose/(mmole/L) on the horizontal axis.

In addition, the beverage container system also includes a Brix infrared sensor including infrared detectors and optical filters configured to allow measurement of infrared light adsorption by fructose, glucose, sucrose and other sugars. An instrument, associated with the table or with the external device housing the spectrometer, includes an infrared light source (for example, a total attenuated reflection crystal) as a Brix infrared detector is used to irradiate the beverage container and beverage, and the resulting light adsorption is detected by the external device. Brix infrared sensors with a measurement range of 0-999 mg/L for carbohydrates and 0-20° Brix (equivalent to approximately 0-200 mg/mL of sucrose) are available from VitalSensor Technologies LLC, (Acton, Mass.) (see the article titled, "VS-1000B Series Inline Brix Sensors for the Beverage Industry; Inline Networked Smart Infrared Sensors for Real-Time Process Monitoring: Continuous Accurate Brix measurement of Regular and Diet Beverages" 2008, pages 1-4, which is herein incorporated by reference). Data on carbohydrate absorption of infrared wavelength light by a beverage is relayed by the Brix detector and to a computer system. The data from the Brix detector is then transformed by standard calculations to carbohydrate concentrations, and the resulting information combined with the glucose results. Based on individual information (e.g. criteria for carbohydrate consumption, salivary glucose levels, weight, diet, cumulative consumption) available on the network, a beverage container system will display recommendations such as reducing or eliminating the consumption of some beverages, or it can display recommendations such as increasing consumption of some beverages (e.g. in the case of hypoglycemia). Suggestions may be made to an individual using the beverage or to a system user such as a caregiver or medical professional.

Example 2

A beverage container system includes a beverage container configured with a glucose sensor in the lip or top of the beverage container (for example, see beverage container 100 including sensor 110 in FIG. 1) to detect glucose in salivary fluid. Noninvasive monitoring of systemic glucose levels is accomplished by sampling salivary fluid and calculating estimated blood glucose levels based on a correlation between glucose concentrations in salivary fluid and blood. For example, comparisons between venous blood glucose concentrations and salivary fluid glucose concentrations have demonstrated a correlation coefficient, $R^2$, equal to 0.87 (see U.S. Pat. No. 6,102,872 to Doneen, et al, titled "Glucose detector and method," which is herein incorporated by reference).

A beverage container system including a glucose sensor on the top rim of the vessel walls (e.g. sensor 110 in FIG. 1) including a glucose-responsive PCCA configured to diffract light at different wavelengths in response to different glucose concentrations is described above (Alexeev et al, Ibid.). Salivary fluid containing glucose passing over the glucose sensor during use of the beverage container causes the PCCA to contract and result in a shift in diffraction wavelength that is visible as a color change to the naked eye.

The glucose sensor including a glucose-responsive PCCA is housed in a module configured for removal from the beverage container and analysis in a spectrophotometer that is part of an external device, configured to measure the peak diffraction wavelength. Salivary fluid glucose concentrations, which range from approximately 0.5 milligrams/dL to approximately 5.0 milligrams/dL (see U.S. Pat. No. 6,102, 872 to Doneen, Ibid.), can be detected by a glucose-responsive PCCA configured to be sensitive to 0.018 milligrams/dL of glucose (e.g. Ben-Moshe et al., Ibid.). Information regarding visual color changes or peak diffraction wavelength data is sent from the external device and received by a computer system, which compares the salivary fluid glucose data to a standard curve to determine glucose concentration then calculates the systemic glucose levels. The beverage container computer system is connected to a network that receives, calculates and stores the salivary glucose concentration, calculated blood glucose concentration, time, date and other medical information (e.g. insulin injections, diet, weight) and indicates recommendations such as dispensation of insulin or other medications, glucose, exercise and/or contacting a caregiver or medical professional.

Example 3

A beverage container system is configured to detect human herpes viruses. Two human herpes viruses (HHV) typically infect orofacial regions and genital regions: HHV subtype 1, (HHV-1, a.k.a. herpes simplex virus type 1, HSV-1) predominantly infects the former; and HHV-2, the latter. HHV-1 and HHV-2 can also infect the central nervous system, especially in neonates, adolescents and adults, which can lead to encephalitis, morbidity and death. For each of these infections, early detection and/or diagnosis of HHV would be of tremendous value in preventing transmittal of HHV via contaminated beverages, glassware, food, saliva, perspiration, secretions and excretions. Early detection is of particular value since HHV-1 and HHV-2 can survive indefinitely in humans as latent infections that are asymptomatic yet contagious, due to viral shedding in saliva, secretions and mucocutaneous tissues. Early diagnosis of HHV-1 and HHV-2 would allow precautions to be taken with respect to sexual transmission, and alert individuals of the potential for herpesviral encephalitis.

Figure 13:
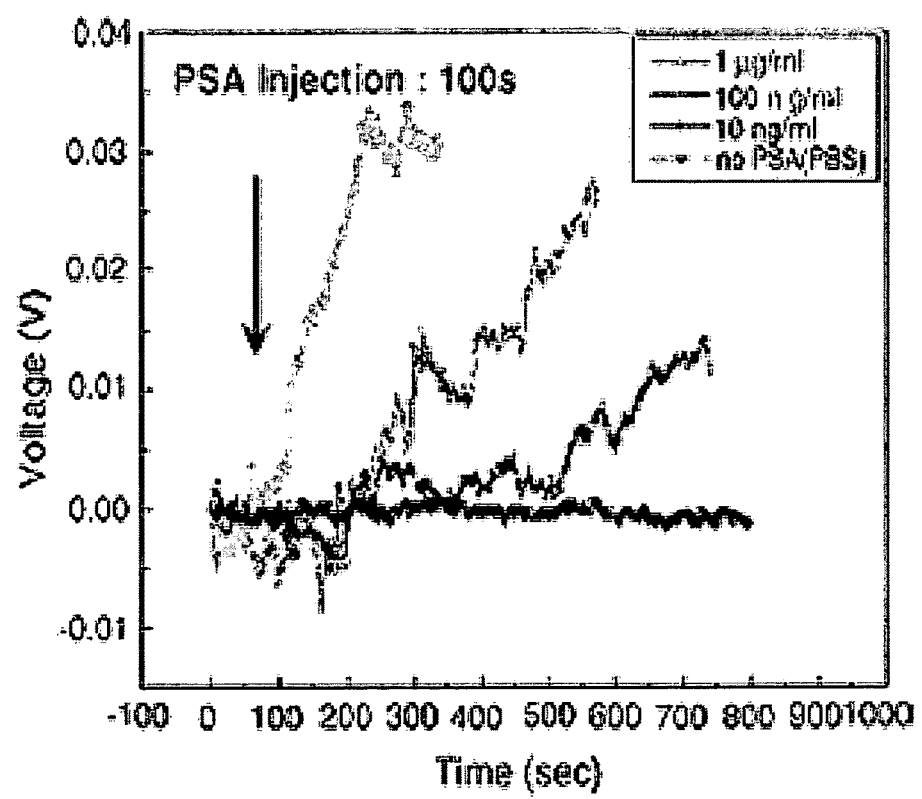
FIG. 13 illustrates the piezoresistive signal of a micro-cantilever as a function of PSA concentration.

A beverage container system including a human herpes virus (HHV) sensor operably connected to an external device, a computer system and a network detects a herpes virus in beverages, on beverage containers and in salivary fluid. A beverage container system configured to detect HHV-1 can, for example, be used to detect HHV-1 contaminating a beverage container, a nascent infection, or a previous infection. A beverage container system configured to detect HHV-1 can also or instead be used to monitor a persistent infection or to monitor viral shedding following treatment for HHV-1 infection in an individual user.

A beverage container including a HHV-1 sensor at the top rim of the vessel wall (for example, see beverage container 100 with vessel wall including sensor 110 in FIG. 1) is constructed with a recognition element to capture and detect HHV-1 viral particles. A HHV-1 sensor fabricated with a piezoresistive micro-cantilever including aptamers immobilized on its surface is used to detect HHV-1 viral particles. Aptamers are small RNA or DNA molecules that specifically bind small molecules, proteins, carbohydrates, and lipids with high specificity and high affinity. Piezoresistive micro-cantilevers are nanomechanical devices that detect small stresses applied to the cantilever and signal via a piezoresistive electrical response. For example, a piezoresistive micro-cantilever is fabricated from poly-silicon, silicon nitride, silicon dioxide, chromium and gold using standard silicon microfabrication techniques such as reactive ion etching, wet etching and deposition techniques (see Wee et al, "Novel electrical detection of label-free disease marker proteins using piezoresistive self-sensing micro-cantilevers," *Biosensors and Bioelectronics,* 20: 1932-1938 (2005) which is herein incorporated by reference). A micro-cantilever and a reference micro-cantilever (without an aptamer or other recognition molecule attached) are operably connected to additional components, such as a half Wheatstone bridge and other electronic components (e.g. DC power supply and multimeter, available from Agilent Technologies, Inc., Santa Clara, Calif.) and an amplifier (available from Analog Device, Inc., Norwood, Mass.: see Wee, et al., ibid) to allow differential measurement of resistance. Mechanical stress on a piezoresistive micro-cantilever results in changes in resistance and subsequently results in voltage changes. To detect HHV-1 viral particles, aptamers that recognize and bind a HHV-1 surface protein are attached to one face of the micro-cantilever. Aptamers that recognize a specific target can be obtained by in vitro selection from a library of oligonucleotides with random sequences (see Lee et al, "Aptamers as molecular recognition elements for electrical nanobiosensors," *Anal Bioanal Chem,* 390: 1023-1032 (2008) which is herein incorporated by reference). For detection of HHV-1, aptamers are selected that recognize HHV-1 glycoprotein B, a membrane and surface protein. Aptamers specific for HHV-1 are attached to one face of a microcantilever by depositing a 20 nm layer of gold (using an electron beam evaporator) and then reacting thiol-modified aptamers in solution with the gold surface. For example, a DNA aptamer, 51 nucleotides long and derivatized with a C6 thiol linker ($HS(CH_2)_6PO_4$) at its 5' end, is immobilized on a gold-coated surface by incubation of a 10 μM aptamer solution with the micro-cantilever for approximately 20 minutes (see Savran et al, "Micromechanical detection of proteins using apatmer-based receptor molecules," *Analytical Chemistry,* 76: 3194-3198 (2004) which is herein incorporated by reference). A reference micro-cantilever is manufactured by immobilizing a nonspecific, nonbinding DNA oligonucleotide using the same methods (see Savran et al, Ibid.).

Specific binding of HHV-1 viral particles mediated by glycoprotein B binding to an aptamer bound to the surface of the microcantilever causes mechanical stress and results in deflection of the micro-cantilever. To detect aptamer/micro-cantilever binding to HHV-1, a micro-cantilever and a reference micro-cantilever (with a nonspecific aptamer attached) are connected to a half Wheatstone bridge and other electronic components (e.g. DC power supply and multimeter available from Agilent Technologies, Inc., Santa Clara, Calif.) and an amplifier (available from Analog Device, Inc., Norwood, Mass.) to allow differential measurement of resistance. Mechanical stress on the piezoresistive micro-cantilever results in changes in resistance, which can be detected by a external device as voltage changes.

As further illustration of the detection of aptamer binding to micro-cantilevers, see FIG. 12, (taken from Savran et al, Ibid.). FIG. 12 depicts data from a micro-cantilever bound with an aptamer that specifically recognizes Taq DNA polymerase deflects up to approximately 30 nm in response to picomolar concentrations of Taq DNA polymerase. The graph depicts the differential response (in nm) on the vertical axis and concentration (in pM) on the horizontal axis. The graph illustrates the reproducibility of the method, with two sets of reactions including the same concentrations of Taq DNA polymerase shown as adjacent marks. FIG. 12 depicts variation of aptamer/micro-cantilever deflection with Taq DNA polymerase concentration. A Langmuir isotherm fit to the data revealed a $K_d$ of 15 pM.

As a further illustration of the detection of aptamer binding to micro-cantilevers, see FIG. 13 (taken from Wee et al, Ibid.). FIG. 13 illustrates that a piezoresistive micro-cantilever, including recognition molecules for prostate-specific antigen (PSA) immobilized on one face of the cantilever, deflects when PSA binds. Deflections of the micro-cantilever are detected as voltage changes that vary (kinetics and maxima) with PSA concentration. The graph depicts voltage detected (V) on the vertical axis relative to time (in seconds) on the horizontal axis. FIG. 13 illustrates the piezoresistive signal (voltage) of a micro-cantilever as a function of PSA concentration (curves left to right: 1.0 μg/ml, 100 ng/ml, 10 ng/ml, no PSA).

A beverage container system including a HHV-1 sensor including an aptamer specific for HHV-1 glycoprotein B immobilized on a micro-cantilever is configured to detect very low levels of HHV-1 particles (e.g. picomolar levels of protein antigens) and transmit an electronic signal to the system. Changes in voltage (see FIG. 13) are detected by a microcircuit integral to the beverage container. On detection, the microcircuit is configured to initiate illumination of a light-emitting diode (LED) on the container to indicate to the user that HHV-1 has been detected in his or her saliva. For example, relative to FIG. 13, voltages over 0.01 volts would trigger illumination of a miniature LED (rated at 30-60 milliwatts; available from SunLED Corp., Walnut, Calif.) on the beverage container indicating that an biological analyte is present. Processor-controlled LED systems that control LED illumination based on electronic signals received by the LED system are described in U.S. Pat. No. 6,528,954 to Lys and Mueller, titled, "Smart light bulb," which is herein incorporated by reference.

In addition or instead, an electronic signal regarding the change in voltage is sent wirelessly, for example by radiofrequency, to a computer system (for example see computer system 430 in FIG. 4B). The computer system is configured to use logic processing to compare the detected voltages with a standard curve correlating voltage with concentration of biological analyte (for example as shown in FIG. 13). The computer system signals to display an indicator of the presence of HHV-1 in salivary fluid and the approximate concentration of HHV-1 to a system user.

Example 4

A beverage container system is configured to monitor systemic medication levels, patient compliance and drug abuse. A beverage container system with a recognition element and a medication sensor detects the concentration of medications in salivary fluid and signals a user when medication levels are within or outside preset criteria based on the correlation between medication concentrations in salivary fluid and blood (serum or plasma). The beverage container system also signals an external device, which is configured to indicate the medication concentration to a caregiver. A beverage container system configured to detect and report medication levels is useful for patients who need to monitor their medication levels (e.g. individuals prescribed digoxin), as well as to caregivers or persons in authority who need to monitor patients and verify compliance with prescribed treatments (e.g. carbamazepine) or to monitor illicit "recreational" drugs (e.g. cocaine) or drug abuse (e.g. codeine). Such a beverage container system is also non-invasive, which may improve monitoring compliance in some individual users.

A beverage container system including one or more modular drug sensor configured to detect medications in salivary fluid is used to detect psychiatric medications and monitor patient compliance. For example, a beverage container system is configured to detect lithium, carbamazepine, ethosuximide phenobarbital, phenyloin, or theophylline in salivary fluid and indicate if preset criteria for drug concentration (i.e. therapeutic concentrations) are being maintained. Serum concentrations and salivary fluid concentrations have been shown to be highly correlated for: lithium (correlation coefficient, $r=0.87$); carbamazepine ($r=0.89$); phenobarbital ($r=0.98$); phenyloin ($r=0.97$); and theophylline ($r=0.85$). See Kaufman and Lamster, "The diagnostic applications of saliva—a review," *Crit. Rev. Oral Biol. Med.*, 13: 197-212 (2002) which is herein incorporated by reference. A beverage container system including one or more modular drug sensor can also be used to monitor drug abuse and recreational drugs. For example, amphetamines, barbiturates, opioids, cocaine, tetrahydrocannabinol, and nicotine can be detected in salivary fluid (Kaufman and Lamster, Ibid.) and the detected drug concentrations in saliva or the calculated drug concentrations in serum reported to caregivers or authorities. Although more details are given regarding the construction of a beverage container system for monitoring cocaine in an individual user's saliva (as below), similar methodologies may be implemented to fabricate beverage container systems configured to monitor other medications or drugs with a high correlation between serum concentrations and salivary fluid concentrations (e.g. see Kaufman and Lamster, Ibid.).

A beverage container system configured to monitor systemic medication levels for monitoring patient compliance and drug abuse is constructed with an electronic drug sensor including an aptamer configured to detect and signal the presence of cocaine in salivary fluid present on the lip of the beverage container. An aptamer that specifically binds cocaine with high affinity and high specificity is selected from a mixture (or pool) of oligonucleotides with random sequences by using an iterative process combining affinity chromatography and amplification termed Systematic Evolution of Ligands by EXponential enrichment (SELEX; see U.S. Pat. No. 5,475,096 issued to Gold et al., titled, "Nucleic acid ligands," which is herein incorporated by reference). Construction, selection and amplification of a single stranded, random sequence DNA pool containing approximately $2 \times 10^{14}$ different molecules is described in U.S. Pat. No. 5,631,146 issued to Szostak et al. titled, "DNA aptamers and catalysts that bind adenosine or adenosine-5'-phosphates and methods for isolation thereof," which is herein incorporated by reference. DNA ligands are selected by affinity chromatography with a matrix comprised of sepharose or agarose coupled to cocaine. Methods and materials for construction and use of an affinity chromatography matrix are given in Win et al., "Codeine-binding RNA aptamers and rapid determination of their binding constants using a direct coupling surface plasmon resonance assay," *Nucleic Acids Research*, 34: 5670-5682 (2006) which is herein incorporated by reference. Following each round of selection, amplification is carried out using the polymerase chain reaction as described (U.S. Pat. No. 5,631,146, Szostak et al, Ibid. and Win et al, Ibid.). Alternatively, an aptamer with high affinity for cocaine can be purchased from AptaRes, (D-15749 Mittenwalde, Germany).

Aptamers that signal electronically are created by mutagenesis of aptamers and by conjugation of an oxidation/reduction tag to the aptamer. See Stojanovic et al, "Aptamer-based folding fluorescent sensor for cocaine," *J. Am. Chem. Soc.*, 123: 4928-4931 (2001) and Baker et al, "An electronic, aptamer-based small-molecule sensor for the rapid, label-free detection of cocaine in adulterated samples and biological fluids," *J. Am. Chem. Soc.*, 128: 3138-3139 (2006), which are herein incorporated by reference. An aptamer configured to bind cocaine and result in a conformational change is created by a combination of site-specific and random mutagenesis as shown by Stojanovich et al, Ibid. Conjugation of a oxidation/reduction taggant such as methylene blue to an aptamer that undergoes a ligand-dependent conformational change will result in an aptamer that signals electrochemically when ligand binds. For example, conjugation of methylene blue (available from ScienceLab.com, Inc., Houston, Tex.) to an aptamer that changes conformation upon binding cocaine creates an electrochemical aptamer-based sensor that will transfer electrons in response to cocaine binding (see Baker, et al, Ibid.). A cocaine-specific aptamer conjugated with methylene blue is immobilized on a 1.6 mm diameter gold electrode (Bioanalytical Systems, Inc., West Lafayette, Ind.) by adding an alkanethiol group to the 5' end of the aptamer and reacting the derivatized aptamer-thiol with the gold surface (see Baker et al, Ibid. for methods and materials). The electrochemical response of the electronic aptamer cocaine sensor can be measured by alternating current voltammetry.

FIG. 14 illustrates the electrochemical response of a cocaine-responsive electronic aptamer sensor (taken from Baker et al, Ibid.). Detected increase in current following immersion of an electronic aptamer cocaine sensor in 500 µM cocaine is shown in FIG. 14A. FIG. 14A shows AC voltammograms of a cocaine-responsive electronic aptamer sensor. AC current (in nA) is illustrated on the vertical axis relative to potential (V vs. Ag/AgCl) on the horizontal axis. Upon addition of 500 µM cocaine, a signal increase is observed. The sensor was regenerated in buffer. FIG. 14B depicts the dose-response of the electronic aptamer sensor to cocaine. FIG. 14B depicts E-AB signal increase on the vertical axis relative to cocaine concentration (in µM) on the horizontal axis.

An electronic aptamer-based sensor configured to respond to cocaine is sensitive to less than 10 µM cocaine and exhibits a response curve (see FIG. 14B) that is informative to approximately 500 µM cocaine. Additional examples of aptamer-based electrochemical sensors for small molecules (e.g. nicotine), proteins (including thrombin and platelet-derived growth factor) and cells are as described in Lee et al, "Aptamers as molecular recognition elements for electrical nanobiosensors," *Anal. Bioanal. Chem.*, 390:1023-1032 (2008) which is herein incorporated by reference.

A beverage container including an electronic aptamer-based sensor in the lip of the container also includes a micro-voltammetric electrochemical sensor configured to measure changes in current when varying voltages are applied. Micro-fabricated electrochemical sensors are described in Liu et al, "Applications of microfabrication techniques in electrochemical sensor development," *Applied Biochemistry and Biotechnology*, 41: 99-107 (1993), which is herein incorporated by reference. When an individual user drinks from the beverage container, salivary fluid containing the biological analyte cocaine enters a chamber in the beverage container via capillary action and comes in contact with the electronic aptamer-based sensor for cocaine. The electronic signal detected by voltammetry is indicated with LED bulbs which are illuminated in response to an electronic signal. Alternatively or in addition, the electronic signal detected by voltammetry is transduced by circuitry into an RF signal and transmitted to and received by an external device such as a computer, or a cell phone. A computer system and network calculates the concentration of cocaine in salivary fluid and, by correlation, in blood serum based on previously established curves (see Kaufman and Lamster, Ibid and FIG. 14B herein). Information regarding salivary fluid and blood serum cocaine concentrations can be saved in the network and/or relayed to caregivers, authorities, and the individual user via indicators, such as a user interface, on the external device.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. For example, the optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled, implemented, translated, or converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

In a general sense, the various aspects described herein can be implemented, individually and/or collectively, by a wide range of hardware, software, firmware, and/or any combination thereof and can be viewed as being composed in part of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., operations), devices, objects, and the discussion accompanying them are used as examples for the sake of conceptual clarity and various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting. The foregoing specific exemplary processes and/or devices and/or technologies are representative of more general processes and/or devices and/or technologies taught elsewhere herein, such as in the claims filed herewith and/or elsewhere in the present application.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

It is common within the art to implement devices and/or processes and/or systems, and thereafter use engineering and/or other practices to integrate such implemented devices and/or or processes and/or systems into more comprehensive devices and/or processes and/or systems. That is, at least a portion of the devices and/or processes and/or systems described herein can be integrated into other devices and/or processes and/or systems via a reasonable amount of experimentation. Examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory. Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, recited operations therein may generally be performed in any order. Also, although various operational flows are presented in sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The various aspects and embodiments disclosed herein are for purposes of illustration and are not intended to be limiting, with the true scope and spirit being indicated by the following claims.

What is claimed is:

1. A beverage container comprising:
   a vessel body configured to hold a beverage, the vessel body defining a base and at least one side wall, the at least one side wall including a region defined by one of a color, shape, or texture different from a lateral remainder of the at least one side wall, the color, shape, or texture configured to encourage drinking from the region;
   at least one sensor secured to the at least one side wall within the region or embedded within the vessel body within the region, the at least one sensor including a sensor configured to detect and identify one or more substance in fluid and generate a signal that the identification has been made;
   a power source; and
   a circuit operatively connected to the at least one sensor and the power source;
   wherein one or more of a portion of the power source or a portion of the circuit are embedded in the at least one side wall.

2. The beverage container of claim 1, wherein the vessel body comprises:
   at least one signal emitter.

3. The beverage container of claim 1, wherein the vessel body comprises:
   at least one signaling element configured to signal contact with the fluid relative to at least one of time, presence of a target material, or presence of an amount of a target material.

4. The beverage container of claim 1, wherein the at least one sensor comprises:
   at least one signal emitter.

5. The beverage container of claim 1, wherein the at least one sensor comprises:
   at least one selective medium.

6. The beverage container of claim 1, wherein the at least one sensor comprises:
   at least one gel configured to be responsive when the one or more substance is detected.

7. The beverage container of claim 1, wherein the at least one sensor comprises:
   at least one recognition element.

8. The beverage container of claim 1, wherein the one or more substance comprises:
   an indicator of a physiological state.

9. The beverage container of claim 1, wherein one or more of the at least one sensor comprises:
at least one chemical sensor.

10. The beverage container of claim 1, wherein the at least one sensor includes a plurality of replaceable modules configured to detect and identify one or more substance in fluid, each of the plurality of replaceable modules being configured to sense a different substance via a different functionality for each of the plurality of replaceable modules.

11. The beverage container of claim 1, comprising:
one or more straw configured for drinking.

12. The beverage container of claim 1, comprising:
at least one transmucosal sampling mechanism.

13. The beverage container of claim 1, comprising:
one or more display.

14. The beverage container of claim 1, comprising:
sterile packaging.

15. The beverage container of claim 1, comprising:
one or more sensing device.

16. The beverage container of claim 1, comprising:
one or more taggant.

17. A system, comprising:
at least one beverage container including;
a vessel body defining at least one side wall;
at least one sensor secured to the at least one side wall or embedded within the beverage container, the at least one sensor configured to detect and identify one or more substance in fluid and generate a signal that the identification has been made, the at least one sensor including a plurality of replaceable modules configured to detect and identify one or more substance in fluid, each of the plurality of the replaceable modules being configured to sense a difference substance via a different functionality for each of the plurality of replaceable modules;
a power source; and
a circuit operatively connected to the at least one sensor and the power source;
wherein one or more of a portion of the power source or a portion of the circuit are embedded in the at least one side wall; and
at least one external device including at least one port configured for communication with the at least one sensor.

18. The system of claim 17, wherein the at least one beverage container comprises:
one or more drinking straw.

19. The system of claim 17, wherein the at least one beverage container comprises:
at least one signaling element configured to signal contact with the fluid relative to at least one of time, presence of a target material, or presence of an amount of a target material.

20. The system of claim 17, wherein the at least one beverage container comprises:
at least one selective medium.

21. The system of claim 17, wherein the at least one beverage container comprises:
at least one gel configured to be responsive when the one or more substance is detected.

22. The system of claim 7, wherein at least a portion of the at least one beverage container is modular.

23. The system of claim 17, wherein the at least one beverage container comprises:
at least one transmucosal sampling mechanism.

24. The system of claim 17, wherein the at least one beverage container comprises:
at least one encapsulating material.

25. The system of claim 17, wherein the at least one beverage container comprises:
at least one signal emitter.

26. The system of claim 17, wherein the at least one beverage container comprises:
one or more taggant.

27. The system of claim 17, wherein the at least one sensor comprises:
at least one recognition element.

28. The system of claim 17, wherein the at least one sensor comprises:
at least one signal emitter.

29. The system of claim 17, wherein the at least one sensor comprises:
at least one chemical sensor.

30. The system of claim 17, wherein the one or more substance comprises:
an indicator of a physiological state.

31. The system of claim 17, wherein the one or more substance comprises:
at least one metabolite.

32. The system of claim 17, wherein at least a portion of the at least one sensor is in dehydrated form.

33. The system of claim 17, wherein the at least one external device is configured to communicate with at least one network.

34. The system of claim 17, wherein the at least one external device is configured to detect at least one signal from the at least one sensor.

35. The system of claim 17, comprising:
at least one user interface.

36. The system of claim 17, comprising:
at least one signal emitter.

37. The system of claim 17, comprising:
at least one sensing device.

38. The system of claim 17, comprising:
sterile packaging for at least a portion of the system.

39. A method of detecting one or more substance in fluid comprising:
detecting and identifying one or more substance within a fluid inside of a beverage container including,
a vessel body defining a base and at least one side wall,
at least one sensor secured to the at least one side wall or embedded within the beverage container, the at least one sensor including a gel configured to be responsive when the one or more substance is detected,
a power source, and
a circuit operatively connected to the at least one sensor and the power source, wherein one or more of a portion of the power source or a portion of the circuit are embedded in the at least one side wall; and
interfacing one or more of the at least one sensor with an external device.

40. The method of claim 39, wherein the detecting one or more substance comprises:
detecting at least one biological analyte.

41. The method of claim 39, wherein the detecting one or more substance comprises:
contacting beverage fluid with the at least one sensor.

42. The method of claim 39, wherein the detecting one or more substance comprises:
binding the one or more substance with a recognition element.

43. The method of claim 39, wherein the detecting one or more substance comprises:
sequestering the one or more substance.

44. The method of claim 39, wherein the detecting one or more substance comprises:
detecting at least one metabolite of a provided agent.

45. The method of claim 39, wherein the detecting one or more substance comprises:
detecting one or more substance within the fluid with at least one chemical sensor.

46. The method of claim 39, wherein the detecting one or more substance comprises:
detecting one or more substance directly.

47. The method of claim 39, wherein the detecting one or more substance comprises:
detecting one or more taggant.

48. The method of claim 39, wherein the detecting one or more substance comprises:
detecting one or more signal with at least one detector integral to the external device.

49. The method of claim 39, wherein the interfacing one or more of the at least one sensor with an external device comprises:
generating a signal configured to be detected by the external device.

50. The method of claim 39, comprising:
contacting the fluid with at least one signaling element configured to signal contact with the fluid relative to at least one of time, presence of a target material, or presence of an amount of a target material.

51. The method of claim 39, comprising:
providing at least one provided agent with the beverage container; and
detecting one or more metabolite of the provided agent with the at least one sensor.

52. The method of claim 39, comprising:
communicating information regarding at least one detection result to at least one system user.

53. The method of claim 39, comprising:
communicating information regarding at least one sensor result to at least one system user.

* * * * *

UNITED STATES PATENT AND TRADEMARK OFFICE
CERTIFICATE OF CORRECTION

PATENT NO. : 9,024,766 B2
APPLICATION NO. : 12/584364
DATED : May 5, 2015
INVENTOR(S) : Leroy E. Hood et al.

Page 1 of 1

It is certified that error appears in the above-identified patent and that said Letters Patent is hereby corrected as shown below:

In the claims

Column 47, Line 35, Claim 17:

"being configured to sense a difference substance via a" should read --being configured to sense a different substance via a--

Column 47, Line 63, Claim 22 should read:

--22. The system of claim 17, wherein at least...--

Signed and Sealed this
Twentieth Day of October, 2015

Michelle K. Lee
*Director of the United States Patent and Trademark Office*